(12) United States Patent
Melis et al.

(10) Patent No.: US 10,563,228 B2
(45) Date of Patent: Feb. 18, 2020

(54) PRODUCTION OF β-PHELLANDRENE USING GENETICALLY ENGINEERED PHOTOSYNTHETIC MICROORGAMISMS

(71) Applicant: THE REGENTS OF THE UNIVERSITY OF CALIFORNIA, Oakland, CA (US)

(72) Inventors: Anastasios Melis, El Cerrito, CA (US); Fiona K. Davies, Berkeley, CA (US); Hsu-Ching Chen Wintz, El Cerrito, CA (US); Andreas Zurbriggen, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 157 days.

(21) Appl. No.: 15/888,939

(22) Filed: Feb. 5, 2018

(65) Prior Publication Data

US 2018/0171363 A1    Jun. 21, 2018

Related U.S. Application Data

(62) Division of application No. 14/376,392, filed as application No. PCT/US2013/024908 on Feb. 6, 2013, now Pat. No. 9,951,354.

(60) Provisional application No. 61/595,610, filed on Feb. 6, 2012.

(51) Int. Cl.
*C12N 9/88* (2006.01)
*C12N 15/52* (2006.01)
*C12N 1/20* (2006.01)
*C12P 5/00* (2006.01)

(52) U.S. Cl.
CPC ............... *C12P 5/002* (2013.01); *C12N 1/20* (2013.01); *C12N 9/88* (2013.01); *C12N 15/52* (2013.01); *C12P 5/007* (2013.01); *C12Y 402/03052* (2013.01)

(58) Field of Classification Search
None
See application file for complete search history.

(56) References Cited

U.S. PATENT DOCUMENTS

| | | | |
|---|---|---|---|
| 9,951,354 B2 * | 4/2018 | Melis | .............. C12P 5/007 |
| 2002/0142408 A1 | 10/2002 | DiCosimo | |
| 2002/0164706 A1 | 11/2002 | Huang et al. | |
| 2009/0053797 A1 | 2/2009 | Shiba | |
| 2010/0196982 A1 | 8/2010 | Anderson | |
| 2011/0053216 A1 | 3/2011 | Vermaas | |
| 2012/0135490 A1 | 5/2012 | Melis | |

(Continued)

FOREIGN PATENT DOCUMENTS

| | | |
|---|---|---|
| WO | 2009-036067 A2 | 3/2009 |
| WO | 2009-111513 A1 | 9/2009 |
| WO | 2012/145692 A2 | 10/2012 |

OTHER PUBLICATIONS

U.S. Appl. No. 61/522,685, filed Aug. 11, 2011, Specification, Claims, Abstract, Drawings and Sequence Listing.

(Continued)

*Primary Examiner* — Richard C Ekstrom
(74) *Attorney, Agent, or Firm* — Kilpatrick Townsend & Stockton LLP

(57) ABSTRACT

The present invention provides methods and compositions for producing β-phellandrene hydrocarbons from a photosynthetic microorganism such as cyanobacteria.

11 Claims, 16 Drawing Sheets

Specification includes a Sequence Listing.

(56) References Cited

U.S. PATENT DOCUMENTS

| | | |
|---|---|---|
| 2012/0276637 A1 | 11/2012 | Zhou |
| 2014/0370562 A1 | 12/2014 | Melis |
| 2015/0218589 A1 | 8/2015 | Furutani |
| 2018/0171363 A1* | 6/2018 | Melis .................. C12P 5/007 |

OTHER PUBLICATIONS

U.S. Appl. No. 14/376,392, "Restriction Requirement," dated Dec. 10, 2015, 6 pages.

U.S. Appl. No. 14/376,392, "Non-Final Office Action," dated Jun. 1, 2016, 15 pages.

U.S. Appl. No. 14/376,392, "Final Office Action," dated Sep. 29, 2016, 10 pages.

U.S. Appl. No. 14/376,392, "Non-Final Office Action," dated Apr. 6, 2017, 13 pages.

U.S. Appl. No. 14/376,392, "Final Office Action," dated Oct. 18, 2017, 11 pages.

U.S. Appl. No. 14/376,392, "Advisory Action," dated Dec. 27, 2017, 2 pages.

International Search Report and Written Opinion dated Jun. 25, 2013 of International Patent Application No. PCT/US2013/024908, 15 pages.

NCBI, GenBank accession No. ADQ73631.1 (Jan. 9, 2011).

Bentley et al., "Diffusion-Based for Carbon Dioxide Uptake and Isoprene Emission in Gaseous/Aqueous Two-Phase Photobioreactors by Photosynthetic Microorganisms", *Biotechnology and Bioengineering*, vol. 109, pp. 100-109 (2011).

Bohlmann et al., "cDNA Cloning, Characterization, and Functional Expression of four New Monoterpene Synthase Members of the Tpsd Gene Family from Grand Fir (*Abies grandis*)", *Arch. Biochem. Biophys.* vol. 368, No. 2, pp. 232-243 (1999).

Chou et al., "Cloning and characterization of Pfl_1841, a 2-methylenebornane synthase in Pseudomonas fluorescens PfO-1", *Tetrahedron*, vol. 67, No. 35, pp. 6627-6632 (2011).

Degenhardt et al., "Monoterpene and sesquiterpene synthases and the origin of terpene skeletal diversity in Plants", *Phytochemistry*, vol. 70, No. 15-16, pp. 1621-1637 (2009).

Demissie et al., "Cloning and functional characterization of β-phellandrene synthase from *Lavandula angustifolia*", *Planta*, vol. 233, pp. 685-696 (2011).

Ershov et al., "Lsoprenoid Biosynthesis in *Synechocystis* sp. Strain PCC6803 is Stimulated by Compounds of thePentose Phosphate Cycle but Not by Pyruvate or Deoxyxylulose-5-Phosphate", *J. Bacteriol.* vol. 184, No. 18, pp. 5045-5051 (2002).

Keeling et al., Transcriptome mining, functional characterization, and phylogeny of a large terpene synthase gene family in spruce (*Picea* spp.), *BMC Plant Biol.*, vol. 11, pp. 43, 14 pages (2011).

Lindberg et al., "Engineering a platform for photosynthetic isoprene production in cyanobacteria, using Sunechocystis as the model organism", *Metab Eng.* vol. 12, pp. 70-79 (2010), with supplementary data.

Nieuwenhuizen et al., Two terpene synthases are responsible for the major sesquiterpenes emitted from the flowers of kiwifruit (*Actinidia deliciosa*), *J. Exp. Bot.*, vol. 60, No. 11, pp. 3203-3219 (2009).

Reinsvold et al., "The production of the sesquiterpene β-caryophyllene in a transgenic strain of the cyanobacterium *Synechocystis*" *J. Plant Physiol.* vol. 168, pp. 848-852 (2011).

Roeder et al., "Regulation of simultaneous synthesis of floral scent terpenoids by the 1, 8-cineole synthase of *Nicotiana suaveolens*", *Plant Mol Biol.* vol. 65, No. 1, pp. 107-124 (2007).

Rohmer et al., "Isoprenoid biosynthesis in bacteria: a novel pathway for the early steps leading to isopentenyl diphosphate", *Biochem. J.*, vol. 295, pp. 517-524 (1993).

Schilmiller et al., "Monoterpenes in the glandular trichomes of tomato are synthesized from a neryl diphosphate precursor rathr than geranyl diphosphate", *Proc. Nat. Acad. Sci. U.S.A.* vol. 106, pp. 10865-10878 (2009), with supplementary data.

Sharkey et al., "Isoprene Emission from Plants: Why and How" *Ann. Bol.*, vol. 101, No. 1, pp. 5-18 (2002).

Wise et al., Monoterpene Synthases from Common Sage (*Salvia officinalis*), *J. Biol. Chem.*, vol. 273, pp. 14891-14899 (1998).

\* cited by examiner

FIG. 2

CLUSTAL 2.1 multiple sequence alignment

```
P.sitchensis2      ------------------------MAIVSSVPLASKSCLHKSLIS-SIHKLKPFCRTIPTLGMSRPGKY
P.sitchensis3      ------------------------MAIVSSVPLASKSCLHKSLIS-SIHKLKPFCRTIPTLGMSRPGKY
P.sitchensis1      ------------------------MAIVSSVPLASKSCLHKSLIS-SIHKLKPFCRTIPTLGMSRPGKY
P.sitchensis4      ------------------------MAIVSSVPLASKSCLHKSLIS-SIHKLKPFCRTIPTLGMSRPGKS
A.grandis          ------------------------MALVSSAPKSCLHKSLIRSTHHELKPLRRTIPTLGMCRRGKS
L.angustifolia     ------------------------MSTIIAIQVLLPIPTTKTYPSHDLEKSSSRCRSSST
S.lycopersicum     MIVGYRSTIITLSHPKLGNGKTISSNAIFQRSCRVRCSHSTTSSMNGFEDARDRIRESFG
                                            .  :  .        :  * .

P.sitchensis2      VMP---------------------------------------------------------
P.sitchensis3      VMP---------------------------------------------------------
P.sitchensis1      VMP---------------------------------------------------------
P.sitchensis4      VMP---------------------------------------------------------
A.grandis          FTPSV-------------------------------------------------------
L.angustifolia     PRP---------------------------------------------------------
S.lycopersicum     KLELSPSSYDTAWVAMVPSRHSLNEPCFPQCLDWIIENQREDGSWGLNPTHPLLLKDSLS P.sitchensis2      ------SMSMSSPVSDDG-VQRRTGGYHSNLWNDDIIQFLS--------------TTYGEPA
P.sitchensis3      ------SMSMSSPVSDDG-VQRRTGGYHSNLWNDDIIQFLS--------------TPYGEPA
P.sitchensis1      ------SMSMSSPVSDDG-VQRRTGGYHSNLWNDDIIQFLS--------------TPYGEPA
P.sitchensis4      ------SMSMSSPVSDDG-VQRRTGGYHSNLWNDDIIQFLS--------------TPYGEPA
A.grandis          ------SMSLTTAVSDDG-LQRKIGDYHSNLWDDDFIQSLS--------------TPYGEPS
L.angustifolia     ------RLCCSLQVSDPIPTGRSGGYPPALWDFDTIQSLN--------------TEYKGER
S.lycopersicum     STLACLLALTKWRVGDEQIKRGLGFIETYGWAVDNKDQISPLGFEVIFSSMIKSAEKLDL
                         :  .                *   *    *    * : :.            :

P.sitchensis2      YRERGERLIDEVKNMFNSISMEDVEFS-P-------------------------------
P.sitchensis3      YRERGERLIDEVKNMFNSISMEDVEFS-P-------------------------------
P.sitchensis1      YRERGERLIDEVKNMFNSISMEDVEFS-P-------------------------------
P.sitchensis4      YRERGERLIDEVKNMFNSISMEDVEFS-P-------------------------------
A.grandis          YREPAEKLIGEVKEMFNSMPSEDGESMSP-------------------------------
L.angustifolia     HMRREEDLIGQVREMLVHEVEDP-------------------------------------
S.lycopersicum     NLPLNLHLVNLVKCKRDSTIKRNVEYMGEGVGELCDWKEMIKLHQRQNGSLFDSPATTAA
                          *:. *:

P.sitchensis2      ---------------------------------LNDLIQRLWIVDSVERLGIDRHFKNEIKST
P.sitchensis3      ---------------------------------LNDLIQRLWIVDSVERLGIDRHFKNEIKST
P.sitchensis1      ---------------------------------LNDLIQRLWIVDSVERLGIDRHFKNEIKST
P.sitchensis4      ---------------------------------LNDLIQRLWIVDSVERLGIDRHFKNEIKST
A.grandis          ---------------------------------LNDLIERLWMVDSVERLGIDRHFKKEIKSA
L.angustifolia     ----------------------TPQLEFIDDLHKLGISCHFENEILQI
S.lycopersicum     ALIYHQHDQKCYQYLNSIFQQHKNWVPTMYPTKVHSLLCLVDTLQNLGVHRHFKSEIKKA
                                                    *  ::* : ..**:  **:.**  .

P.sitchensis2      LDYVYSYWTQKGIGCGIESVVPDLNSTALGLRTLRLHGYPVSAEVLKHFQNQNGQFACSP
P.sitchensis3      LDYVYSYWTQKGIGCGIESVDPDLNSTALGLRTLRLHGYPVSAEVLKHFQNQNGQFACSP
P.sitchensis1      LDYVYSYWTQKGIGCGIESVVPDLNSTALGLRTLRLHGYPVSAEVLKHFQNQNGQFACSP
P.sitchensis4      LDYVYSYWTQKGIGCGIESVVPDLNSTALGLRTLRLHGYPVSAEVLKHFQNQNGQFACSP
A.grandis          LDYVYSYWNEKGIGCGRDSVFPDVNSTASGFRTLRLHGYSVSSEVLKVFQDQNGQFAFSP
L.angustifolia     LKSIYLNQN----------YKRDLYSTSLAFRLLRQYGFILPQEVFDCFKNEEG--TDFK
S.lycopersicum     LDEIYRLWQQKN-----EQIFSNVTHCAMAFRLLRMSYYDVSSDELAEFVDEEHFPATNG
                   * . :*             :  :   . .:* **       :  :: :   *  ::    :

P.sitchensis2      SETEGEMRSIVNLYRASLIAFPGEKVMEEAEIFS-TKYLKEALQKIPVSSLSREIGDVLE
P.sitchensis3      SETEGEMRSIVNLYRASLIAFPGEKVMEEAEIFS-TKYLKEALQKIPVSSLSREIGDVLE
P.sitchensis1      SETEGEMRSIVNLYRASLIAFPGEKVMEEAEIFS-TKYLKEALQKIPVSSLSREIGDVLE
P.sitchensis4      SETEGEMRSIVNLYRASLIAFPGEKVMEEAEIFS-TKYLKEALQKIPVSSLSREIGDVLE
A.grandis          STKERDIRTVLNLYRASFIAFPGEKVMEEAEIFS-SRYLKEAVQKIPVSSLSQEIDYTLE
L.angustifolia     PSFGRDIKGLIQLYEASFLSRKGEETLQLAREFA-TKILQKEVD-------EREFATKME
S.lycopersicum     KYKSHVEILELHKASQLAIDHEKDDILDKINNWTRAFMEQKLLNNGFIDRMSKKEVELAL
                       :         :      :.   .:   .: : .::  .::   ::        . .:

P.sitchensis2      QDWHTNLPRLEARNYIDVFGQDT------KDTKLYMKTEKLLELAKLEFNIFQSLQKTEL
P.sitchensis3      QDWHTNLPRLEARNYIDVFGQDT------KDTKLYMKTEKLLELAKLEFNIFQSLQKTEL
P.sitchensis1      QDWHTNLPRLEARNYIDVFGQDT------KDTKLYMKTEKLLELAKLEFNIFQSLQKTEL
P.sitchensis4      QDWHTNLPRLEARNYIDVFGQDT------KDTKLYMKTEKLLELAKLEFNIFQSLQKTEL
A.grandis          YGWHTNMPRLETRNYLDVFGHPTSPWL-KKKRTQYLDSEKLLELAKLEFNIFHSLQQKEL
L.angustifolia     FPSHWTVQMPNARPFIDAYRRRP-----------DMNPVVLELAILDTNIVQAFQEEL
S.lycopersicum     RKFYTTSHLAENRRYIKSYEENNFKILKAAYRSPNINNKDLLAFSIHDFELCQAQHREEL
                    :  .    :   :  *::: :  .             .:* ::  ::  :: :  **
```

*FIG. 2 (continued)*

```
P.sitchensis2    DSLLRWWKDS-GFHHITFSRHLHVEYYTLASCIAIEPQHSRFRLGFAKACHVITILDDMY
P.sitchensis3    DSLLRWWKDS-GFHHITFSRHLHVEYYTLASCIAIEPQHSRFRLGFAKACHVITILDDMY
P.sitchensis1    DSLLRWWKDS-GFPHITFSRHLHVEYYTLASCIAFEPQHSRFRLGFAKACHVITILDDMY
P.sitchensis4    DSLLRWWKDS-GFHHITFSRHLHVEYYTLASCIAFEPQHSRFRLGFAKACHVITILDDMY
A.grandis        QYLSRWWIHS-GLPELTFGRHRHVEYYTLSSCIATEPKHSAFRLGFAKTCHLITVLDDIY
L.angustifolia   KETSRWWESTGIVQELPFVRDRIVEGYFWTIGVTQRREHGYERIMTAKVIALVTCLDDIY
S.lycopersicum   QQLKRWFEDYRLDQLGLAERYIHASYLFGVTVIP-EPELSDARLMYAKYVMLLTIVDDHF
                 . **:           *   ..      :. .:.   *: **    ::*  :**  :

P.sitchensis2    DVFGTIDELELFTAQIKRWDPSATDCLP-KYMKRMYMILYDMVNEMSREAETAQGRDTLN
P.sitchensis3    DVFGTIDELELFTAQIKRWDPSATDCLP-KYMKRMYMILYDMVNEMSREAETAQGRDTLN
P.sitchensis1    DVFGTIDELELFTAQIKRWDPSATDCLP-KYMKRMYMILYDMVNEMSREAETAQGRDTLN
P.sitchensis4    DVFGTIDELELFTAQIKRWDPSATDCLP-KYMKRMYMILYDMVNEMSREAETAQGRDTLN
A.grandis        DTFGTMDEIELFNEAVRRWNPSEKERLP-EYMKEIYMALYEALTDMAREAEKTQGRDTLN
L.angustifolia   DVYGTIEELQLFTSTIQRWDLESMKQLP-TYMQVSFLALHNFVTEVAYDTLKKKGYNSTP
S.lycopersicum   ESFASKDECFNIIELVERWDDYASVGYKSEKVKVFFSVFYKSIEELATIAEIKQGRSVKN
                 : :.:  :*    :.**:         ::       ::. :::  :::     :* .

P.sitchensis2    YARQAWEDFIDSYMQE-AKWIATGYLPTFDEYFENGKVSSGHRVAALQPILTMDIPFPHD
P.sitchensis3    YARQAWEDFIDSYMQE-AKWIATGYLPTFDEYFENGKVSSGHRVAALQPILTMDIPFPHD
P.sitchensis1    YARQAWEDFIDSYMQE-AKWIATGYLPTFDEYFENGKVSSGHRVAALQPILTMDIPFPHD
P.sitchensis4    YARQAWEDFIDSYMQE-AKWIATGYLPTFDEYFENGKVSSGHRVAALQPILTMDIPFPHD
A.grandis        YARKAWEVYLDSYTQE-AKWIASGYLPTFEEYLENAKVSSGHRAAALTPLLTLDVPLPDD
L.angustifolia   YLRKTWVDLVESYIKE-ATWYYNGYKPSMQEYLNNAWISVGS-------MAILNHLFFRF
S.lycopersicum   HLINLWLELMKLMLMERVEWCSGKTIPSIEEYLYVTSITFCAKLIPLSTQYFLGIKISKD
                 :  : *   :.  *  .   *      *:::**:       ::         :. :.

P.sitchensis2    ILKEVDFPSKLNDLASAILRLRGDTRCYKADRARGEEASCISCYMKDNPGATEEDALSHI
P.sitchensis3    ILKEVDFPSKLNDLASAILRLRGDTRCYKADRARGEEASCISCYMKDNPGATEEDALSHI
P.sitchensis1    ILKEVDFPSKLNDLASAILRLRGDTRCYKADRARGEEASCISCYMKDNPGATEEDALSHI
P.sitchensis4    ILKEVDFPSKLNDLASAILRLRGDTRCYKADRARGEEASCISCYMKDNPGATEEDALSHI
A.grandis        VLKGIDFPSRFNDLASSFLRLRGDTRCYKADRDRGEEASSISCYMKDNPGLTEEDALNHI
L.angustifolia   TNERMHKYRDMNRVSSNIVRLADDMGTSLAEVERGDVPKAIQCYMNETN-ASEEEAREYV
S.lycopersicum   LLESDEICGLWNCSGRVMRILN-----DLQDSKREQKEVSINLVTLLMKSMSEEEAIMKI
                 :      *  . *      :     *     :  .*.      ;**:*     :

P.sitchensis2    NAVISDVIKGLNWELLNPNS-----SVPISSKKHVFDVSRALHYGYKYR-DGYSVSNIET
P.sitchensis3    NAVISDVIKGLNWELLNPNS-----SVPISSKKHVFDVSRALHYGYKYR-DGYSVSNIET
P.sitchensis1    NAVISDVIKGLNWELLNPNS-----SVPISSKKHVFDVSRALHYGYKYR-DGYSVSNIET
P.sitchensis4    NAVINDVIKGLNWELLNPNS-----SVPISSKKHVFDVSRALHYGYKYR-DGYSVSNIET
A.grandis        NAMINDIIKELNWELLKPDS-----NIPMTARKHAYEITRAFHQLYKYR-DGFSVATQET
L.angustifolia   RRVIQEEWEKLNTELMRDDDDDDFTLSKYYCEVVANLTRMAQFIYQDGSDGFGMKDSKV
S.lycopersicum   KEILEMNRRELLKMVLVQKKGS---QLPQLCKDIFWRTSKWAHFTYSQT-DGYRIAEEMK
                 . ::.  . *   ::.  .      :.       ::  :  *,  **:  :

P.sitchensis2    KSLVMRTLLESVPF
P.sitchensis3    KSLVMRTLLESVPF
P.sitchensis1    KSLVMRTLLESVPF
P.sitchensis4    KSLVMRTLLESVPF
A.grandis        KSLVRRTVLEPVPL
L.angustifolia   NRLLKETLIERYE-
S.lycopersicum   NHIDEVFYKPLNH-
                 :  :
```

A

SEQ ID NO:1 Amino acid sequence of the mature S-β-PHLS protein

MCSLQVSDPIPTGRRSGGYPPALWEFDTHQSLNTEYKGERHMRREEDLIGQVRIEMLVHEVEDPTPQLEFHDDLHKLGISCFHFENEILQILKSIYLNQNYKRDLYSTSLAFRLLRQYGFILPQEVFDCF
KMEEGTDFKPSFGRDIKGLLQLYEASFLSRKGEETLQLAREFATKILQKEVDEREFATKMFPSHWTVQMPNARPPIDAYRRRPIDMNPVVLELAILDTNIVQAQFQEELKETSRWWESTGIVQELP
FVRDRIVEGYFWTGVTQRREHGYERIMTAKVIALVTCLDIYDVYGHEELQLFTSTIQRWDLESSMKQLPTYMQVSPLALHNFVTEVAYDTILKKKGYNSTPYLRKTWVDLVESYIKEATWYYN
GYNTPSMQEYLNNAWISVGSSMAIHLNHLFRFTNERMHKYRDMNRVSSNIVRLADDMGTSLAEVERGDVPKAIQCYMNEFNASEEEAREYRRVIQEEWEKLNTELMRDEBDEDFTLSKYYCE
VVANLIRMAQFIYQDGSDGFGMEKDSKVNRLLKEILEERYE*

B

SEQ ID NO:2 The native La-β-PHLS cDNA nucleotide sequence

ATGTGTAGCTTATTGCGATACAAGTTGTCTTCTATTCAACTACTAAAACATACCCAGTCATGACTGGAGAAGTCTCTTGCGGTGTGCTCCTCCACTCCTCGCC
CTAGACTGTTGCTCGTTGCAGGTGAGTGAGTGCAGGTCGATCCCAACGGCGGCGATCCGAGGCTACCGGGATGCCCCCGCCTATGGGATTTGCAGCACTATTCAATCGTCAACACCGAGTATAAGG
[additional sequence lines]

C

SEQ ID NO:3 Codon-optimized version of the L. angustifolia (La-β-PHLS) cDNA nucleotide sequence TTAATTAACATATGTGTAGTTTGCAAGTTTCTGATCCTATTCCTACCGGACGCCGTTCCGGTGGTTATCCCGGCCTTATGGCGATTTCGATCATTCAATCCCTGAATACCGAATATAAG
[additional sequence lines]

FIG. 3

SEQUENCE LISTING

<160> NUMBER OF SEQ ID NOS: 20

<210> SEQ ID NO 1
<211> LENGTH: 540
<212> TYPE: PRT
<213> ORGANISM: Lavandula angustifolia
<220> FEATURE:
<223> OTHER INFORMATION: lavender cultivar Lady mature beta-phellandrene
      synthase (beta-PHLS, S-beta-PHLS)

<400> SEQUENCE: 1

Met Cys Ser Leu Gln Val Ser Asp Pro Ile Pro Thr Gly Arg Arg Ser
1               5                   10                  15

Gly Gly Tyr Pro Pro Ala Leu Trp Asp Phe Asp Thr Ile Gln Ser Leu
            20                  25                  30

Asn Thr Glu Tyr Lys Gly Glu Arg His Met Arg Arg Glu Asp Leu
        35                  40                  45

Ile Gly Gln Val Arg Glu Met Leu Val His Glu Val Glu Asp Pro Thr
    50                  55                  60

Pro Gln Leu Glu Phe Ile Asp Asp Leu His Lys Leu Gly Ile Ser Cys
65                  70                  75                  80

His Phe Glu Asn Glu Ile Leu Gln Ile Leu Lys Ser Ile Tyr Leu Asn
                85                  90                  95

Gln Asn Tyr Lys Arg Asp Leu Tyr Ser Thr Ser Leu Ala Phe Arg Leu
            100                 105                 110

Leu Arg Gln Tyr Gly Phe Ile Leu Pro Gln Glu Val Phe Asp Cys Phe
        115                 120                 125

Lys Asn Glu Glu Gly Thr Asp Phe Lys Pro Ser Phe Gly Arg Asp Ile
    130                 135                 140

Lys Gly Leu Leu Gln Leu Tyr Glu Ala Ser Phe Leu Ser Arg Lys Gly
145                 150                 155                 160

Glu Glu Thr Leu Gln Leu Ala Arg Glu Phe Ala Thr Lys Ile Leu Gln
                165                 170                 175

Lys Glu Val Asp Glu Arg Glu Phe Ala Thr Lys Met Glu Phe Pro Ser
            180                 185                 190

His Trp Thr Val Gln Met Pro Asn Ala Arg Pro Phe Ile Asp Ala Tyr
        195                 200                 205

Arg Arg Arg Pro Asp Met Asn Pro Val Val Leu Glu Leu Ala Ile Leu
    210                 215                 220

Asp Thr Asn Ile Val Gln Ala Gln Phe Gln Glu Leu Lys Glu Thr
225                 230                 235                 240

Ser Arg Trp Trp Glu Ser Thr Gly Ile Val Gln Glu Leu Pro Phe Val
                245                 250                 255

```
Arg Asp Arg Ile Val Glu Gly Tyr Phe Trp Thr Ile Gly Val Thr Gln
            260                 265                 270

Arg Arg Glu His Gly Tyr Glu Arg Ile Met Thr Ala Lys Val Ile Ala
            275                 280                 285

Leu Val Thr Cys Leu Asp Asp Ile Tyr Asp Val Tyr Gly Thr Ile Glu
            290                 295                 300

Glu Leu Gln Leu Phe Thr Ser Thr Ile Gln Arg Trp Asp Leu Glu Ser
305                 310                 315                 320

Met Lys Gln Leu Pro Thr Tyr Met Gln Val Ser Phe Leu Ala Leu His
                325                 330                 335

Asn Phe Val Thr Glu Val Ala Tyr Asp Thr Leu Lys Lys Lys Gly Tyr
            340                 345                 350

Asn Ser Thr Pro Tyr Leu Arg Lys Thr Trp Val Asp Leu Val Glu Ser
            355                 360                 365

Tyr Ile Lys Glu Ala Thr Trp Tyr Tyr Asn Gly Tyr Lys Pro Ser Met
            370                 375                 380

Gln Glu Tyr Leu Asn Asn Ala Trp Ile Ser Val Gly Ser Met Ala Ile
385                 390                 395                 400

Leu Asn His Leu Phe Phe Arg Phe Thr Asn Glu Arg Met His Lys Tyr
                405                 410                 415

Arg Asp Met Asn Arg Val Ser Ser Asn Ile Val Arg Leu Ala Asp Asp
            420                 425                 430

Met Gly Thr Ser Leu Ala Glu Val Glu Arg Gly Asp Val Pro Lys Ala
            435                 440                 445

Ile Gln Cys Tyr Met Asn Glu Thr Asn Ala Ser Glu Glu Ala Arg
            450                 455                 460

Glu Tyr Val Arg Arg Val Ile Gln Glu Glu Trp Glu Lys Leu Asn Thr
465                 470                 475                 480

Glu Leu Met Arg Asp Asp Asp Asp Asp Phe Thr Leu Ser Lys
                485                 490                 495

Tyr Tyr Cys Glu Val Val Ala Asn Leu Thr Arg Met Ala Gln Phe Ile
            500                 505                 510

Tyr Gln Asp Gly Ser Asp Gly Phe Gly Met Lys Asp Ser Lys Val Asn
            515                 520                 525

Arg Leu Leu Lys Glu Thr Leu Ile Glu Arg Tyr Glu
            530                 535                 540

<210> SEQ ID NO 2
<211> LENGTH: 1746
<212> TYPE: DNA
<213> ORGANISM: Lavandula angustifolia
<220> FEATURE:
<223> OTHER INFORMATION: native lavender cultivar Lady beta-phellandrene
      synthase (La-beta-PHLS) cDNA
<220> FEATURE:
<221> NAME/KEY: CDS
<222> LOCATION: (1)...(1746)
<223> OTHER INFORMATION: native lavender cultivar Lady beta-phellandrene
      synthase (La-beta-PHLS)

<400> SEQUENCE: 2
atgtctacca ttattgcgat acaagtgttg cttcctattc caactactaa aacataccct      60
agtcatgact tggagaagtc ctcttcgcgg tgtcgctcct cctccactcc tcgccctaga    120
ctgtgttgct cgttgcaggt gagtgatccg atcccaacgg ccggcgatc cggaggctac     180 ccgcccgccc tatgggattt cgacactatt caatcgctca acaccgagta taagggagag    240
```

```
aggcacatga gaagggaaga agacctaatt gggcaagtta gagagatgct ggtgcatgaa    300
gtagaggatc ccactccaca gctggagttc attgatgatt tgcataagct tggcatatct    360
tgccattttg agaatgaaat cctccaaatc ttgaaatcca tatatcttaa tcaaaactac    420
aaaagggatt tgtactcaac atctctagca ttcagactcc tcagacaata tggcttcatc    480
cttccacaag aagtatttga ttgtttcaag aatgaggagg gtacggattt caagccaagc    540
ttcggccgtg atatcaaagg cttgttacaa ttgtatgaag cttcttttcct atcaagaaaa   600 ggagaagaaa ctttacaact agcaagagag tttgcaacaa agattctgca aaaagaagtt    660
gatgagagag agtttgcaac caagatggag ttcccttctc attggacggt tcaaatgccg    720
aatgcaagac ctttcatcga tgcttaccgt aggaggccgg atatgaatcc agttgtgctc    780
gagctagcca tacttgatac aaatatagtt caagcacaat tcaagaaga actcaaagag     840 acctcaaggt ggtgggagag tacaggcatt gtccaagagc ttccatttgt gagggatagg    900
attgtggaag ctacttttg gacgattgga gtgactcaga dacgcgagca tggatacgaa     960
agaatcatga ccgcaaaggt tattgcctta gtaacatgtt tagacgacat atacgatgtt   1020
tatggcacga tagaagagct tcaacttttc acaagcacaa tccaaagatg ggatttggaa   1080
tcaatgaagc aactccctac ctacatgcaa gtaagctttc ttgcactaca aactttgta    1140 accgaggtgg cttacgatac tctcaagaaa aagggctaca actccacacc atatttaaga   1200
aaaacgtggg tggatcttgt tgaatcatat atcaaagagg caacttggta ctacaacggt   1260
tataaaccta gtatgcaaga ataccttaac aatgcatgga tatcagtcgg aagtatggct   1320
atactcaacc acctcttctt ccggttcaca acgagagaa tgcataaata ccgcgatatg   1380
aaccgtgtct cgtccaacat tgtgaggctt gctgatgata tgggaacatc attggctgag   1440
gtggagagag gggacgtgcc gaaagcaatt caatgctaca tgaatgagac gaatgcttct   1500
gaagaagaag caagagaata tgtaagaaga gtcatacagg aagaatggga aaagttgaac   1560
acagaattga tgcgggatga tgatgatgat gatgatttta cactatccaa atattactgt   1620
gaggtggttg ctaatcttac aagaatggca cagtttatat accaagatgg atcggatggc   1680
ttcggcatga agattccaa ggttaataga ctgctaaaag acgttgat cgagcgctac     1740 gaataa                                                              1746
```

<210> SEQ ID NO 3
<211> LENGTH: 1648
<212> TYPE: DNA
<213> ORGANISM: Artificial Sequence
<220> FEATURE:
<223> OTHER INFORMATION: synthetic codon-optimized variant of lavender
      Lavandula angustifolia beta-phellandrine synthase (beta-PHLS)
      cDNA minus chloroplast transit peptide for expression in
      glucose-tolerant cyanobacterial strain Synechocystis sp. PCC
      6803 or E. coli (S-beta-PHLS, La-S-beta-PHLS)
<220> FEATURE:
<221> NAME/KEY: CDS
<222> LOCATION: (12)...(1634)
<223> OTHER INFORMATION: synthetic codon-optimized variant of lavender
      Lavandula angustifolia beta-phellandrine synthase (beta-PHLS)
      minus chloroplast transit peptide for expression in
      glucose-tolerant cyanobacterial strain Synechocystis sp. PCC 6803
      or E. coli (S-beta-PHLS, La-S-beta-PHLS)

<400> SEQUENCE: 3

```
ttaattaaca tatgtgtagt ttgcaagttt ctgatcctat tcctaccgga cgccgttccg     60
gtggttatcc cccggcctta tgggatttcg atactattca atccctgaat accgaatata   120
agggcgaacg tcacatgcgt cgggaagaag acttaattgg tcaagttcgg gaaatgttgg   180
```

```
tgcacgaagt agaagatccc actccccagt tggaattcat tgacgatctg cataaattgg      240
gcatttcctg ccatttgaa aacgagattc tgcaaattct caaatccatt tatctcaacc       300
aaaactataa acgggacctc tattctacca gtttagcctt ccgtctcttg cgtcaatacg      360
ggtttatctt gccgcaggaa gtttttgact gctttaaaaa cgaagaaggt acggatttta     420
aacccagctt cggccgggat attaagggtc tgttacagtt gtacgaagcc tccttttgt      480 cccggaaggg ggaagaaact ttacaactcg cccgcgaatt tgctaccaaa atcttgcaaa    540
aggaagtcga tgaacgggaa tttgctacta aaatggaatt tcccagtcac tggaccgtac    600
aaatgcctaa cgctcggcct tttatcgatg cctatcgtcg gcgtcccgac atgaaccccg    660
tggttctgga actcgccatt ctcgatacca atatcgtgca agctcagttt caagaagaat    720
tgaaggagac ctcccgttgg tgggaaagca cggggattgt tcaagaactg ccgtttgttc    780
gggaccggat tgtggaaggt tattttttgga ccattggtgt tactcaacgc cgtgaacacg   840
gttacgaacg tattatgacg gccaaagtca tcgctttggt gacctgtttg gatgatattt     900
atgacgtata tggcactatt gaagaattgc aactcttcac ctctacgatt cagcgttggg    960
atttggagtc tatgaagcag ttaccgactt atatgcaggt aagcttcctg gccttgcaca   1020
attttgtaac cgaagtggcc tatgatacgc tgaagaaaaa gggctacaac tctaccccct   1080
atttgcggaa gacttgggtg gatttggtcg aaagttacat taaggaagcc acttggtact   1140
ataatgggta caaaccctct atgcaggaat acctcaacaa cgcctggatc tctgtgggca    1200
gcatggctat tttgaatcat ttgttttttc gctttactaa tgaacgcatg cataagtacc   1260
gggacatgaa tcgtgtatcc tctaatattg tgcggttagc cgacgatatg ggaacctctt    1320
tggccgaagt tgaacgcggt gacgtgccca agctatcca atgttacatg aatgaaacga    1380
acgcctctga ggaggaggcc cgcgaatatg tgcggcgcgt tatccaggaa gaatgggaaa   1440
aactgaacac tgaactgatg cgcgacgacg acgatgacga tgatttcacc ttaagtaaat    1500
actactgcga agtcgttgct aacctgaccc ggatggctca gttcatttac caagatggtt   1560
ccgatgggtt tgggatgaaa gattccaaag taaatcgttt actgaaagaa acgctgattg    1620
agcgctatga gtgaagatct gcggccgc                                      1648
```

<210> SEQ ID NO 4
<211> LENGTH: 581
<212> TYPE: PRT
<213> ORGANISM: Lavandula angustifolia
<220> FEATURE:
<223> OTHER INFORMATION: lavender cultivar Lady beta-phellandrene synthase (La-beta-PHLS)
<220> FEATURE:
<221> NAME/KEY: PEPTIDE
<222> LOCATION: (1)...(42)
<223> OTHER INFORMATION: chloroplast transit peptide

<400> SEQUENCE: 4

Met Ser Thr Ile Ile Ala Ile Gln Val Leu Leu Pro Ile Pro Thr Thr
1               5                   10                  15

Lys Thr Tyr Pro Ser His Asp Leu Glu Lys Ser Ser Ser Arg Cys Arg
            20                  25                  30

Ser Ser Ser Thr Pro Arg Pro Arg Leu Cys Cys Ser Leu Gln Val Ser
        35                  40                  45

Asp Pro Ile Pro Thr Gly Arg Arg Ser Gly Gly Tyr Pro Pro Ala Leu
    50                  55                  60

Trp Asp Phe Asp Thr Ile Gln Ser Leu Asn Thr Glu Tyr Lys Gly Glu

```
            65                  70                  75                  80
Arg His Met Arg Arg Glu Glu Asp Leu Ile Gly Gln Val Arg Glu Met
                    85                  90                  95
Leu Val His Glu Val Glu Asp Pro Thr Pro Gln Leu Glu Phe Ile Asp
                    100                 105                 110
Asp Leu His Lys Leu Gly Ile Ser Cys His Phe Glu Asn Glu Ile Leu
                    115                 120                 125
Gln Ile Leu Lys Ser Ile Tyr Leu Asn Gln Asn Tyr Lys Arg Asp Leu
            130                 135                 140
Tyr Ser Thr Ser Leu Ala Phe Arg Leu Leu Arg Gln Tyr Gly Phe Ile
145                 150                 155                 160
Leu Pro Gln Glu Val Phe Asp Cys Phe Lys Asn Glu Glu Gly Thr Asp
                    165                 170                 175
Phe Lys Pro Ser Phe Gly Arg Asp Ile Lys Gly Leu Leu Gln Leu Tyr
                    180                 185                 190
Glu Ala Ser Phe Leu Ser Arg Lys Gly Glu Glu Thr Leu Gln Leu Ala
                    195                 200                 205
Arg Glu Phe Ala Thr Lys Ile Leu Gln Lys Glu Val Asp Glu Arg Glu
            210                 215                 220
Phe Ala Thr Lys Met Glu Phe Pro Ser His Trp Thr Val Gln Met Pro
225                 230                 235                 240
Asn Ala Arg Pro Phe Ile Asp Ala Tyr Arg Arg Pro Asp Met Asn
                    245                 250                 255
Pro Val Val Leu Glu Leu Ala Ile Leu Asp Thr Asn Ile Val Gln Ala
                    260                 265                 270
Gln Phe Gln Glu Glu Leu Lys Glu Thr Ser Arg Trp Trp Glu Ser Thr
                    275                 280                 285
Gly Ile Val Gln Glu Leu Pro Phe Val Arg Asp Arg Ile Val Glu Gly
            290                 295                 300
Tyr Phe Trp Thr Ile Gly Val Thr Gln Arg Arg Glu His Gly Tyr Glu
305                 310                 315                 320
Arg Ile Met Thr Ala Lys Val Ile Ala Leu Val Thr Cys Leu Asp Asp
                    325                 330                 335
Ile Tyr Asp Val Tyr Gly Thr Ile Glu Glu Leu Gln Leu Phe Thr Ser
                    340                 345                 350
Thr Ile Gln Arg Trp Asp Leu Glu Ser Met Lys Gln Leu Pro Thr Tyr
                    355                 360                 365
Met Gln Val Ser Phe Leu Ala Leu His Asn Phe Val Thr Glu Val Ala
            370                 375                 380
Tyr Asp Thr Leu Lys Lys Lys Gly Tyr Asn Ser Thr Pro Tyr Leu Arg
385                 390                 395                 400
Lys Thr Trp Val Asp Leu Val Glu Ser Tyr Ile Lys Glu Ala Thr Trp
                    405                 410                 415
Tyr Tyr Asn Gly Tyr Lys Pro Ser Met Gln Glu Tyr Leu Asn Asn Ala
                    420                 425                 430
Trp Ile Ser Val Gly Ser Met Ala Ile Leu Asn His Leu Phe Phe Arg
                    435                 440                 445
Phe Thr Asn Glu Arg Met His Lys Tyr Arg Asp Met Asn Arg Val Ser
            450                 455                 460
Ser Asn Ile Val Arg Leu Ala Asp Asp Met Gly Thr Ser Leu Ala Glu
465                 470                 475                 480
Val Glu Arg Gly Asp Val Pro Lys Ala Ile Gln Cys Tyr Met Asn Glu
                    485                 490                 495
```

```
Thr Asn Ala Ser Glu Glu Ala Arg Glu Tyr Val Arg Arg Val Ile
            500                 505                 510
Gln Glu Glu Trp Glu Lys Leu Asn Thr Glu Leu Met Arg Asp Asp
        515                 520                 525
Asp Asp Asp Asp Phe Thr Leu Ser Lys Tyr Tyr Cys Glu Val Val Ala
530                 535                 540
Asn Leu Thr Arg Met Ala Gln Phe Ile Tyr Gln Asp Gly Ser Asp Gly
545                 550                 555                 560
Phe Gly Met Lys Asp Ser Lys Val Asn Arg Leu Leu Lys Glu Thr Leu
                565                 570                 575
Ile Glu Arg Tyr Glu
            580

<210> SEQ ID NO 5
<211> LENGTH: 778
<212> TYPE: PRT
<213> ORGANISM: Solanum lycopersicum
<220> FEATURE:
<223> OTHER INFORMATION: tomato beta-phellandrene synthase (beta-PHLS)

<400> SEQUENCE: 5

Met Ile Val Gly Tyr Arg Ser Thr Ile Ile Thr Leu Ser His Pro Lys
1               5                   10                  15
Leu Gly Asn Gly Lys Thr Ile Ser Ser Asn Ala Ile Phe Gln Arg Ser
            20                  25                  30
Cys Arg Val Arg Cys Ser His Ser Thr Thr Ser Ser Met Asn Gly Phe
        35                  40                  45
Glu Asp Ala Arg Asp Arg Ile Arg Glu Ser Phe Gly Lys Leu Glu Leu
    50                  55                  60
Ser Pro Ser Ser Tyr Asp Thr Ala Trp Val Ala Met Val Pro Ser Arg
65                  70                  75                  80
His Ser Leu Asn Glu Pro Cys Phe Pro Gln Cys Leu Asp Trp Ile Ile
                85                  90                  95
Glu Asn Gln Arg Glu Asp Gly Ser Trp Gly Leu Asn Pro Thr His Pro
            100                 105                 110
Leu Leu Leu Lys Asp Ser Leu Ser Ser Thr Leu Ala Cys Leu Leu Ala
        115                 120                 125
Leu Thr Lys Trp Arg Val Gly Asp Glu Gln Ile Lys Arg Gly Leu Gly
    130                 135                 140
Phe Ile Glu Thr Tyr Gly Trp Ala Val Asp Asn Lys Asp Gln Ile Ser
145                 150                 155                 160
Pro Leu Gly Phe Glu Val Ile Phe Ser Ser Met Ile Lys Ser Ala Glu
                165                 170                 175
Lys Leu Asp Leu Asn Leu Pro Leu Asn Leu His Leu Val Asn Leu Val
            180                 185                 190
Lys Cys Lys Arg Asp Ser Thr Ile Lys Arg Asn Val Glu Tyr Met Gly
        195                 200                 205
Glu Gly Val Gly Glu Leu Cys Asp Trp Lys Glu Met Ile Lys Leu His
    210                 215                 220
Gln Arg Gln Asn Gly Ser Leu Phe Asp Ser Pro Ala Thr Thr Ala Ala
225                 230                 235                 240
Ala Leu Ile Tyr His Gln His Asp Gln Lys Cys Tyr Gln Tyr Leu Asn
                245                 250                 255
Ser Ile Phe Gln Gln His Lys Asn Trp Val Pro Thr Met Tyr Pro Thr
            260                 265                 270
```

```
Lys Val His Ser Leu Leu Cys Leu Val Asp Thr Leu Gln Asn Leu Gly
            275                 280                 285
Val His Arg His Phe Lys Ser Glu Ile Lys Lys Ala Leu Asp Glu Ile
    290                 295                 300
Tyr Arg Leu Trp Gln Gln Lys Asn Glu Gln Ile Phe Ser Asn Val Thr
305                 310                 315                 320
His Cys Ala Met Ala Phe Arg Leu Leu Arg Met Ser Tyr Tyr Asp Val
                325                 330                 335
Ser Ser Asp Glu Leu Ala Glu Phe Val Asp Glu His Phe Phe Ala
                340                 345                 350
Thr Asn Gly Lys Tyr Lys Ser His Val Glu Ile Leu Leu His Lys
                355                 360                 365
Ala Ser Gln Leu Ala Ile Asp His Glu Lys Asp Asp Ile Leu Asp Lys
    370                 375                 380
Ile Asn Asn Trp Thr Arg Ala Phe Met Glu Gln Lys Leu Leu Asn Asn
385                 390                 395                 400
Gly Phe Ile Asp Arg Met Ser Lys Lys Glu Val Glu Leu Ala Leu Arg
                405                 410                 415
Lys Phe Tyr Thr Thr Ser His Leu Ala Glu Asn Arg Arg Tyr Ile Lys
                420                 425                 430
Ser Tyr Glu Glu Asn Asn Phe Lys Ile Leu Lys Ala Ala Tyr Arg Ser
                435                 440                 445
Pro Asn Ile Asn Asn Lys Asp Leu Leu Ala Phe Ser Ile His Asp Phe
    450                 455                 460
Glu Leu Cys Gln Ala Gln His Arg Glu Gln Leu Gln Gln Leu Lys Arg
465                 470                 475                 480
Trp Phe Glu Asp Tyr Arg Leu Asp Gln Leu Gly Leu Ala Glu Arg Tyr
                485                 490                 495
Ile His Ala Ser Tyr Leu Phe Gly Val Thr Val Ile Pro Glu Pro Glu
                500                 505                 510
Leu Ser Asp Ala Arg Leu Met Tyr Ala Lys Tyr Val Met Leu Leu Thr
    515                 520                 525
Ile Val Asp Asp His Phe Glu Ser Phe Ala Ser Lys Asp Glu Cys Phe
    530                 535                 540
Asn Ile Ile Glu Leu Val Glu Arg Trp Asp Asp Tyr Ala Ser Val Gly
545                 550                 555                 560
Tyr Lys Ser Glu Lys Val Lys Val Phe Phe Ser Val Phe Tyr Lys Ser
                565                 570                 575
Ile Glu Glu Leu Ala Thr Ile Ala Glu Ile Lys Gln Gly Arg Ser Val
                580                 585                 590
Lys Asn His Leu Ile Asn Leu Trp Leu Glu Leu Met Lys Leu Met Leu
                595                 600                 605
Met Glu Arg Val Glu Trp Cys Ser Gly Lys Thr Ile Pro Ser Ile Glu
    610                 615                 620
Glu Tyr Leu Tyr Val Thr Ser Ile Thr Phe Cys Ala Lys Leu Ile Pro
625                 630                 635                 640
Leu Ser Thr Gln Tyr Phe Leu Gly Ile Lys Ile Ser Lys Asp Leu Leu
                645                 650                 655
Glu Ser Asp Glu Ile Cys Gly Leu Trp Asn Cys Ser Gly Arg Val Met
                660                 665                 670
Arg Ile Leu Asn Asp Leu Gln Asp Ser Lys Arg Glu Gln Lys Glu Val
                675                 680                 685
```

```
Ser Ile Asn Leu Val Thr Leu Leu Met Lys Ser Met Ser Glu Glu Glu
    690                 695                 700

Ala Ile Met Lys Ile Lys Glu Ile Leu Glu Met Asn Arg Arg Glu Leu
705                 710                 715                 720

Leu Lys Met Val Leu Val Gln Lys Lys Gly Ser Gln Leu Pro Gln Leu
                725                 730                 735

Cys Lys Asp Ile Phe Trp Arg Thr Ser Lys Trp Ala His Phe Thr Tyr
            740                 745                 750

Ser Gln Thr Asp Gly Tyr Arg Ile Ala Glu Glu Met Lys Asn His Ile
        755                 760                 765

Asp Glu Val Phe Tyr Lys Pro Leu Asn His
770                 775
```

<210> SEQ ID NO 6
<211> LENGTH: 630
<212> TYPE: PRT
<213> ORGANISM: Abies grandis
<220> FEATURE:
<223> OTHER INFORMATION: grand fir beta-phellandrene synthase
      (beta-PHLS)

<400> SEQUENCE: 6

```
Met Ala Leu Val Ser Ser Ala Pro Lys Ser Cys Leu His Lys Ser Leu
1               5                   10                  15

Ile Arg Ser Thr His His Glu Leu Lys Pro Leu Arg Arg Thr Ile Pro
            20                  25                  30

Thr Leu Gly Met Cys Arg Arg Gly Lys Ser Phe Thr Pro Ser Val Ser
        35                  40                  45

Met Ser Leu Thr Thr Ala Val Ser Asp Asp Gly Leu Gln Arg Arg Ile
50                  55                  60

Gly Asp Tyr His Ser Asn Leu Trp Asp Asp Phe Ile Gln Ser Leu
65                  70                  75                  80

Ser Thr Pro Tyr Gly Glu Pro Ser Tyr Arg Glu Arg Ala Glu Lys Leu
                85                  90                  95

Ile Gly Glu Val Lys Glu Met Phe Asn Ser Met Pro Ser Glu Asp Gly
            100                 105                 110

Glu Ser Met Ser Pro Leu Asn Asp Leu Ile Glu Arg Leu Trp Met Val
        115                 120                 125

Asp Ser Val Glu Arg Leu Gly Ile Asp Arg His Phe Lys Lys Glu Ile
130                 135                 140

Lys Ser Ala Leu Asp Tyr Val Tyr Ser Tyr Trp Asn Glu Lys Gly Ile
145                 150                 155                 160

Gly Cys Gly Arg Asp Ser Val Phe Pro Asp Val Asn Ser Thr Ala Ser
                165                 170                 175

Gly Phe Arg Thr Leu Arg Leu His Gly Tyr Ser Val Ser Ser Glu Val
            180                 185                 190

Leu Lys Val Phe Gln Asp Gln Asn Gly Gln Phe Ala Phe Ser Pro Ser
        195                 200                 205

Thr Lys Glu Arg Asp Ile Arg Thr Val Leu Asn Leu Tyr Arg Ala Ser
210                 215                 220

Phe Ile Ala Phe Pro Gly Glu Lys Val Met Glu Glu Ala Glu Ile Phe
225                 230                 235                 240

Ser Ser Arg Tyr Leu Lys Glu Ala Val Gln Lys Ile Pro Val Ser Ser
                245                 250                 255

Leu Ser Gln Glu Ile Asp Tyr Thr Leu Glu Tyr Gly Trp His Thr Asn
            260                 265                 270
```

Met Pro Arg Leu Glu Thr Arg Asn Tyr Leu Asp Val Phe Gly His Pro
275                 280                 285

Thr Ser Pro Trp Leu Lys Lys Arg Thr Gln Tyr Leu Asp Ser Glu
290                 295                 300

Lys Leu Leu Glu Leu Ala Lys Leu Glu Phe Asn Ile Phe His Ser Leu
305                 310                 315                 320

Gln Gln Lys Glu Leu Gln Tyr Leu Ser Arg Trp Trp Ile His Ser Gly
                325                 330                 335

Leu Pro Glu Leu Thr Phe Gly Arg His Arg His Val Glu Tyr Tyr Thr
                340                 345                 350

Leu Ser Ser Cys Ile Ala Thr Glu Pro Lys His Ser Ala Phe Arg Leu
                355                 360                 365

Gly Phe Ala Lys Thr Cys His Leu Ile Thr Val Leu Asp Asp Ile Tyr
370                 375                 380

Asp Thr Phe Gly Thr Met Asp Glu Ile Glu Leu Phe Asn Glu Ala Val
385                 390                 395                 400

Arg Arg Trp Asn Pro Ser Glu Lys Glu Arg Leu Pro Glu Tyr Met Lys
                405                 410                 415

Glu Ile Tyr Met Ala Leu Tyr Glu Ala Leu Thr Asp Met Ala Arg Glu
                420                 425                 430

Ala Glu Lys Thr Gln Gly Arg Asp Thr Leu Asn Tyr Ala Arg Lys Ala
                435                 440                 445

Trp Glu Val Tyr Leu Asp Ser Tyr Thr Gln Glu Ala Lys Trp Ile Ala
                450                 455                 460

Ser Gly Tyr Leu Pro Thr Phe Glu Glu Tyr Leu Glu Asn Ala Lys Val
465                 470                 475                 480

Ser Ser Gly His Arg Ala Ala Ala Leu Thr Pro Leu Leu Thr Leu Asp
                485                 490                 495

Val Pro Leu Pro Asp Asp Val Leu Lys Gly Ile Asp Phe Pro Ser Arg
                500                 505                 510

Phe Asn Asp Leu Ala Ser Ser Phe Leu Arg Leu Arg Gly Asp Thr Arg
                515                 520                 525

Cys Tyr Lys Ala Asp Arg Asp Arg Gly Glu Glu Ala Ser Ser Ile Ser
530                 535                 540

Cys Tyr Met Lys Asp Asn Pro Gly Leu Thr Glu Glu Asp Ala Leu Asn
545                 550                 555                 560

His Ile Asn Ala Met Ile Asn Asp Ile Ile Lys Glu Leu Asn Trp Glu
                565                 570                 575

Leu Leu Lys Pro Asp Ser Asn Ile Pro Met Thr Ala Arg Lys His Ala
                580                 585                 590

Tyr Glu Ile Thr Arg Ala Phe His Gln Leu Tyr Lys Tyr Arg Asp Gly
                595                 600                 605

Phe Ser Val Ala Thr Gln Glu Thr Lys Ser Leu Val Arg Arg Thr Val
610                 615                 620

Leu Glu Pro Val Pro Leu
625                 630

<210> SEQ ID NO 7
<211> LENGTH: 623
<212> TYPE: PRT
<213> ORGANISM: Picea sitchensis
<220> FEATURE:
<223> OTHER INFORMATION: spruce beta-phellandrene synthase (beta-PHLS,
      PsTPS-Phel-2, P.sitchensis2)

<400> SEQUENCE: 7

```
Met Ala Ile Val Ser Ser Val Pro Leu Ala Ser Lys Ser Cys Leu His
1               5                   10                  15

Lys Ser Leu Ile Ser Ser Ile His Lys Leu Lys Pro Phe Cys Arg Thr
            20                  25                  30

Ile Pro Thr Leu Gly Met Ser Arg Pro Gly Lys Tyr Val Met Pro Ser
            35                  40                  45

Met Ser Met Ser Ser Pro Val Ser Asp Asp Gly Val Gln Arg Arg Thr
    50                  55                  60

Gly Gly Tyr His Ser Asn Leu Trp Asn Asp Ile Ile Gln Phe Leu
65                  70                  75                  80

Ser Thr Thr Tyr Gly Glu Pro Ala Tyr Arg Glu Arg Gly Glu Arg Leu
                85                  90                  95

Ile Asp Glu Val Lys Asn Met Phe Asn Ser Ile Ser Met Glu Asp Val
                100                 105                 110

Glu Phe Ser Pro Leu Asn Asp Leu Ile Gln Arg Leu Trp Ile Val Asp
            115                 120                 125

Ser Val Glu Arg Leu Gly Ile Asp Arg His Phe Lys Asn Glu Ile Lys
        130                 135                 140

Ser Thr Leu Asp Tyr Val Tyr Ser Tyr Trp Thr Gln Lys Gly Ile Gly
145                 150                 155                 160

Cys Gly Ile Glu Ser Val Val Pro Asp Leu Asn Ser Thr Ala Leu Gly
                165                 170                 175

Leu Arg Thr Leu Arg Leu His Gly Tyr Pro Val Ser Ala Glu Val Leu
            180                 185                 190

Lys His Phe Gln Asn Gln Asn Gly Gln Phe Ala Cys Ser Pro Ser Glu
        195                 200                 205

Thr Glu Gly Glu Met Arg Ser Ile Val Asn Leu Tyr Arg Ala Ser Leu
    210                 215                 220

Ile Ala Phe Pro Gly Glu Lys Val Met Glu Glu Ala Glu Ile Phe Ser
225                 230                 235                 240

Thr Lys Tyr Leu Lys Glu Ala Leu Gln Lys Ile Pro Val Ser Ser Leu
                245                 250                 255

Ser Arg Glu Ile Gly Asp Val Leu Glu Gln Asp Trp His Thr Asn Leu
            260                 265                 270

Pro Arg Leu Glu Ala Arg Asn Tyr Ile Asp Val Phe Gly Gln Asp Thr
        275                 280                 285

Lys Asp Thr Lys Leu Tyr Met Lys Thr Glu Lys Leu Leu Glu Leu Ala
    290                 295                 300

Lys Leu Glu Phe Asn Ile Phe Gln Ser Leu Gln Lys Thr Glu Leu Asp
305                 310                 315                 320

Ser Leu Leu Arg Trp Trp Lys Asp Ser Gly Phe His His Ile Thr Phe
                325                 330                 335

Ser Arg His Leu His Val Glu Tyr Tyr Thr Leu Ala Ser Cys Ile Ala
            340                 345                 350

Ile Glu Pro Gln His Ser Arg Phe Arg Leu Gly Phe Ala Lys Ala Cys
        355                 360                 365

His Val Ile Thr Ile Leu Asp Asp Met Tyr Asp Val Phe Gly Thr Ile
    370                 375                 380

Asp Glu Leu Glu Leu Phe Thr Ala Gln Ile Lys Arg Trp Asp Pro Ser
385                 390                 395                 400

Ala Thr Asp Cys Leu Pro Lys Tyr Met Lys Arg Met Tyr Met Ile Leu
                405                 410                 415
```

```
Tyr Asp Met Val Asn Glu Met Ser Arg Glu Ala Glu Thr Ala Gln Gly
            420                 425                 430

Arg Asp Thr Leu Asn Tyr Ala Arg Gln Ala Trp Glu Asp Phe Ile Asp
        435                 440                 445

Ser Tyr Met Gln Glu Ala Lys Trp Ile Ala Thr Gly Tyr Leu Pro Thr
    450                 455                 460

Phe Asp Glu Tyr Phe Glu Asn Gly Lys Val Ser Ser Gly His Arg Val
465                 470                 475                 480

Ala Ala Leu Gln Pro Ile Leu Thr Met Asp Ile Pro Phe Pro His Asp
                485                 490                 495

Ile Leu Lys Glu Val Asp Phe Pro Ser Lys Leu Asn Asp Leu Ala Ser
            500                 505                 510

Ala Ile Leu Arg Leu Arg Gly Asp Thr Arg Cys Tyr Lys Ala Asp Arg
        515                 520                 525

Ala Arg Gly Glu Glu Ala Ser Cys Ile Ser Cys Tyr Met Lys Asp Asn
    530                 535                 540

Pro Gly Ala Thr Glu Glu Asp Ala Leu Ser His Ile Asn Ala Val Ile
545                 550                 555                 560

Ser Asp Val Ile Lys Gly Leu Asn Trp Glu Leu Leu Asn Pro Asn Ser
                565                 570                 575

Ser Val Pro Ile Ser Ser Lys Lys His Val Phe Asp Val Ser Arg Ala
            580                 585                 590

Leu His Tyr Gly Tyr Lys Tyr Arg Asp Gly Tyr Ser Val Ser Asn Ile
        595                 600                 605

Glu Thr Lys Ser Leu Val Met Arg Thr Leu Leu Glu Ser Val Pro
    610                 615                 620

<210> SEQ ID NO 8
<211> LENGTH: 624
<212> TYPE: PRT
<213> ORGANISM: Picea sitchensis
<220> FEATURE:
<223> OTHER INFORMATION: spruce beta-phellandrene synthase (beta-PHLS,
      PsTPS-Phel-3, P.sitchensis3)

<400> SEQUENCE: 8

Met Ala Ile Val Ser Ser Val Pro Leu Ala Ser Lys Ser Cys Leu His
1               5                   10                  15

Lys Ser Leu Ile Ser Ser Ile His Lys Leu Lys Pro Phe Cys Arg Thr
            20                  25                  30

Ile Pro Thr Leu Gly Met Ser Arg Pro Gly Lys Tyr Val Met Pro Ser
        35                  40                  45

Met Ser Met Ser Ser Pro Val Ser Asp Asp Gly Val Gln Arg Arg Thr
    50                  55                  60

Gly Gly Tyr His Ser Asn Leu Trp Asn Asp Asp Ile Ile Gln Phe Leu
65                  70                  75                  80

Ser Thr Pro Tyr Gly Glu Pro Ala Tyr Arg Glu Arg Gly Glu Arg Leu
                85                  90                  95

Ile Asp Glu Val Lys Asn Met Phe Asn Ser Ile Ser Met Glu Asp Val
            100                 105                 110

Glu Phe Ser Pro Leu Asn Asp Leu Ile Gln Arg Leu Trp Ile Val Asp
        115                 120                 125

Ser Val Glu Arg Leu Gly Ile Asp Arg His Phe Lys Asn Glu Ile Lys
    130                 135                 140

Ser Thr Leu Asp Tyr Val Tyr Ser Tyr Trp Thr Gln Lys Gly Ile Gly
```

```
                145                 150                 155                 160
        Cys Gly Ile Glu Ser Val Asp Pro Asp Leu Asn Ser Thr Ala Leu Gly
                        165                 170                 175

Leu Arg Thr Leu Arg Leu His Gly Tyr Pro Val Ser Ala Glu Val Leu
                        180                 185                 190

Lys His Phe Gln Asn Gln Asn Gly Gln Phe Ala Cys Ser Pro Ser Glu
                        195                 200                 205

Thr Glu Gly Glu Met Arg Ser Ile Val Asn Leu Tyr Arg Ala Ser Leu
                        210                 215                 220

Ile Ala Phe Pro Gly Glu Lys Val Met Glu Glu Ala Glu Ile Phe Ser
        225                 230                 235                 240

Thr Lys Tyr Leu Lys Glu Ala Leu Gln Lys Ile Pro Val Ser Ser Leu
                        245                 250                 255

Ser Arg Glu Ile Gly Asp Val Leu Glu Gln Asp Trp His Thr Asn Leu
                        260                 265                 270

Pro Arg Leu Glu Ala Arg Asn Tyr Ile Asp Val Phe Gly Gln Asp Thr
                        275                 280                 285

Lys Asp Thr Lys Leu Tyr Met Lys Thr Glu Lys Leu Leu Glu Leu Ala
                        290                 295                 300

Lys Leu Glu Phe Asn Ile Phe Gln Ser Leu Gln Lys Thr Glu Leu Asp
        305                 310                 315                 320

Ser Leu Leu Arg Trp Trp Lys Asp Ser Gly Phe His His Ile Thr Phe
                        325                 330                 335

Ser Arg His Leu His Val Glu Tyr Tyr Thr Leu Ala Ser Cys Ile Ala
                        340                 345                 350

Ile Glu Pro Gln His Ser Arg Phe Arg Leu Gly Phe Ala Lys Ala Cys
                        355                 360                 365

His Val Ile Thr Ile Leu Asp Asp Met Tyr Asp Val Phe Gly Thr Ile
                        370                 375                 380

Asp Glu Leu Glu Leu Phe Thr Ala Gln Ile Lys Arg Trp Asp Pro Ser
        385                 390                 395                 400

Ala Thr Asp Cys Leu Pro Lys Tyr Met Lys Arg Met Tyr Met Ile Leu
                        405                 410                 415

Tyr Asp Met Val Asn Glu Met Ser Arg Glu Ala Glu Thr Ala Gln Gly
                        420                 425                 430

Arg Asp Thr Leu Asn Tyr Ala Arg Gln Ala Trp Glu Asp Phe Ile Asp
                        435                 440                 445

Ser Tyr Met Gln Glu Ala Lys Trp Ile Ala Thr Gly Tyr Leu Pro Thr
                        450                 455                 460

Phe Asp Glu Tyr Phe Glu Asn Gly Lys Val Ser Ser Gly His Arg Val
        465                 470                 475                 480

Ala Ala Leu Gln Pro Ile Leu Thr Met Asp Ile Pro Phe Pro His Asp
                        485                 490                 495

Ile Leu Lys Glu Val Asp Phe Pro Ser Lys Leu Asn Asp Leu Ala Ser
                        500                 505                 510

Ala Ile Leu Arg Leu Arg Gly Asp Thr Arg Cys Tyr Lys Ala Asp Arg
                        515                 520                 525

Ala Arg Gly Glu Glu Ala Ser Cys Ile Ser Cys Tyr Met Lys Asp Asn
                        530                 535                 540

Pro Gly Ala Thr Glu Glu Asp Ala Leu Ser His Ile Asn Ala Val Ile
        545                 550                 555                 560

Ser Asp Val Ile Lys Gly Leu Asn Trp Glu Leu Leu Asn Pro Asn Ser
                        565                 570                 575
```

```
Ser Val Pro Ile Ser Ser Lys Lys His Val Phe Asp Val Ser Arg Ala
                580                 585                 590

Leu His Tyr Gly Tyr Lys Tyr Arg Asp Gly Tyr Ser Val Ser Asn Ile
                595                 600                 605

Glu Thr Lys Ser Leu Val Met Arg Thr Leu Leu Glu Ser Val Pro Phe
                610                 615                 620

<210> SEQ ID NO 9
<211> LENGTH: 624
<212> TYPE: PRT
<213> ORGANISM: Picea sitchensis
<220> FEATURE:
<223> OTHER INFORMATION: spruce beta-phellandrene synthase (beta-PHLS,
      PsTPS-Phel-1, P.sitchensis1)

<400> SEQUENCE: 9

Met Ala Ile Val Ser Ser Val Pro Leu Ala Ser Lys Ser Cys Leu His
1               5                   10                  15

Lys Ser Leu Ile Ser Ser Ile His Lys Leu Lys Pro Phe Cys Arg Thr
                20                  25                  30

Ile Pro Thr Leu Gly Met Ser Arg Pro Gly Lys Tyr Val Met Pro Ser
                35                  40                  45

Met Ser Met Ser Ser Pro Val Ser Asp Asp Gly Val Gln Arg Arg Thr
    50                  55                  60

Gly Gly Tyr His Ser Asn Leu Trp Asn Asp Asp Ile Ile Gln Phe Leu
65                  70                  75                  80

Ser Thr Pro Tyr Gly Glu Pro Ala Tyr Arg Glu Arg Gly Glu Arg Leu
                85                  90                  95

Ile Asp Glu Val Lys Asn Met Phe Asn Ser Ile Ser Met Glu Asp Val
                100                 105                 110

Glu Phe Ser Pro Leu Asn Asp Leu Ile Gln Arg Leu Trp Ile Val Asp
                115                 120                 125

Ser Val Glu Arg Leu Gly Ile Asp Arg His Phe Lys Asn Glu Ile Lys
    130                 135                 140

Ser Thr Leu Asp Tyr Val Tyr Ser Tyr Trp Thr Gln Lys Gly Ile Gly
145                 150                 155                 160

Cys Gly Ile Glu Ser Val Val Pro Asp Leu Asn Ser Thr Ala Leu Gly
                165                 170                 175

Leu Arg Thr Leu Arg Leu His Gly Tyr Pro Val Ser Ala Glu Val Leu
                180                 185                 190

Lys His Phe Gln Asn Gln Asn Gly Gln Phe Ala Cys Ser Pro Ser Glu
                195                 200                 205

Thr Glu Gly Glu Met Arg Ser Ile Val Asn Leu Tyr Arg Ala Ser Leu
    210                 215                 220

Ile Ala Phe Pro Gly Glu Lys Val Met Glu Glu Ala Glu Ile Phe Ser
225                 230                 235                 240

Thr Lys Tyr Leu Lys Glu Ala Leu Gln Lys Ile Pro Val Ser Ser Leu
                245                 250                 255

Ser Arg Glu Ile Gly Asp Val Leu Glu Gln Asp Trp His Thr Asn Leu
                260                 265                 270

Pro Arg Leu Glu Ala Arg Asn Tyr Ile Asp Val Phe Gly Gln Asp Thr
                275                 280                 285

Lys Asp Thr Lys Leu Tyr Met Lys Thr Glu Lys Leu Leu Glu Leu Ala
    290                 295                 300

Lys Leu Glu Phe Asn Ile Phe Gln Ser Leu Gln Lys Thr Glu Leu Asp
```

305                 310                 315                 320
        Ser Leu Leu Arg Trp Trp Lys Asp Ser Gly Phe Pro His Ile Thr Phe
                        325                 330                 335

Ser Arg His Leu His Val Glu Tyr Tyr Thr Leu Ala Ser Cys Ile Ala
                        340                 345                 350

Phe Glu Pro Gln His Ser Arg Phe Arg Leu Gly Phe Ala Lys Ala Cys
                        355                 360                 365

His Val Ile Thr Ile Leu Asp Asp Met Tyr Asp Val Phe Gly Thr Ile
                370                 375                 380

Asp Glu Leu Glu Leu Phe Thr Ala Gln Ile Lys Arg Trp Asp Pro Ser
        385                 390                 395                 400

Ala Thr Asp Cys Leu Pro Lys Tyr Met Lys Arg Met Tyr Met Ile Leu
                        405                 410                 415

Tyr Asp Met Val Asn Glu Met Ser Arg Glu Ala Glu Thr Ala Gln Gly
                        420                 425                 430

Arg Asp Thr Leu Asn Tyr Ala Arg Gln Ala Trp Glu Asp Phe Ile Asp
                        435                 440                 445

Ser Tyr Met Gln Glu Ala Lys Trp Ile Ala Thr Gly Tyr Leu Pro Thr
                450                 455                 460

Phe Asp Glu Tyr Phe Glu Asn Gly Lys Val Ser Ser Gly His Arg Val
        465                 470                 475                 480

Ala Ala Leu Gln Pro Ile Leu Thr Met Asp Ile Pro Phe Pro His Asp
                        485                 490                 495

Ile Leu Lys Glu Val Asp Phe Pro Ser Lys Leu Asn Asp Leu Ala Ser
                        500                 505                 510

Ala Ile Leu Arg Leu Arg Gly Asp Thr Arg Cys Tyr Lys Ala Asp Arg
                        515                 520                 525

Ala Arg Gly Glu Glu Ala Ser Cys Ile Ser Cys Tyr Met Lys Asp Asn
                530                 535                 540

Pro Gly Ala Thr Glu Glu Asp Ala Leu Ser His Ile Asn Ala Val Ile
        545                 550                 555                 560

Ser Asp Val Ile Lys Gly Leu Asn Trp Glu Leu Leu Asn Pro Asn Ser
                        565                 570                 575

Ser Val Pro Ile Ser Ser Lys Lys His Val Phe Asp Val Ser Arg Ala
                        580                 585                 590

Leu His Tyr Gly Tyr Lys Tyr Arg Asp Gly Tyr Ser Val Ser Asn Ile
                        595                 600                 605

Glu Thr Lys Ser Leu Val Met Arg Thr Leu Leu Glu Ser Val Pro Phe
        610                 615                 620

<210> SEQ ID NO 10
<211> LENGTH: 624
<212> TYPE: PRT
<213> ORGANISM: Picea sitchensis
<220> FEATURE:
<223> OTHER INFORMATION: spruce beta-phellandrene synthase (beta-PHLS,
      PsTPS-Phel-4, P.sitchensis4)

<400> SEQUENCE: 10

Met Ala Ile Val Ser Ser Val Pro Leu Ala Ser Lys Ser Cys Leu His
        1               5                   10                  15

Lys Ser Leu Ile Ser Ser Ile His Lys Leu Lys Pro Phe Cys Arg Thr
                        20                  25                  30

Ile Pro Thr Leu Gly Met Ser Arg Pro Gly Lys Ser Val Met Pro Ser
                        35                  40                  45

```
Met Ser Met Ser Ser Pro Val Ser Asp Asp Gly Val Gln Arg Arg Thr
 50                  55                  60
Gly Gly Tyr His Ser Asn Leu Trp Asn Asp Ile Ile Gln Phe Leu
 65              70                  75                  80
Ser Thr Pro Tyr Gly Glu Pro Ala Tyr Arg Glu Arg Gly Glu Arg Leu
                 85                  90                  95
Ile Asp Glu Val Lys Asn Met Phe Asn Ser Ile Ser Met Glu Asp Val
             100                 105                 110
Glu Phe Ser Pro Leu Asn Asp Leu Ile Gln Arg Leu Trp Ile Val Asp
         115                 120                 125
Ser Val Glu Arg Leu Gly Ile Asp Arg His Phe Lys Asn Glu Ile Lys
 130                 135                 140
Ser Thr Leu Asp Tyr Val Tyr Ser Tyr Trp Thr Gln Lys Gly Ile Gly
 145             150                 155                 160
Cys Gly Ile Glu Ser Val Val Pro Asp Leu Asn Ser Thr Ala Leu Gly
             165                 170                 175
Leu Arg Thr Leu Arg Leu His Gly Tyr Pro Val Ser Ala Glu Val Leu
         180                 185                 190
Lys His Phe Gln Asn Gln Asn Gly Gln Phe Ala Cys Ser Pro Ser Glu
         195                 200                 205
Thr Glu Gly Glu Met Arg Ser Ile Val Asn Leu Tyr Arg Ala Ser Leu
 210                 215                 220
Ile Ala Phe Pro Gly Glu Lys Val Met Glu Glu Ala Glu Ile Phe Ser
225                 230                 235                 240
Thr Lys Tyr Leu Lys Glu Ala Leu Gln Lys Ile Pro Val Ser Ser Leu
             245                 250                 255
Ser Arg Glu Ile Gly Asp Val Leu Glu Gln Asp Trp His Thr Asn Leu
         260                 265                 270
Pro Arg Leu Glu Ala Arg Asn Tyr Ile Asp Val Phe Gly Gln Asp Thr
         275                 280                 285
Lys Asp Thr Lys Leu Tyr Met Lys Thr Glu Lys Leu Leu Glu Leu Ala
 290                 295                 300
Lys Leu Glu Phe Asn Ile Phe Gln Ser Leu Gln Lys Thr Glu Leu Asp
305                 310                 315                 320
Ser Leu Leu Arg Trp Trp Lys Asp Ser Gly Phe His His Ile Thr Phe
                 325                 330                 335
Ser Arg His Leu His Val Glu Tyr Tyr Thr Leu Ala Ser Cys Ile Ala
             340                 345                 350
Phe Glu Pro Gln His Ser Arg Phe Arg Leu Gly Phe Ala Lys Ala Cys
         355                 360                 365
His Val Ile Thr Ile Leu Asp Asp Met Tyr Asp Val Phe Gly Thr Ile
         370                 375                 380
Asp Glu Leu Glu Leu Phe Thr Ala Gln Ile Lys Arg Trp Asp Pro Ser
385                 390                 395                 400
Ala Thr Asp Cys Leu Pro Lys Tyr Met Lys Arg Met Tyr Met Ile Leu
             405                 410                 415
Tyr Asp Met Val Asn Glu Met Ser Arg Glu Ala Glu Thr Ala Gln Gly
             420                 425                 430
Arg Asp Thr Leu Asn Tyr Ala Arg Gln Ala Trp Glu Asp Phe Ile Asp
         435                 440                 445
Ser Tyr Met Gln Glu Ala Lys Trp Ile Ala Thr Gly Tyr Leu Pro Thr
 450                 455                 460
Phe Asp Glu Tyr Phe Glu Asn Gly Lys Val Ser Ser Gly His Arg Val
```

```
            465                 470                 475                 480
Ala Ala Leu Gln Pro Ile Leu Thr Met Asp Ile Pro Phe Pro His Asp
                    485                 490                 495

Ile Leu Lys Glu Val Asp Phe Pro Ser Lys Leu Asn Asp Leu Ala Ser
                500                 505                 510

Ala Ile Leu Arg Leu Arg Gly Asp Thr Arg Cys Tyr Lys Ala Asp Arg
            515                 520                 525

Ala Arg Gly Glu Glu Ala Ser Cys Ile Ser Cys Tyr Met Lys Asp Asn
        530                 535                 540

Pro Gly Ala Thr Glu Glu Asp Ala Leu Ser His Ile Asn Ala Val Ile
545                 550                 555                 560

Asn Asp Val Ile Lys Gly Leu Asn Trp Glu Leu Leu Asn Pro Asn Ser
                565                 570                 575

Ser Val Pro Ile Ser Ser Lys Lys His Val Phe Asp Val Ser Arg Ala
            580                 585                 590

Leu His Tyr Gly Tyr Lys Tyr Arg Asp Gly Tyr Ser Val Ser Asn Ile
        595                 600                 605

Glu Thr Lys Ser Leu Val Met Arg Thr Leu Leu Glu Ser Val Pro Phe
610                 615                 620

<210> SEQ ID NO 11
<211> LENGTH: 10
<212> TYPE: PRT
<213> ORGANISM: Artificial Sequence
<220> FEATURE:
<223> OTHER INFORMATION: synthetic beta-phellandrine synthase
      (beta-PHLS) partially conserved amino acid sequence with
      role in catalysis

<400> SEQUENCE: 11

Leu Gln Leu Tyr Glu Ala Ser Phe Leu Leu
1               5                   10

<210> SEQ ID NO 12
<211> LENGTH: 20
<212> TYPE: DNA
<213> ORGANISM: Artificial Sequence
<220> FEATURE:
<223> OTHER INFORMATION: synthetic PCR amplification primer PHLS_F
      for Syn-beta-PHLS

<400> SEQUENCE: 12
cctgggcggt tctgataacg                                              20

<210> SEQ ID NO 13
<211> LENGTH: 29
<212> TYPE: DNA
<213> ORGANISM: Artificial Sequence
<220> FEATURE:
<223> OTHER INFORMATION: synthetic PCR amplification primer
      PHLS_BamHI_R for Syn-beta-PHLS

<400> SEQUENCE: 13
cgcggatcct tttgacggcg gccgcagat                                    29

<210> SEQ ID NO 14
<211> LENGTH: 41
<212> TYPE: DNA
<213> ORGANISM: Artificial Sequence
<220> FEATURE:
<223> OTHER INFORMATION: synthetic PCR amplification primer
      CamR_NotI_F for chloramphenicol resistance cassette from
      plasmid pACYC184
```

```
<400> SEQUENCE: 14
aaggaaaaaa gcggccgcgt tgatcggcac gtaagaggtt c                   41

<210> SEQ ID NO 15
<211> LENGTH: 34
<212> TYPE: DNA
<213> ORGANISM: Artificial Sequence
<220> FEATURE:
<223> OTHER INFORMATION: synthetic PCR amplification primer
      CamR_BamHI_R for chloramphenicol resistance cassette from plasmid
      pACYC184

<400> SEQUENCE: 15
cgcggatccc caggcgttta agggcaccaa taac                           34

<210> SEQ ID NO 16
<211> LENGTH: 22
<212> TYPE: DNA
<213> ORGANISM: Artificial Sequence
<220> FEATURE:
<223> OTHER INFORMATION: synthetic genomic DNA PCR primer A2us_F for
      PsbA2 homologous recombination

<400> SEQUENCE: 16
tatcagaatc cttgcccaga tg                                        22

<210> SEQ ID NO 17
<211> LENGTH: 20
<212> TYPE: DNA
<213> ORGANISM: Artificial Sequence
<220> FEATURE:
<223> OTHER INFORMATION: synthetic genomic DNA PCR primer A2ds_R for
      PsbA2 homologous recombination

<400> SEQUENCE: 17
ggtagagttg cgagggcaat                                           20

<210> SEQ ID NO 18
<211> LENGTH: 34
<212> TYPE: DNA
<213> ORGANISM: Artificial Sequence
<220> FEATURE:
<223> OTHER INFORMATION: synthetic PCR amplification forward primer
      for codon-optimized beta-PHLS gene (S-beta-PHLS)

<400> SEQUENCE: 18
ggaattccat atgtgtagtt tgcaagtttc tgat                           34

<210> SEQ ID NO 19
<211> LENGTH: 33
<212> TYPE: DNA
<213> ORGANISM: Artificial Sequence
<220> FEATURE:
<223> OTHER INFORMATION: synthetic PCR amplification reverse primer
      for codon-optimized beta-PHLS gene (S-beta-PHLS)

<400> SEQUENCE: 19
acaggatcct cactcatagc gctcaatcag cgt                            33

<210> SEQ ID NO 20
<211> LENGTH: 6
<212> TYPE: PRT
<213> ORGANISM: Artificial Sequence
<220> FEATURE:
<223> OTHER INFORMATION: synthetic 6xHis tag
```

```
<400> SEQUENCE: 20

His His His His His His
1               5
```

PRODUCTION OF β-PHELLANDRENE USING GENETICALLY ENGINEERED PHOTOSYNTHETIC MICROORGAMISMS

CROSS-REFERENCE TO RELATED APPLICATIONS

This application is a division of U.S. application Ser. No. 14/376,392, filed Aug. 1, 2014, which is a National Stage of International Application No. PCT/US2013/024908, filed Feb. 6, 2013, and which claims the benefit to U.S. Provisional Application No. 61/595,610, filed Feb. 6, 2012, each of which is herein incorporated by reference for all purposes.

REFERENCE TO SEQUENCE LISTING SUBMITTED AS AN ASCII TEXT FILE

This application includes a Sequence Listing submitted as a text file named "086540-1073872-SEQ.txt" created Feb. 4, 2018, and containing 53,248 bytes. The material contained in this text file is incorporated by reference in its entirety for all purposes.

BACKGROUND OF THE INVENTION

There is a need to develop renewable biofuels and chemicals that will help meet global demands for energy and synthetic chemistry feedstock, but without contributing to climate change or other environmental degradation.

Terpenoids represent the largest and most diverse group of naturally occurring organic compounds, and are all derived from the monomeric isoprene five-carbon building block. More than 25,000 different naturally occurring terpenoids have been identified, and many have plant origin. Terpenoids are classified into groups based on the number of five-carbon isoprene units they comprise; monoterpenes (C10), sesquiterpenes (C15), diterpenes (C20), triterpenes (C30), tetraterpenes (C40) and polyterpenes (greater than C40). β-Phellandrene ($C_{10}H_{16}$) offers example of such monoterpenes as a constituent of the essential oils synthesized by many plant species. It has significant commercial potential for use in the cosmetics and personal care industries, in cleaning products for household and industrial use, and medicinal use. There is also potential for β-phellandrene and other monoterpenes to be developed as feedstock in the synthetic chemistry and pharmaceutical industries, and as a renewable biofuel, where β-phellandrene itself may serve as supplement to gasoline or oligomerization of such monoterpene units may generate second order fuel molecules, suitable for use as supplements to jet fuel and diesel.

A number of plant species naturally produce β-phellandrene as a constituent of their essential oils, including lavender and grand fir. Essential oils are produced and stored in specialized organs called glandular trichomes, which form on the surface of leaves and flowers. Essential oils are mainly composed of monoterpenes and function in chemical defense against potential herbivores. The harvesting of essential oils from glandular trichomes, and subsequent purification of individual monoterpenes, such as β-phellandrene, is labour intensive and costly with relatively limited yields. The use of microorganisms, both photosynthetic and non-photosynthetic, for the production of such commercially useful and valuable chemicals is an attractive alternative to harvesting the product from plants.

All terpenoids are produced by two biosynthetic pathways: 1) the mevalonic acid (MVA) pathway, which operates in the cytosol of eukaryotes and archaea; and 2) the methyl-erythritol-4-phosphate (MEP) pathway, which is of prokaryotic bacterial origin and present in cyanobacteria, as well as in plant and algal plastids (see, FIG. 1). Synthesis of β-phellandrene in plants is due to the presence of a β-phellandrene synthase (β-PHLS) gene. This is a nuclear gene encoding a chloroplast-localized protein that catalyzes the conversion of geranyl diphosphate (GPP) to β-phellandrene. Plant β-phellandrene synthases, encoded by the gene β-PHLS, have been cloned and characterized from lavender, grand fir, tomato, and spruce (see, e.g., Demissie et al., *Planta,* 233:685-696 (2011); Bohlmann et al., *Arch. Biochem. Biophys.,* 368:232-243 (1994); Schilmiller et al., *Proc. Nat. Acad. Sci. U.S.A.,* 106:10865-10870 (2009); and Keeling et al., *BMC Plant Biol.* 11:43-57 (2011)).

Although photosynthetic microorganisms, such as microalgae and cyanobacteria utilize the MEP pathway, which generates GPP precursors, these microorganisms do not natively possess a β-phellandrene synthase gene or enzyme and thus, do not natively catalyze the conversion of GPP to β-phellandrene. However, they do express the MEP pathway and utilize the corresponding isoprenoid pathway enzymes for the biosynthesis of a great variety of needed terpenoid-type molecules like carotenoids, tocopherols, phytol, sterols, hormones, among many others) (see, FIG. 1). The MEP isoprenoid biosynthetic pathway (Lindberg et al., *Metab Eng.,* 12:70-79 (2010)) consumes pyruvate and glyceraldehyde-3-phosphate (G3P) as substrates, which are combined to form deoxyxylulose-5-phosphate (DXP), as first described for *Escherichia coli* (Rohmer et al., *Biochem.* 1, 295:517-524 (1993)). DXP is then converted into methylerythritol phosphate (MEP), which is subsequently modified to form hydroxy-2-methyl-2-butenyl-4-diphosphate (HMBPP). HMBPP is the substrate required for the formation of isopentenyl pyrophosphate (IPP) and dimethylallyl pyrophosphate (DMAPP), which are terpenoid precursors. Cyanobacteria also contain an IPP isomerase that catalyzes the inter-conversion of IPP and DMAPP. In addition to reactants G3P and pyruvate, the MEP pathway consumes reducing equivalents and cellular energy in the form of NADPH, reduced ferredoxin, CTP and ATP, ultimately derived from photosynthesis. For reviews, see also (Ershov et al., *J. Bacteriol.* 184(18):5045-51; Sharkey et al., *Ann. Bot.* 101(1):5-18 (2002)).

Evidence in the literature shows that 15-carbon hydrophobic terpenoid hydrocarbons can be transgenically expressed in photosynthetic and fermentative microorganisms, but are trapped within the cell, where they are synthesized, requiring dewatering of the culture, drying of the biomass, followed by product extraction from within the cells. For example, the sesquiterpene β-caryophyllene was produced in a transgenic strain of the cyanobacterium *Synechocystis*. However, isolation of the product required an extensive protocol that included treating the isolated cellular biomass with an application of a chloroform:methanol:water solvent mixture to solubilize lipid bilayers, releasing all intracellular compounds, and extracting the lipophilic components (Reinsvold et al., *J. Plant Physiol.,* 168: 848-852 (2011)).

Ten-carbon monoterpene hydrocarbon products occur in different distinct configurations, such as acyclic (e.g., myrcene), monocyclic (e.g., limonene and β-phellandrene), and bicyclic molecules (e.g., pinene). Spontaneous emission of monoterpene hydrocarbons from single-celled microorganisms to the extracellular space depends on the chemical nature of the monoterpene, and also depends on the lipid bilayer configuration and cell wall hydrophobic barriers imposed by the microorganism. For example, yield of limonene production increased substantially in transgenic *E. coli* upon the additional heterologous expression of an efflux pump from *Alcanivorax borkumensis* (AcrB/AcrD/AcrFa gene product; GenBank Accession No. YP692684) in the cell, suggesting limonene product feedback inhibition and/or toxicity to the cell.

The *Lavandula angustifolia* β-phellandrene synthase protein has been over-expressed in *E. coli* upon transformant cell induction with isopropyl β-D-1-thiogalactopyranoside, IPTG (Demissie et al., *Planta*, 233:685-696, 2011). However, IPTG induction in *E. coli* can be toxic to the cell, causing loss of cell fitness, thereby hindering a continuous and large scale production of β-phellandrene synthase by this method. Host cell toxicity could be due to accumulation of the recombinant protein itself and/or due to synthesis and intracellular accumulation of the transgenic product. The latter is one of the most common barriers in the commercial application of synthetic biology approaches for product generation.

This invention in based, in part, on the discovery of nucleic acids and expression systems that can be introduced and expressed in cyanobacteria and enable these microorganisms to produce β-phellandrene. Such genetically modified cyanobacteria can be used commercially in an enclosed mass culture system to provide a source of β-phellandrene which can be potentially developed as feedstock in the synthetic chemistry and pharmaceutical industries. For instance, β-phellandrene may serve as supplement to gasoline or oligomerization of such monoterpene units may generate second order fuel molecules, suitable for use as supplements to jet fuel and diesel.

BRIEF SUMMARY OF THE INVENTION

The current invention addresses the need of generating monoterpene hydrocarbons by providing methods and composition for the generation of β-phellandrene hydrocarbons in photosynthetic microorganisms, e.g. cyanobacteria and microalgae. β-Phellandrene, derived entirely via photosynthesis, i.e., from sunlight, carbon dioxide ($CO_2$) and water ($H_2O$), could serve as renewable biofuels or feedstock in the synthetic chemistry and pharmaceutical industries.

The invention is based, in part, on the discovery of improvements to the engineering of cyanobacteria which, upon suitable modification, produce 10-carbon monoterpenes, such as β-phellandrene. In one aspect, the invention therefore provides methods and compositions for producing and harvesting β-phellandrene from cyanobacteria. Such genetically modified organisms can be used commercially in an enclosed mass culture system, e.g., a photobioreactor, to provide a source of renewable fuel for internal combustion engines or, upon on-board reformation, in fuel-cell operated engines; or to provide a source of β-phellandrene for use in chemical processes such as chemical synthesis, pharmaceuticals and perfume cosmetics.

Photosynthetic microorganisms, such as microalgae and cyanobacteria do not possess a β-phellandrene synthase gene or enzyme by which to catalyze the formation of β-phellandrene from GPP. However, they do express the methyl-erythritol-4-phosphate (MEP) pathway and utilize the corresponding isoprenoid pathway enzymes for the biosynthesis of a variety of terpenoid-type molecules. This invention provides methods and compositions to genetically modify microorganisms to express a β-phellandrene synthase gene, e.g., a codon-optimized *Lavandular angustifolia* β-phellandrene synthase gene, in order to produce β-phellandrene in cyanobacteria.

In one aspect, the invention provides a method of producing β-phellandrene hydrocarbons in cyanobacteria, the method comprising: introducing an expression cassette that comprises a nucleic acid encoding β-phellandrene synthase into the cyanobacteria, wherein the nucleic acid encoding β-phellandrene synthase is operatively linked to a PsbA2 promoter, or other suitable promoter; and culturing the cyanobacteria under conditions in which the nucleic acid encoding β-phellandrene synthase is expressed. In some embodiments, the expression cassette is introduced into the PsbA2 gene locus and the PsbA2 promoter is the native cyanobacteria promoter. In some embodiments, the cyanobacteria are unicellular cyanobacteria, e.g., a *Synechocystis* sp or a *Synechococcus* sp. In alternative embodiments, the cyanobacteria are multicellular, e.g., a *Gloeocapsa* sp. The multicellular cyanobacteria may be a filamentous cyanobacteria sp. such as a *Nostoc* sp, an *Anabaena* sp, or an *Arthrospira* sp. In some embodiments, the nucleic acid encodes a β-phellandrene synthase that has at least 55%, 60%, 70%, 75%, or 80% sequence identity, often at least 85%, 90%, 95%, or 100% sequence identity, to SEQ ID NO:3. In some embodiments, the nucleic acid encodes a β-phellandrene synthase that comprises amino acid SEQ ID NO:1. In typical embodiments, the nucleic acid that encodes the β-phellandrene synthase is codon-adjusted for expression in cyanobacteria, e.g., in some embodiments, the nucleic acid is a codon-modified variant of SEQ ID NO:2. In some embodiments, the β-phellandrene synthase nucleic acid comprises SEQ ID NO:3, or a sequence having at least 80% identity, typically at least 85% identity or 90%, 95%, 96%, 97%, 98%, 99%, or 100% identity to the nucleic acid sequence of SEQ ID NO:3.

In other aspects, the invention provides a cyanobacteria cell, wherein the cyanobacteria cell comprises a heterologous nucleic acid that encodes β-phellandrene synthase and is operably linked to a promoter such as a PsbA2 promoter. In some embodiments, the PsbA2 promoter is an endogenous promoter. In some embodiments, the cyanobacteria are unicellular cyanobacteria, e.g., a *Synechocystis* sp or a *Synechococcus* sp. In alternative embodiments, the cyanobacteria are multicellular cyanobacteria, e.g., a *Gloeocapsa* sp. In some embodiments, the multicellular cyanobacteria sp is a filamentous cyanobacteria sp. such as a *Nostoc* sp, an *Anabaena* sp, or an *Arthrospira* sp. In some embodiments, the heterologous nucleic acid encodes a β-phellandrene synthase and has at least 55%, 60%, 70%, 75%, or 80% sequence identity, often at least 85%, 90%, 95%, or 100% sequence identity, to the nucleic acid sequence of SEQ ID NO:3. In some embodiments, the cyanobacteria cell comprises a heterologous nucleic acid that comprises the nucleic acid sequence of SEQ ID NO:3. Preferably, the heterologous nucleic acid present in the cyanobacterial cell that encodes the β-phellandrene synthase is codon-optimized for expression in cyanobacteria, e.g., in some embodiments, the nucleic acid is a codon-optimized variant of SEQ ID NO:2. In some embodiments, the β-phellandrene synthase nucleic acid comprises SEQ ID NO:3, or a sequence having at least 70%, 75%, 80%, 85%, 90%, 95%, 96%, 97%, 98%, 99%, or 100% identity to SEQ ID NO:3. The invention additionally provides vectors comprising the nucleic acid and cyanobacterial host cells into which the nucleic acid has been introduced.

In a further aspect, the invention provides a nucleic acid encoding a β-phellandrene synthase that comprises amino acid SEQ ID NO:1, where the nucleic acid is a codon-optimized variant of SEQ ID NO:2 where codons used with an average frequency of less than 12% by *Synechocystis* are replaced by more frequently used codons. In some embodiments, the nucleic acid comprises the sequence set forth in SEQ ID NO:3, or a sequence having at least 80%, 85%, 90%, 95%, 96%, 97%, 98%, 99%, or 100% identity to SEQ ID NO:3. The invention additionally provides vectors comprising the nucleic acid and cyanobacterial host cells into which the nucleic acid has been introduced.

In another aspect, the invention provides a method of obtaining β-phellandrene hydrocarbons in cyanobacteria as described herein that express a heterologous β-phellandrene synthase gene, where the method comprises mass-culturing cyanobacteria as described herein under conditions in which the β-phellandrene synthase gene is expressed.

In another aspect, the invention provides a method of obtaining β-phellandrene in cell culture comprising genetically modified cyanobacteria, wherein the photosynthetically generated β-phellandrene accumulates as a non-miscible product floating on the top of the liquid culture.

BRIEF DESCRIPTION OF THE DRAWINGS

FIG. 2. Amino acid sequence alignment of β-phellandrene synthase protein from lavender (*Lavandula angustifolia*), SEQ ID NO:4; tomato (*Solanum lycopersicum*), SEQ ID NO:5; grand fir (*Abies grandis*), SEQ ID NO:6, and spruce (*Picea sitchensis* 2, 3, 1, and 4), SEQ ID NOS:7, 8, 9, and 10, respectively. The Clustal 2.1 software application (University College, Dublin, Ireland) was used to perform the multiple sequence alignment analysis.

FIG. 3. The β-phellandrene synthase nucleotide and protein sequences employed in the present invention. (Part A) Amino acid sequence of S-β-PHLS protein (SEQ ID NO:1) catalyzing the conversion of GPP to 13-PHL. (Part B) The *L. angustifolia* β-PHLS (La-β-PHLS) cDNA nucleotide sequence (SEQ ID NO:2; GenBank Accession No. HQ404305). The chloroplast transit peptide is indicated in bold, and start and stop codons are underlined. (Part C) Codon-optimized version of *Lavandula angustifolia* β-PHLS cDNA nucleotide sequence minus the chloroplast transit peptide (SEQ ID NO:3) for expression in microorganisms, e.g. *Synechocystis* sp. PCC 6803 and *E. coli*. This codon-optimized sequence was termed S-β-PHLS. Start and stop codons are indicated. Restriction sites incorporated into the synthesized sequence for cloning purposes are underlined; PacI and NdeI sites at the start of the sequence, and BglII and NotI sites after the stop codon.

DETAILED DESCRIPTION OF THE INVENTION

Definitions

Figure 1:
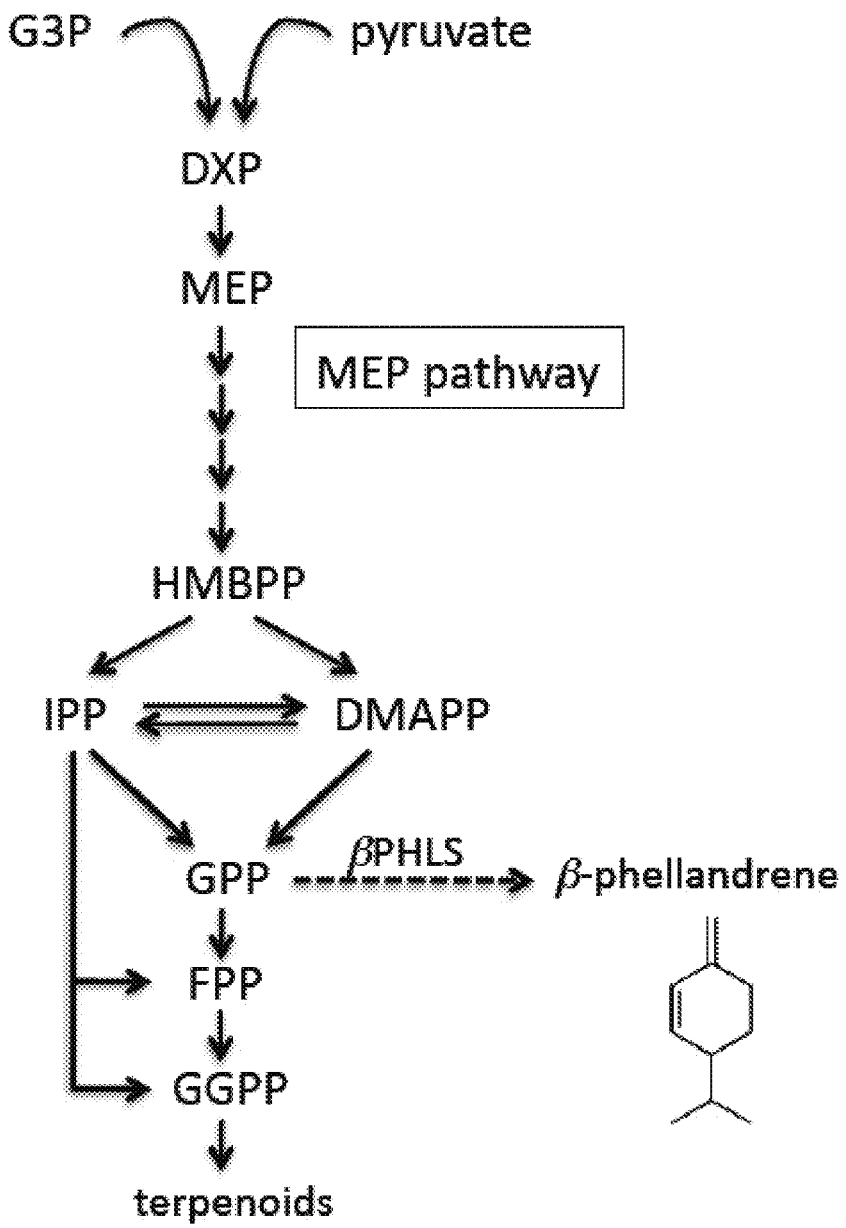
FIG. 1. Terpenoid biosynthesis via the MEP (methylerythritol-4-phosphate) pathway in photosynthetic microorganisms, e.g. *Synechocystis* sp. Abbreviations used: G3P=glyceraldehyde 3-phosphate; DXP=deoxyxylulose 5-phosphate; HMBPP=hydroxymethylbutenyl diphosphate; IPP=isopentenyl diphosphate; DMAPP=dimethylallyl diphosphate; GPP=geranyl diphosphate; FPP=farnesyl diphosphate; GGPP=geranylgeranyl diphosphate; β-PHLS=β-phellandrene synthase. Solid lines represent reactions catalyzed by endogenous *Synechocystis* enzymes, whereas the dashed line show the reaction catalyzed by the heterologously expressed S-β-PHLS construct.
Figure 4:
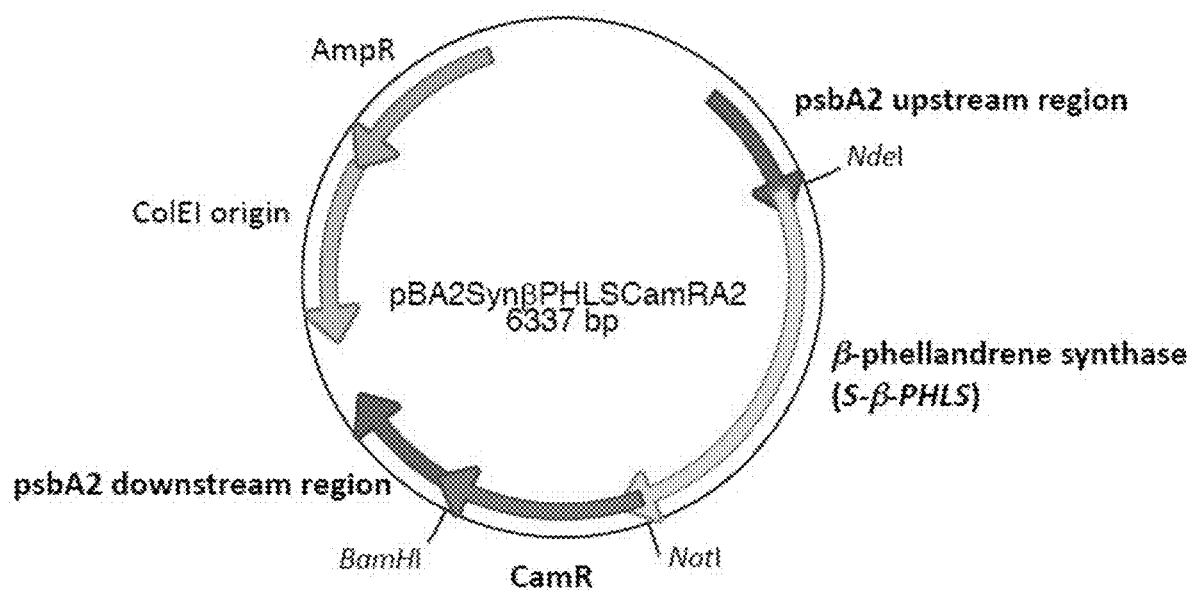
FIG. 4. Plasmid construct for expression of S-β-PHLS in cyanobacteria, e.g. *Synechocystis*. The *Synechcystis* codon-optimized β-phellandrene synthase gene (S-β-PHLS) and a chloramphenicol resistance cassette (CamR), were cloned into a vector containing upstream and downstream regions of the *Synechocystis* PsbA2 gene. Restriction sites used for cloning purposes are indicated. This plasmid was used for the transformation of wild-type *Synechocystis* cells, and facilitated the integration of the S-β-PHLS-CamR cassette within the *Synechocystis* genome at the PsbA2 locus via double homologous recombination.
Figure 5:
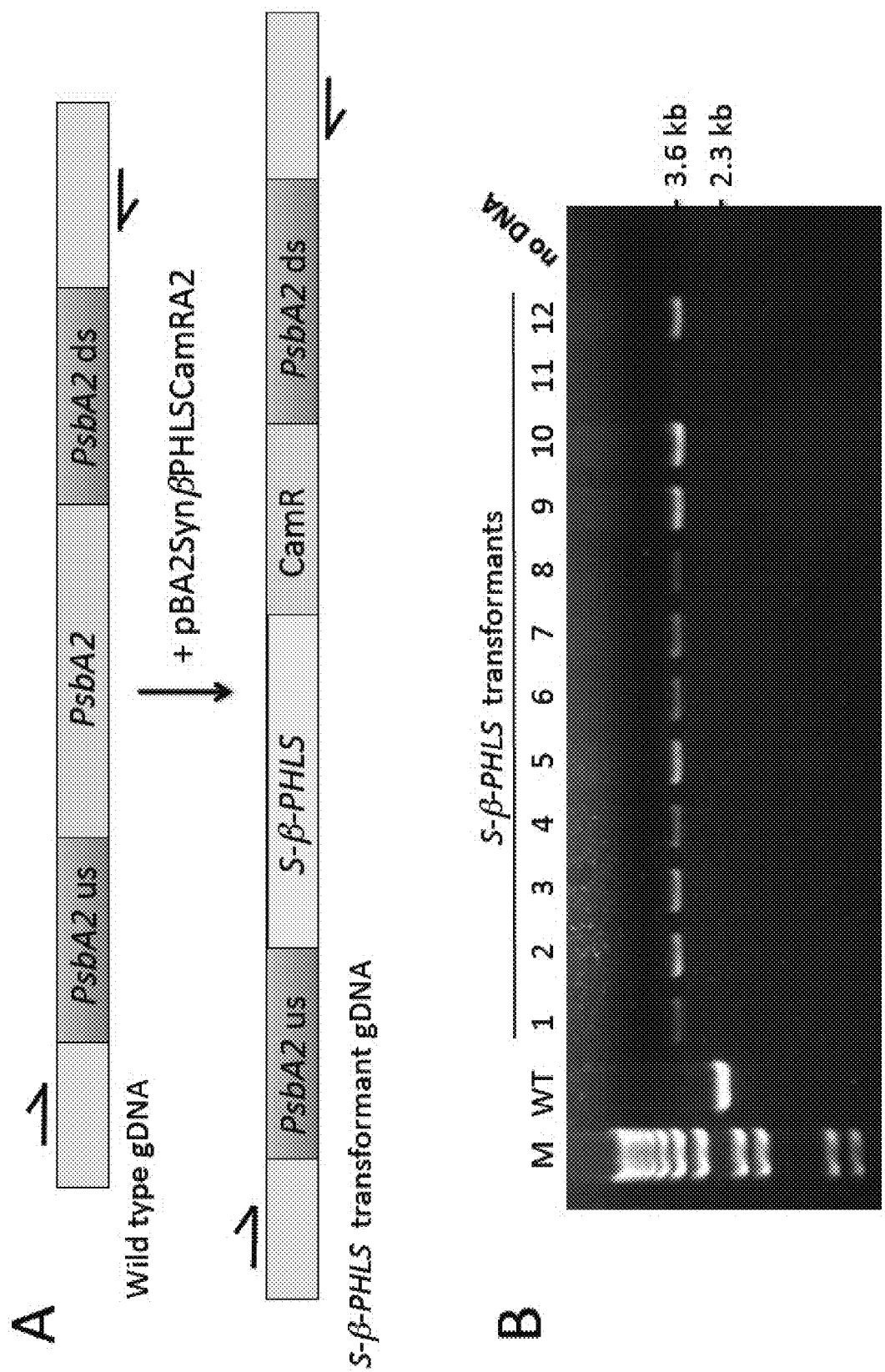
FIG. 5. Double homologous recombination and *Synechocystis* DNA copy segregation. Panel A shows maps of the PsbA2 gene locus in wild-type *Synechocystis* and in the S-β-PHLS transformants upon integration of the S-β-PHLS-CamR gene construct into the *Synechocystis* genome via double homologous recombination upon transformation with plasmid pBA2SynβPHLSCamRA2. Genomic PCR primers (arrows) were designed to flanking regions of the upstream and downstream regions of the PsbA2 gene (PsbA2 us, PsbA2 ds) that were used for homologous recombination. These amplify a 3.6 kb product in the S-β-PHLS transformant compared to a 2.3 kb product in the wild type. Panel B shows complete DNA copy segregation in 12 transformant lines following the replacement of PsbA2 with the heterologous S-β-PHLS transgene construct using the above-mentioned primers. A PCR product of ~2.3 kb was amplified in the wild type (WT) containing the endogenous PsbA2, whereas larger products of ~3.6 kb were amplified in twelve different S-β-PHLS transformant lines (1-12). Absence of the 2.3 kb product from the latter indicates homoplasmy for the introduced transgene. M, 1 kb plus marker.

A "β-phellandrene hydrocarbon", "β-phellandrene" or "β-PHL" in the context of this invention refers to a monoterpene with a chemical formula $C_{10}H_{16}$. The IUPAC name is 3-Methylene-6-(1-methylethyl)cyclohexene or 3-methylidene-6-propan-2-ylcyclohexene. β-phellandrene is also referred to as 3-isopropyl-6-methylene-1-cyclohexene or p-mentha-1(7),2-diene. The CAS number is 555-10-2 and Pubchem CID number is 11142. β-Phellandrene is a water-insoluble cyclic monoterpene with an endocyclic and an exocyclic double bond.

A "β-PHLS gene" or "β-PHLS polynucleotide" in the context of this invention refers to a nucleic acid that encodes a β-PHLS protein, or fragment thereof. In some embodiments, the gene is a cDNA sequence that encodes β-PHLS. In other embodiments, a β-PHLS gene may include sequences, such as introns, that are not present in a cDNA. In some embodiments, a "β-PHLS gene" refers to a nucleic acid sequence that encodes a β-PHLS polypeptide, e.g., a β-PHLS polypeptide shown in FIG. 2, or a homolog, fragment, or variant of a β-PHLS polypeptide shown in FIG. 2. In some embodiments, a "β-PHLS gene" encodes a β-PHLS polypeptide having a sequence set forth in SEQ ID NO:1 or encodes a homolog, fragment, or variant of the polypeptide of SEQ ID NO:1. In some embodiments, a "β-PHLS gene" comprises the coding region of SEQ ID NO:2 or SEQ ID NO:3; or comprises a nucleic acid sequence that is substantially similar to the β-PHLS protein coding region of SEQ ID NO:2 or SEQ ID NO:3. Thus, in some embodiments, a β-PHLS polynucleotide: 1) comprises a region of about 15 to about 50, 100, 150, 200, 300, 500, 1,000, 1500, or 1700 or more nucleotides, sometimes from about 20, or about 50, to about 1800 nucleotides and sometimes from about 200 to about 600 or about 1700 nucleotides of SEQ ID NO:2 or SEQ ID NO:3; or 2) hybridizes to SEQ ID NO:2 or SEQ ID NO:3, or the complements thereof, under stringent conditions, or 3) encodes a β-PHLS polypeptide or fragment of at least 50 contiguous amino acids, typically of at least 100, 150, 200, 250, 300, 350, 400, 450, 500, or 550, or more contiguous residues of a β-PHLS polypeptide shown in FIG. 2, such as the lavender β-PHLS sequence SEQ ID NO:1; or 4) encodes a β-PHLS polypeptide or fragment that has at least 25%, 30%, 35%, 40%, 45%, 45%, 50%, or 55%, and often at least 60%, 65%, 70%, 75%, 80%, 85%, 90%, 95%, or greater, identity to SEQ ID NO:1, or over a comparison window of at least 100, 200, 300, 400, 500, or 550 amino acid residues of SEQ ID NO:1; or 5) has a nucleic acid sequence that has greater than about 60%, 65%, 70%, 75%, 80%, 85%, 90%, 95%, 96%, 97%, 98%, 99%, or higher nucleotide sequence identity to SEQ ID NO:2 or SEQ ID NO:3, at least 80%, 85%, 90%, or at least 95%, 96%, 97%, 98%, 99% or greater identity over a comparison window of at least about 50, 100, 200, 500, 1000, 1500, 2000, or more nucleotides of SEQ ID NO:2 or SEQ ID NO:3; or 6) is amplified by primers to SEQ ID NO:2 or SEQ ID NO:3. The term "β-PHLS polynucleotide" refers to double stranded or singled stranded nucleic acids. The β-PHLS nucleic acids for use in the invention encode an active β-PHLS that catalyzes the conversion of geranyl diphosphate (GPP) or neryl-diphosphate (NPP), which is the cis isomer of GPP, to 0-phellandrene.

A "codon-optimized variant of a β-PHLS nucleic acid", e.g., a codon-optimized variant of SEQ ID NO:2 in the context of this invention, refers to a variant that encodes the same protein, e.g., SEQ ID NO:1, but contains nucleotide substitutions based on frequency of codon occurrence in cyanobacteria. For instance, SEQ ID NO:3 represents a codon-optimized variant of SEQ ID NO:2 for expression in the glucose-tolerant cyanobacterial strain *Synechocystis* sp. PCC 6803. The method of generating a codon-optimized variant includes modifying one or more codons of a gene to eliminate codons that are rarely used in the host cell, and adjusting the AT/GC ratio to that of the host cell. Rare codons can be defined, e.g., by using a codon usage table derived from the sequenced genome of the host cell.

A "β-PHLS polypeptide" as herein refers to a β-PHLS polypeptide a protein that catalyzes the conversion of geranyl diphosphate (GPP) or neryl-diphosphate (NPP) to β-phellandrene. A "β-PHLS polypeptide" thus refers to a polypeptide having the amino acid sequence of a β-PHLS shown in FIG. 2, or a fragment or variant thereof. In some embodiments, a β-PHLS polypeptide has the amino acid sequence of SEQ ID NO:1, or a fragment or variant thereof. Thus, a β-PHLS polypeptide can: 1) have at least 25%, 30%, 35%, 40%, 45%, 45%, 50%, or 55%, and typically at least 60%, 65%, 70%, 75%, 80%, 85%, 90%, 95% or greater identity to SEQ ID NO:1, or over a comparison window of at least 100, 200, 250, 300, 250, 400, 450, 500, or 550 amino acids of SEQ ID NO:1, or has at least 70%, 75%, 80%, 85%, 90%, 95% or greater identity to a β-PHLS polypeptide of FIG. 2; or a subfragment comprising at least 100, 200, 250, 300, 250, 400, 450, 500, or 550 amino acids of a β-PHLS polypeptide of FIG. 2; or 2) comprise at least 100, typically at least 200, 250, 300, 350, 400, 450, 500, 550, or more contiguous amino acids of a β-PHLS shown in FIG. 2, or comprise at least 100, typically at least 200, 250, 300, 350, 400, 450, 500, 550, or more contiguous amino acids of SEQ ID NO:1; or 3) specifically binds to antibodies raised against an immunogen comprising an amino acid sequence of a β-PHLS of FIG. 2, e.g., SEQ ID NO:1.

As used herein, a homolog or ortholog of a particular β-PHLS gene (e.g., SEQ ID NO:2) is a second gene in the same plant type or in a different plant type that is substantially identical (determined as described below) to a sequence in the first gene.

In the case of expression of transgenes one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "β-PHLS polynucleotide sequence" or "β-PHLS gene".

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. *APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (CLUSTAL, GAP, BESTFIT, BLAST, FASTA, and TFASTA), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. A "comparison window", as used herein, includes reference to a segment of any one of the number of contiguous positions, e.g., 20 to 600, usually about 50 to about 200, more usually about 100 to about 150 in which a sequence may be compared to a reference sequence of the same number of contiguous positions after the two sequences are optimally aligned.

The term "substantial identity" in the context of polynucleotide or amino acid sequences means that a polynucleotide or polypeptide comprises a sequence that has at least 50% sequence identity to a reference sequence. Alternatively, percent identity can be any integer from 50% to 100%. Exemplary embodiments include at least: at least 25%, 30%, 35%, 40%, 45%, 50%, 55%, 60%, 65%, 70%, 75%, 80%, 85%, 90%, 95%, 99% or 100% identity compared to a reference sequence using the programs described herein; preferably BLAST using standard default parameters, as described below. Accordingly, β-PHLS sequences of the invention include nucleic acid sequences that have substantial identity to the codon-optimized version of the *L. angustifolia* β-PHLS coding region (SEQ ID NO:3) or to the *L. angustifolia* β-PHLS coding region (SEQ ID NO:2). As noted above, β-PHLS polypeptide sequences of the invention include polypeptide sequences having substantial identify to SEQ ID NO:1.

The terms "nucleic acid" and "polynucleotide" are used synonymously and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see, e.g., Eckstein, F., Oligonucleotides and Analogues: A Practical Approach, Oxford University Press, 1991); and peptide nucleic acid backbones and linkages. Other analog nucleic acids include those with positive backbones; non-ionic backbones, and non-ribose backbones. Thus, nucleic acids or polynucleotides may also include modified nucleotides, that permit correct read through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc The phrase "a nucleic acid sequence encoding" refers to a nucleic acid which contains sequence information for a structural RNA, or the primary amino acid sequence of a specific protein or peptide, or a binding site for a trans-acting regulatory agent. This phrase specifically encompasses degenerate codons (i.e., different codons which encode a single amino acid) of the native sequence or sequences that may be introduced to conform with codon preference in a specific host cell. In the context of this invention, the term "β-PHLS coding region" when used with reference to a nucleic acid reference sequence such as SEQ ID NO:2 or 3 refers to the region of the nucleic acid that encodes β-PHLS protein.

The term "promoter" or "regulatory element" refers to a region or sequence determinants located upstream or downstream from the start of transcription that direct transcription. As used herein, a promoter includes necessary nucleic acid sequences near the start site of transcription, such as, in the case of a polymerase II type promoter, a TATA element. A promoter also optionally includes distal elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter) and a second nucleic acid sequence, such as a β-PHLS gene, wherein the expression control sequence directs transcription of the nucleic acid corresponding to the second sequence. A "cyanobacteria promoter" is a promoter capable of initiating transcription in cyanobacterial cells, respectively. Such a promoter is therefore active in a cyanobacteria cell, but need not originate from that organism. It is understood that limited modifications can be made without destroying the biological function of a regulatory element and that such limited modifications can result in cyanobacteria regulatory elements that have substantially equivalent or enhanced function as compared to a wild type cyanobacteria regulatory element. These modifications can be deliberate, as through site-directed mutagenesis, or can be accidental such as through mutation in hosts harboring the cyanobacteria regulatory element as long as the ability to confer expression in unicellular and multicellular cyanobacteria is substantially retained.

An "expression construct" in the context of this invention refers to a nucleic acid encoding a β-PHLS protein operably linked to a promoter. The nucleic acid encoding the β-PHLS protein is considered to be heterologous to a cyanobacterial host cell, as cyanobacteria do not have a β-PHLS. An expression construct includes embodiments in which the β-PHLS nucleic acid is linked to an endogenous promoter, e.g., the β-PHLS nucleic acid may be integrated into cyanobacterial DNA such that expression is controlled by the native promoter. In further embodiments, the β-PHLS nucleic acid is operably linked to a promoter that is introduced into the cyanbacterial host cell with the β-PHLS.

A "PsbA2 promoter" refers to a promoter region that regulates expression of psbA2. The promoter region the psbA2 gene has been well characterized (Eriksson et al., *Mol Cell Biol Res Commun* 3: 292-298 (2000); Mohamed et al., *Mol Gen Genet* 238: 161-168 1 (993); Mohamed and Jansson, *Plant Mol Biol* 13: 693-700 (1989)). Often, the PsbA2 promoter that is operably linked to the β-PHLS gene of this invention is the endogenous cyanobacteria promoter, but a heterologous PsbA2 promoter may also be employed. Such promoter sequences typically include High Light Regulatory 1 (HLR1) sequences that are involved in photoregulation as well as minimal promoter sequences (see, e.g., Eriksson et al., *Mol. Cell Biol Res. Commun.* 3: 292-298 (2000)).

"Expression" of a β-PHLS gene in the context of this invention typically refers introducing a β-PHLS gene into cyanobacteria cells, in which it is not normally expressed. Accordingly, an "increase" in β-PHLS activity or expression is generally determined relative to wild-type cyanobacteria that have no β-PHLS activity.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants. A "heterologous" promoter is a promoter that is not native to the host cell or that has been modified by human action.

Polypeptides that are "substantially similar" share sequences as noted above except that residue positions that are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Techniques in Biochemistry and Molecular Biology—Hybridization with Nucleic Probes. (Tijssen, P., ed.), Elsevier, New York (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 55° C., 60° C., or 65° C. Such washes can be performed for 5, 15, 30, 60, 120, or more minutes.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. For example, β-phellandrene synthase polynucleotides, can also be identified by their ability to hybridize under stringent conditions (e.g., Tm~40° C.) to nucleic acid probes having the sequence of SEQ ID NO:2 or by their ability to hybridize under stringent conditions (e.g., Tm~40° C.) to nucleic acid probes having the sequence of SEQ ID NO:3. Such a β-phellandrene synthase nucleic acid sequence can have, e.g., about 25-30% base pair mismatches or less relative to the selected nucleic acid probe. SEQ ID NOS:2 and 3 are examples of nucleic acids that encode a *L. angustifolia* β-phellandrene synthase polypeptide. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

The term "isolated", when applied to a nucleic acid or protein, denotes that the nucleic acid or protein is essentially free of other cellular components with which it is associated in the natural state. It is preferably in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest.

As used herein, "mass-culturing" refers to growing large quantities of cyanobacteria, that have been modified to express a β-phellandrene synthase gene. A "large quantity" is generally in the range of about 100 liters to about 1,500,000 liters, or more. In some embodiments, the organisms are cultured in large quantities in modular bioreactors, each having a capacity of about 1,000 to about 1,000,000 liters.

A "bioreactor" in the context of this invention is any enclosed large-capacity vessel in which cyanobacteria are grown. A "large-capacity vessel" in the context of this invention can hold about 100 liters, often about 500 liters, or about 1,000 liters to about 1,000,000 liters, or more.

As used herein, "harvesting" or "isolating" β-phellandrene hydrocarbons refers to collecting the β-phellandrene that has diffused into culture medium from the culture medium.

INTRODUCTION

The invention employs various routine recombinant nucleic acid techniques. Generally, the nomenclature and the laboratory procedures in recombinant DNA technology described below are those well-known and commonly employed in the art. Many manuals that provide direction for performing recombinant DNA manipulations are available, e.g., Molecular Cloning, A Laboratory Manual. (Sambrook, J. and Russell, D., eds.), CSHL Press, New York (3rd Ed, 2001); and Current Protocols in Molecular Biology. (Ausubel et al., eds.), New Jersey (1994-1999).

In one aspect, the invention is based, in part, on the discovery that in cyanobacteria, β-phellandrene diffuses into the culture media, unlike other long-chain hydrocarbons of the terpenoid and fatty acid biosynthetic pathways. Accordingly, the invention provides methods and compositions for producing β-phellandrene by expressing β-phellandrene synthase in cyanobacteria.

β-Phellandrene Synthase Nucleic Acids

β-phellandrene synthase nucleic acid and polypeptide sequences are known in the art. β-phellandrene synthase genes have been isolated, sequenced and characterized from lavender (*Lavandular angustifolia*), grand fir (*Abies grandis*), tomato (*Solanum lycopersicum*) and spruce (*Picea abies, Picea sitchensis*). See, e.g., Demissie et al., *Planta*, 233:685-696 (2011); Bohlmann et al., *Arch. Biochem. Biophys.*, 368:232-243 (1994); Schilmiller et al., *Proc. Nat. Acad. Sci. U.S.A.*, 106:10865-10870 (2009); and Keeling et al., *BMC Plant Biol.* 11:43-57 (2011). Illustrative accession numbers are: lavender (*Lavandula angustifolia* cultivar Lady), Accession: HQ404305; tomato (*Solanum lycopersicum*), Accession: FJ797957; grand fir (*Abies grandis*), Accession: AF139205; spruce (*Picea sitchensis*) (4 genes identified, Accession Nos: Q426162 (PsTPS-Phel-1), HQ426169 (PsTPS-Phel-2), HQ426163 (PsTPS-Phel-3), HQ426159 (PsTPS-Phel-4). FIG. 2 illustrates an amino acid alignment of β-phellandrene synthases from lavender, grand fir, tomato and spruce. The conserved motifs are underlined.

Amino acid sequence comparison of lavender (*Lavandular angustifolia*) β-phellandrene synthase with those of grand fir (*Abies grandis*) and tomato (*Solanum lycopersicum*) showed 29% and 15% identity, respectively. There is a 26% amino acid sequence identity between *Lavandular angustifolia* (lavender) and *Picea sitchensis* (spruce) β-phellandrene synthases. In terms of similarity, amino acid sequence comparison of lavender (*Lavandular angustifolia*) β-phellandrene synthase with those of grand fir (*Abies grandis*) and tomato (*Solanum lycopersicum*) showed 75% and 61% similarity, respectively. There is 73% amino acid sequence similarity between *Lavandular angustifolia* (lavender) and *Picea sitchensis* (spruce) β-phellandrene synthases. Although amino acid sequence comparison of all known β-phellandrene synthases, shown in FIG. 2, revealed a low amino acid identity over the length of all the sequences, there are regions that are conserved.

β-Phellandrene synthases (and other monoterpene synthases such as linalool synthase) share several conserved motifs (see, e.g., Demissie et al., *Planta* 233:685-696, (2011)). FIG. 2 illustrates an amino acid alignment of β-phellandrene synthase proteins from *Lavandular angustifolia, Abies grandis, Solanum lycopersicum* and *Picea sitchensis*. The monoterpene synthase signature arginine-rich N-terminal RR(x8)W motif (underlined in FIG. 2) is required for cyclization of geranyl-diphosphate (see, e.g., Williams J G K. *Methods Enzymol.*, 167:766-778 (1988)). The arginine rich motif is located near the N-terminus of the mature protein (Demissie et al., *Planta* 233:685-696, (2011)). The highly conserved aspartate-rich DDxxD motif (underlined in FIG. 2) is required for substrate binding, a process usually assisted by divalent cations, e.g. $Mg^{2+}$ (see, e.g., Nieuwenhuizen et al., *J. Exp. Bot.* 60(11):3203-3219 (2009)). The partially conserved amino acid sequences, LQLYEASFLL (SEQ ID NO:11) (underlined in FIG. 2) and (N,D)D(L,I,V)x(S,T)xxxE (underlined in FIG. 2) play roles in catalysis and second metal ion binding, respectively (see, e.g., Wise et al., *J. Biol. Chem.*, 273:14891-14899 (1998); Degenhardt et al, *Phytochemistry*, 70 (15-16):1621-1637 (2009).; Roeder et al., *Plant Mol Biol* 65(1):107-124 (2007)). A β-phellandrene synthase gene for use in the invention encodes a protein retaining the motifs. Further, one of skill can employ an alignment of the protein sequences to select residues that may be varied, e.g., by conservative substitution, that retain function.

Differences between monoterpene synthases have been identified in several plant organisms. For instance, monoterpene synthases (e.g., β-phellandrene synthase and linalool synthase) from a given organism have greater homology to each other, compared to monoterpene synthase orthologs from different species. Substrates of monoterpene synthases can also vary between plant species. For example, tomato β-phellandrene synthase uses neryl diphosphate (NPP), which is the cis-isomer of GPP, as a substrate, rather than geranyl-diphosphate, a common substrate for other known monoterpene synthases (Schilmiller et al., *Proc. Natl. Acad. Sci. USA* 106:10865-10870, 2009).

The methods of the invention comprise expressing a nucleic acid sequence that encodes a β-phellandrene synthase polypeptide, e.g., a polypeptide having a sequence at least 70%, at least 75%, at least 80%, at least 85%, at least 90%, or at least 95%, or greater, identity to a β-PHLS polypeptide set forth in FIG. 2, e.g., a SEQ ID NO:1, in cyanobacteria. A β-PHLS polypeptide encoded by a nucleic acid employed in the methods of the invention have the catalytic activity of converting GPP or its cis-isomer to β-phellandrene. In some embodiments, the invention provides a β-PHLS gene that encodes a modified version of a β-PHLS polypeptide from a plant, such as lavender, grand fir, tomato, or spruce. A β-PHLS polypeptide variant suitable for use in the present invention possesses the ability to convert GPP or NPP to β-phellandrene when heterologously expressed in cyanobacteria. In some embodiments, the β-PHLS polypeptide variant employs GPP. In some embodiments, a β-PHLS for use in the invention has at least 70%, typically at least 75%, at least 80%, at least 85%, at least 90%, at least 95%, or greater, identity to a β-PHLS polypeptide from lavender, grand fir or spruce set forth in FIG. 2. Typically, the level of activity is equivalent to the activity exhibited by a natural β-phellandrene synthase polypeptide (e.g., SEQ ID NO:1) to produce β-phellandrene. A β-phellandrene synthase polypeptide suitable for producing β-phellandrene has at least 20%, at least 30%, at least 40%, at least 50%, at least 60%, at least 70%, at least 80%, at least 90% or at least 95%, or greater, of the activity of an endogenous β-PHLS polypeptide from a plant, such as lavender, grand fir, tomato, and spruce, e.g., a β-PHLS having a sequence set forth in SEQ ID NO:2.

Activity of a heterologous β-phellandrene synthase of the present invention can be assayed by methods known to those skilled in the art. Non-limiting examples of assays that measure the function of β-phellandrene synthase to produce β-phellandrene from the substrate GPP or NPP include in vitro enzymatic assays using purified recombinant β-phellandrene synthase protein, assays that determine the enzyme saturation kinetics, GC and GC-MS analysis to measure β-phellandrene production (detailed description in Example), spectrophotometric analysis for β-phellandrene quantification (detailed description in Example).

β-Phellandrene Synthase Expression Constructs

β-PHLS nucleic acid sequences of the invention are expressed recombinantly in cyanobacteria. Expression constructs can be designed taking into account such properties as codon usage frequencies of the organism in which the β-PHLS nucleic acid is to be expressed. Codon usage frequencies can be tabulated using known methods (see, e.g., Nakamura et al. *Nucl. Acids Res.* 28:292 (2000)). Codon usage frequency tables, including those for cyanobacteria, are also available in the art (e.g., in codon usage databases of the Department of Plant Genome Research, Kazusa DNA Research Institute, Japan).

In certain embodiments, the invention provides a β-PHLS gene that encodes a *L. angustifolia* β-PHLS protein, where the gene is a codon-optimized variant of a lavender β-PHLS gene, e.g., a codon-modified variant of SEQ ID NO:2.

Isolation or generation of β-PHLS polynucleotide sequences can be accomplished by well-known techniques, including amplification techniques and/or library screening.

Appropriate primers and probes for generating a β-PHLS gene can be designed based on known principles using, e.g., the β-PHLS sequences provided herein. For a general overview of PCR see PCR Protocols: A Guide to Methods and Applications. (Innis, M, Gelfand, D., Sninsky, J. and White, T., eds.), Academic Press, San Diego (1990). An illustrative PCR for amplifying a β-PHLS nucleic acid sequence is provided in the examples.

β-PHLS nucleic acid sequences for use in the invention include genes and gene products identified and characterized by techniques such as hybridization and/or sequence analysis using an exemplary nucleic acid sequence, e.g., SEQ ID NO:3. In some embodiments, a β-PHLS nucleic acid sequence for use in the invention has at least 90%, at least 91%, at least 92%, at least 93%, at least 94%, at least 95%, at least 96%, at least 97%, at least 98%, at least 99% to SEQ ID NO:3. In some embodiments the β-PHLS nucleic acid sequence comprises SEQ ID NO:3.

To use isolated sequences in the above techniques, recombinant DNA vectors suitable for transformation of cyanobacteria are prepared. Techniques for transformation are well known and described in the technical and scientific literature. For example, a DNA sequence encoding a β-PHLS gene (described in further detail below), can be combined with transcriptional and other regulatory sequences which will direct the transcription of the sequence from the gene in the intended cells of the transformed cyanobacteria. In some embodiments, an expression vector that comprises an expression cassette that comprises the β-PHLS gene further comprises a promoter operably linked to the β-PHLS gene. In other embodiments, a promoter and/or other regulatory elements that direct transcription of the β-PHLS gene are endogenous to the cyanobacteria and the expression cassette comprising the β-PHLS gene is introduced, e.g., by homologous recombination, such that the heterologous β-PHLS gene is operably linked to an endogenous promoter and is expression driven by the endogenous promoter.

Regulatory sequences include promoters, which may be either constitutive or inducible. In some embodiments, a promoter can be used to direct expression of β-PHLS nucleic acids under the influence of changing environmental conditions. Examples of environmental conditions that may affect transcription by inducible promoters include anaerobic conditions, elevated temperature, or the presence of light. Promoters that are inducible upon exposure to chemicals reagents are also used to express β-PHLS nucleic acids. Other useful inducible regulatory elements include copper-inducible regulatory elements (Mett et al., *Proc. Natl. Acad. Sci. USA* 90:4567-4571 (1993); Furst et al., *Cell* 55:705-717 (1988)); tetracycline and chlor-tetracycline-inducible regulatory elements (Gatz et al., *Plant J.* 2:397-404 (1992); Röder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible promoters, such as those of the hsp70/dnaK genes (Takahashi et al., *Plant Physiol.* 99:383-390 (1992); Yabe et al., *Plant Cell Physiol.* 35:1207-1219 (1994); Ueda et al., *Mol. Gen. Genet.* 250:533-539 (1996)); and lac operon elements, which are used in combination with a constitutively expressed lac repressor to confer, for example, IPTG-inducible expression (Wilde et al., *EMBO J.* 11:1251-1259 (1992)). An inducible regulatory element also can be, for example, a nitrate-inducible promoter, e.g., derived from the spinach nitrite reductase gene (Back et al., *Plant Mol. Biol.* 17:9 (1991)), or a light-inducible promoter, such as that associated with the small subunit of RuBP carboxylase or the LHCP gene families (Feinbaum et al., *Mol. Gen. Genet.* 226:449 (1991); Lam and Chua, Science 248:471 (1990)), or a light.

In some embodiments, the promoter may be from a gene associated with photosynthesis in the species to be transformed or another species. For example such a promoter from one species may be used to direct expression of a protein in transformed cyanobacteria cells. Suitable promoters may be isolated from or synthesized based on known sequences from other photosynthetic organisms. Preferred promoters are those for genes from other photosynthetic species, or other photosynthetic organism where the promoter is active in cyanobacteria.

In some embodiments, a promoter used to drive expression of a heterologous β-PHLS gene is a constitutive promoter. Examples of constitutive strong promoters for use in cyanobacteria include, for example, the psbDI gene or the basal promoter of the psbDII gene. Various other promoters that are active in cyanobacteria are also known. These include the light inducible promoters of the psbA and psbA3 genes in cyanobacteria and promoters such as those set forth in U.S. Patent Application Publication No. 20020164706, which is incorporated by reference. Other promoters that are operative in plants, e.g., promoters derived from plant viruses, such as the CaMV35S promoters, can also be employed in cyanobacteria. For a description of strong and regulated promoters, e.g., active in the cyanobacterium *Anabaena* sp. strain PCC 7120, see e.g., Elhai, *FEMS Microbiol Lett* 114:179-184, (1993)). In other embodiments, other locus in the cyanobacterial chloroplast genome can be used to drive expression of the heterologous β-PHLS gene, provided that the locus permits relatively high expression levels of the heterologous gene. In particular embodiments, In some embodiments, promoters are identified by analyzing the 5' sequences of a genomic clone corresponding to a β-PHLS gene. Sequences characteristic of promoter sequences can be used to identify the promoter.

A promoter can be evaluated, e.g., by testing the ability of the promoter to drive expression in cyanobacteria in which it is desirable to introduce a β-PHLS expression construct.

A vector comprising β-PHLS nucleic acid sequences will typically comprise a marker gene that confers a selectable phenotype on cyanobacteria transformed with the vector. Such markers are known. For example, the marker may encode antibiotic resistance, such as resistance to chloramphenicol, kanamycin, G418, bleomycin, hygromycin, and the like.

Heterologous Expression of β-Phellandrene Synthase Gene in Cyanobacteria

Cell transformation methods and selectable markers for cyanobacteria are well known in the art (Wirth, *Mol. Gen. Genet.*, 216(1):175-7 (1989); Koksharova, *Appl. Microbiol. Biotechnol.*, 58(2): 123-37 (2002); Thelwell et al., *Proc. Natl. Acad. Sci. U.S.A.*, 95:10728-10733 (1998)). Transformation methods and selectable markers for are also well known (see, e.g., Sambrook et al., supra).

The codon-optimized β-phellandrene synthase gene of the present invention can be expressed in any number of cyanobacteria where it is desirable to produce β-phellandrene. Suitable unicellular cyanobacteria include *Synechocystis* sp., such as strain *Synechocystis* PCC 6803; and *Synechococcus* sp., e.g., the thermophilic *Synechococcus lividus*; the mesophilic *Synechococcus elongatus* or *Synechococcus* 6301. Multicellular, including filamentous cyanobacteria, may also be engineered to express β-PHLS in accordance with this invention. Multicellularr cyanobacteria that can be used include, e.g., *Gloeocapsa*, as well as filamentous cyanobacteria such as *Nostoc* sp., e.g., *Nostoc* sp. PCC 7120, *Nostoc sphaeroides*); *Anabaena* sp., e.g., *Anabaena variabilis*; and *Arthrospira* sp. ("*Spirulina*"), such as *Arthrospira platensis* and *Arthrospira maxima*. Cyanobacteria that are genetically modified in accordance with the invention to express a β-PHLS gene may also contain other genetic modifications, e.g., modifications to the terpenoid pathway, to enhance production of β-phellandrene.

In some embodiments, an expression construct is generated to allow the heterologous expression of the β-phellandrene synthase gene in *Synechocystis* through the replacement of the *Synechocystis* PsbA2 gene with the codon-optimized β-PHLS gene via double homologous recombination. In some embodiments, the expression construct comprises a codon-optimized β-phellandrene synthase gene operably linked to an endogenous cyanobacteria promoter. In some aspects, the promoter is the PsbA2 promoter.

In some embodiments, cyanobacteria are transformed with an expression vector comprising a β-PHLS gene and an antibiotic resistance gene. A detailed description is set forth in PCT Application No. PCT/US2007/71465, which is incorporated by reference. Transformants are cultured in selective media containing an antibiotic to which an untransformed host cell is sensitive. Cyanobacteria normally have up to 100 copies of identical circular DNA chromosomes in each cell. Successful transformation with an expression vector comprising a β-PHLS gene and an antibiotic resistance gene normally occurs in only one, or just a few, of the many cyanobacterial DNA copies. Hence, presence of the antibiotic is necessary to encourage expression of the transgenic copy(ies) of the DNA for β-phellandrene production. In the absence of the selectable marker (antibiotic), the transgenic copy(ies) of the DNA would be lost and replaced by wild-type copies of the DNA.

In some embodiments, cyanobacterial transformants are cultured under continuous selective pressure conditions (presence of antibiotic over many generations) to achieve DNA homoplasmy in the transformed host organism. One of skill in the art understands that the number of generations and length of time of culture varies depending on the particular culture conditions employed. Homoplasmy can be determined, e.g., by monitoring the DNA composition in the cells to determine the presence of wild-type copies of the cyanobacterial DNA.

"Achieving homoplasmy" refers to a quantitative replacement of most, e.g., 70% or greater, or typically all, wild-type copies of the cyanobacterial DNA in the cell with the transformant DNA copy that carries the β-PHLS transgene. This is normally attained over time, under the continuous selective pressure (antibiotic) conditions applied, and entails the gradual during growth replacement of the wild-type copies of the DNA with the transgenic copies, until no wild-type copy of the cyanobacterial DNA is left in any of the transformant cells. Achieving homoplasmy is typically verified by quantitative amplification methods such as genomic-DNA PCR using primers and/or probes specific for the wild-type copy of the cyanobacterial DNA. In some embodiments, the presence of wild-type cyanobacterial DNA can be detected by using primers specific for the wild-type cyanobacterial DNA and detecting the presence of the PsbA2 gene. Transgenic DNA is typically stable under homoplasmy conditions and present in all copies of the cyanobacterial DNA.

In some embodiments, cyanobacterial cultures can be cultured under conditions in which the light intensity is varied. Thus, for example, when a psbA2 promoter is used as a promoter to drive β-phellandrene synthase expression, transformed cyanobacterial cultures can be grown at low light intensity conditions (e.g., 10-50 μmol photons $m^{-2} s^{-1}$), then shifted to higher light intensity conditions (e.g., 500

μmol photons m$^{-2}$ s$^{-1}$). The psbA2 promoter responds to the shift in light intensity by up-regulating the expression of the β-PHLS gene in *Synechocystis*, typically at least about 10-fold. In other embodiments, cyanobacterial cultures can be exposed to increasing light intensity conditions (e.g., from 50 μmol photons m$^{-2}$ s$^{-1}$ to 2,500 μmol photons m$^{-2}$ s$^{-1}$) corresponding to a diurnal increase in light intensity up to full sunlight. The psbA2 promoter responds to the gradual increase in light intensity by up-regulating the expression of the β-PHLS gene in *Synechocystis* in parallel with the increase in light intensity.

Production of β-Phellandrene in Cyanobacteria

Transformed cyanobacteria (transformant cyanobacteria) are grown under conditions in which the heterologous β-PHLS gene is expressed. Methods of mass culturing cyanobacteria are known to one skilled in the art. For example, cyanobacteria can be grown to high cell density in photobioreactors (see, e.g., Lee et al., *Biotech. Bioengineering* 44:1161-1167, 1994; Chaumont, *J Appl. Phycology* 5:593-604, 1990). Examples of photobioreactors include cylindrical or tubular bioreactors, see, e.g., U.S. Pat. Nos. 5,958,761, 6,083,740, US Patent Application Publication No. 2007/0048859; WO 2007/011343, and WO2007/098150. High density photobioreactors are described in, for example, Lee, et al., Biotech. Bioengineering 44: 1 161-1 167, 1994. Other photobioreactors suitable for use in the invention are described, e.g., in WO/2011/034567 and references cited in the background section. Photobioreactor parameters that can be optimized, automated and regulated for production of photosynthetic organisms are further described in (Puiz (2001) Appl Microbiol Biotechnol 57:287-293). Such parameters include, but are not limited to, materials of construction, efficient light incidence into reactor lumen, light path, layer thickness, oxygen released, salinity and nutrients, pH, temperature, turbulence, optical density, and the like.

Transformed cyanobacteria that express a heterologous β-PHLS gene are grown under mass culture conditions for the production of β-phellandrene. In typical embodiments, the transformed organisms are growth in bioreactors or fermentors that provide an enclosed environment. For example, in some embodiments for mass culture, the cyanobacteria are grown in enclosed reactors in quantities of at least about 500 liters, often of at least about 1000 liters or greater, and in some embodiments in quantities of about 1,000,000 liters or more. One of skill understands that large-scale culture of transformed cyanobacteria that comprise a β-phellandrene synthase gene where expression is driven by a light sensitive promoter, such as a PsbA2 promoter, is typically carried out in conditions where the culture is exposed to natural light. Accordingly, in such embodiments appropriate enclosed reactors are used that allow light to reach the cyanobacteria culture.

Growth media for culturing cyanobacteria transformants are well known in the art. For example, cyanobacteria may be grown on solid media such as BG-11 media (see, e.g., Rippka et al., *J Gen Microbiol.* 111:1-61, 1979). Alternatively, they may be grown in liquid media (see, e.g., Bentley & Melis, *Biotechnol. Bioeng.* 109:100-109, 2012). In typical embodiments for production of β-phellandrene, liquid cultures are employed. For example, such a liquid culture may be maintained at about 25° C. under a slow stream of constant aeration and illumination, e.g., at 20 μmol photons m$^{-2}$ s$^{-1}$. In certain embodiments, an antibiotic, e.g., chloramphenical, is added to the liquid culture. For example, chloramphenicol may be used at a concentration of 15 μg/ml.

In some embodiments, cyanobacteria transformants are grown photoautotrophically in a gaseous/aqueous two-phase photobioreactor (see, e.g., Bentley & Melis, 2012, supra, and U.S. patent application No. 61/477,896). In certain embodiments, the methods of the present invention comprise obtaining β-phellandrene using a diffusion-based method for spontaneous gas exchange in a gaseous/aqueous two-phase photobioreactor. In particular aspects of the method, carbon dioxide is used as a feedstock for the photosynthetic generation of β-phellandrene in cell culture and the headspace of the bioreactor is filled with 100% $CO_2$ and sealed. This allows diffusion-based $CO_2$ uptake and assimilation by the cells via photosynthesis, and concomitant replacement of the $CO_2$ in the headspace with β-phellandrene vapour and $O_2$. Typically, the photosynthetically generated β-phellandrene accumulates as a non-miscible product floating on the top of the liquid culture.

In particular embodiments, a gaseous/aqueous two-phase photo-bioreactor is seeded with a culture of cyanobacterial cells and grown under continuous illumination, e.g., at 75 μmol photons m$^{-2}$ s$^{-1}$, and continuous bubbling with air. Inorganic carbon is delivered to the culture in the form of aliquots of 100% $CO_2$ gas, which is slowly bubbled through the bottom of the liquid culture to fill the bioreactor headspace. Once atmospheric gases is replaced with 100% $CO_2$, the headspace of the reactor is sealed and the culture is incubated, e.g., at about 25° C. to 37° C. under continuous illumination, e.g., of 150 μmol photons m$^{-2}$ s$^{-1}$. Slow continuous mechanical mixing is also employed to keep cells in suspension and to promote balanced cell illumination and nutrient mixing into the liquid culture in support of photosynthesis and biomass accumulation. Uptake and assimilation of headspace $CO_2$ by cells is concomitantly exchanged for $O_2$ during photoautotrophic growth. The sealed bioreactor headspace allows for the trapping, accumulation and concentration of photosynthetically produced β-phellandrene.

In some embodiments, the photoautotrophic cell growth kinetics of the cyanobacteria transformants are similar to those of wild type cyanobacteria cells. In some embodiments, the rates of oxygen consumption during dark respiration are about the same in wild type cyanobacteria cells. In other embodiments, the rates of oxygen evolution and the initial slopes of photosynthesis as a function of light intensity re comparable in wild-type *Synechocystis* cells and *Synechocystis* transformants, when both are at sub-saturating light intensities between 0 and 250 μmol photons m$^{-2}$ s$^{-1}$.

Conditions for growing β-PHLS-expressing cyanobacteria for the purposes illustrated above are known in the art (see, e.g., the illustrative references cited herein). β-phellandrene hydrocarbons produced by the modified cyanobacteria can be harvested using known techniques. β-phellandrene hydrocarbons are not miscible in water and they rise to and float at the surface of the microorganism growth medium. In typical embodiments, they are siphoned off from the surface and sequestered in suitable containers. In addition, and depending on the prevailing temperature during the mass cultivation of the cyanobacteria, β-phellandrene can exist in vapor form above the water medium in the bioreactor container (monoterpene hydrocarbons have a relatively high boiling temperature T=170-175° C.). In some embodiments, β-phellandrene vapor is piped off the bioreactor container and condensed into liquid 1 form upon cooling or low-level compression.

In typical embodiments, the photosynthetically produced β-phellandrene is in liquid form and floating on the aqueous phase of the liquid culture. In some embodiments, extraction of the β-phellandrene produced in accordance with the invention is performed by skimming the floating β-phellandrene from the surface of the liquid phase of the culture that is producing the β-phellandrene and isolating β-phellandrene in pure form. In certain embodiments, photosynthetically produced non-miscible β-phellandrene in liquid form is extracted from the liquid phase by a method comprising overlaying a solvent such as heptane, decane, or dodecane, on top of the liquid culture in the bioreactor, incubating for at room temperature, e.g. 30 minutes or longer; and removing the solvent, e.g., heptane, layer containing β-phellandrene. In some embodiments, photosynthetically produced β-phellandrene is a volatile product accumulating in the headspace of the bioreactor used for β-phellandrene production.

EXAMPLES

The examples described herein are provided by way of illustration only and not by way of limitation. Those of skill in the art will readily recognize a variety of non-critical parameters that could be changed or modified to yield essentially similar results.

Example 1. β-phellandrene Production Using Genetically Engineered Cyanobacteria

The invention provides method and compositions for the genetic modification of cyanobacteria to confer upon these microorganisms the ability to produce β-phellandrene ($C_{10}H_{16}$) upon heterologous expression of a β-phellandrene synthase gene, e.g., a β-phellnadrene synthase gene from lavender (Lavandular angustifolia), grand fir (Abies grandis), tomato (Solanum lycopersicum) or spruce (Picea abies, Picea sitchensis), or a variant thereof. In some embodiments, the invention provides for production of β-phellandrene hydrocarbons in gaseous-aqueous two-phase photo-bioreactors and results in the renewable generation of a hydrocarbon bio-product, which can be used, e.g., for generating fuel, chemical synthesis, or pharmaceutical and cosmetics applications. This example illustrates expression of a β-phellandrene synthase gene from lavender in cyanobacteria to produce β-phellandrene.

This example further illustrates that β-phellandrene can be continuously-generated in cyanobacteria transformants that express a β-phellandrene synthase gene. Further, this example demonstrates that β-phellandrene can spontaneously diffuse out of cyanobacteria transformants and into the extracellular water phase, and be collected from the surface of the liquid culture as a water-floating product. This example also demonstrates that this strategy for production of β-phellandrene alleviates product feedback inhibition, product toxicity to the cell, and the need for labor-intensive extraction protocols.

In the present example, photosynthetic microorganisms, with the cyanobacterium Synechocystis sp. PCC6803 as the model organism, were genetically engineered to express a β-phellandrene synthase gene from lavender (Lavandular angustifolia), thereby endowing upon them with the property of photosynthetic β-phellandrene production (FIG. 1). Genetically modified strains were used in an enclosed mass culture system to provide a renewable hydrocarbon in the form of β-phellandrene that is suitable as biofuel or feedstock in chemical synthesis. β-Phellandrene hydrocarbon products were spontaneously emitted by the cells into the extracellular space, followed by floating to the surface of the liquid phase, where they were easily be collected without imposing any disruption to the growth/productivity of the cells. The genetically modified cyanobacteria remained in a continuous growth phase, constitutively generating and emitting β-phellandrene. The example further provides an example of a codon-optimized β-phellandrene synthase gene for improved yield of β-phellandrene in photosynthetic cyanobacteria, e.g., Synechocystis.

Materials and Methods

Strains and Growth Conditions

The E. coli strain DH5a was used for routine subcloning and plasmid propagation, and grown in LB media with appropriate antibiotics as selectable markers at 37° C., according to standard protocols. The glucose-tolerant cyanobacterial strain Synechocystis sp. PCC 6803 (Williams, J G K. Methods Enzymol., 167:766-768 (1988)) was used as the recipient strain in this study, and is referred to as the wild type. Wild type and transformant strains were maintained on solid BG-11 media supplemented with 10 mM TES-NaOH (pH 8.2), 0.3% sodium thiosulfate, and 5 mM glucose. Where appropriate, chloramphenicol was used at a concentration of 15 μg/mL. Liquid cultures were grown in BG-11 containing 25 mM sodium phosphate buffer, pH 7.5. Liquid cultures for inoculum purposes and for photoautotrophic growth experiments and SDS-PAGE analyses were maintained at 25° C. under a slow stream of constant aeration and illumination at 20 μmol photons $m^{-2}$ $s^{-1}$. Growth conditions employed, when measuring the production of β-phellandrene from Synechocystis cultures, are described below in the β-phellandrene production assays section.

Codon-Use Optimization of the β-Phellandrene Synthase Gene for Expression in Synechocystis sp. PCC 6803 and Escherichia coli The nucleotide and translated protein sequences of the β-phellandrene synthase gene from Lavandula angustifolia cultivar Lady (GenBank Accession Number HQ404305) were obtained from the NCBI GenBank database (National Center for Biotechnology Information; see, e.g., http://www.ncbi.nlm.nih.gov/nuccore/HQ404305). The protein sequence of the β-phellandrene synthase gene was firstly analyzed by TargetP software (see, e.g., http://www.cbs.dtu.dk/services/TargetP/) for the prediction of the subcellular localization of the protein and for identification of the presence and length of any targeting/transit amino acid sequence. Based on this analysis, the β-phellandrene synthase from Lavandula angustifolia cultivar Lady was predicted to be a chloroplast localized protein with the first 42 amino acids of the protein serving as a chloroplast transit peptide. This analysis indicated that the first 42 amino acids are not part of the mature protein that functions in the catalysis of GPP conversion to β-phellandrene in the chloroplast. Based on this information, we designed a protein sequence from the original sequence of Lavandula phellandrene synthase (La-β-PHLS) gene by replacing the first 42 amino acids with a methionine. The codon-use of the resulting cDNA was then optimized for expression in Synechocystis sp. PCC 6803 and E. coli. The protein sequence of the β-phellandrene synthase that was employed in this work is composed of 540 amino acids of which the sequence is shown in FIG. 3A. To maximize the expression of β-phellandrene synthase in Synechocystis sp. PCC 6803 and E. coli, this protein sequence was back-translated and codon-optimized according to the frequency of the codon usage in Synechocystis sp. PCC 6803. The codon-optimization process was performed based on the codon usage table obtained from Kazusa DNA Research Institute, Japan (see, e.g., http://www.kazusa.or.jp/codon/), and using the "Gene Designer 2.0" software from DNA 2.0 (see, e.g., https://www.dna20.com/) at a cut-off thread of 15%. The codon-optimized gene was designed with appropriate restriction sites flanking the S-β-PHLS sequence to aid subsequent cloning steps. The nucleotide sequences of the original β-phellandrene synthase gene from *Lavandula angustifolia* (La-β-PHLS) is shown in FIG. 3B, while the codon-optimized sequence for expression in *Synechocystis* sp. PCC 6803 and *E. coli* (S-β-PHLS) is shown in FIG. 3C.

Plasmid Construction and Generation of *Synechocystis* Transformants with Heterologous Expression of the S-β-PHLS Gene A plasmid construct was generated to allow the heterologous expression of the β-phellandrene synthase gene in *Synechocystis* through the replacement of the *Synechocystis* PsbA2 gene with the Syn-β-PHLS gene via double homologous recombination. The synthesized Syn-β-PHLS was PCR amplified using the following primers: PHLS_F, 5'-CCTGGGCGGTTCTGATAACG-3' (SEQ ID NO:12), and PHLS_BamHI_R, 5'-CGCGGATCCTTTTGACGGCGGCCGCAGAT-3' (SEQ ID NO:13). A BamHI site was incorporated into the PHLS_BamHI_R primer to allow the cloning of S-β-PHLS PCR product into the NdeI and BamHI sites of the plasmid pBA2A2, which contains 500 bp of the upstream and downstream sequences of the PsbA2 gene (Lindberg et al., *Metab. Eng.*, 12:70-79 (2010)), generating plasmid pBA2SynβPHLSA2. Finally, a chloramphenicol resistance cassette from plasmid pACYC184 was PCR amplified using primers with strategically incorporated restriction sites: CamR_NotI_F, 5'-AAGGAAAAAAGCGGCCGCGTTGATCGGCACGTAAGAGGTTC-3' (SEQ ID NO:14), and CamR_BamHI_R, 5'-CGCGGATCCCCAGGCGTTTAAGGGCACCAATAAC-3' (SEQ ID NO:15), and cloned into the NotI and BamHI sites of plasmid pBA2SynβPHLSA2, to generate plasmid pBA2SynβPHLSCamRA2. This plasmid was used to transform wild-type *Synechocystis* sp. PCC 6803 according to established procedures (Williams J G K. *Methods Enzymol.*, 167:766-778 (1988); Eaton-Rye J J. *Methods Mol. Biol.*, 684:295-312 (2011)). Chloramphenicol was used for selection and maintenance of transformant strains on agar plate. The heterologous transformed *Synechocystis* PCC 6803 cyanobacteria are referred to as S-β-PHLS transformants. Successful transgene incorporation and complete DNA cyanobacterial copy segregation for the S-β-PHLS gene was verified by genomic DNA PCR, using primers designed to genomic DNA regions just outside of the upstream and downstream regions of the PsbA2 gene that were used for homologous recombination: A2us_F, 5'-TATCAGAATCCTTGCCCAGATG-3' (SEQ ID NO:16), and A2ds_R, 5'-GGTAGAGTTGCGAGGGCAAT-3' (SEQ ID NO:17).

Antibody Generation and Western Blot Analysis

For expression in *E. coli*, the *Synechocystis* codon optimized β-PHLS gene (S-β-PHLS) was PCR amplified using the forward primer 5'-GGAATTCCATATGTGTAGTTTGCAAGTTTCTGAT-3'(SEQ ID NO:18) and reverse primer 5'-ACAGGATCCTCACTCATAGCGCTCAATCAGCGT-3' (SEQ ID NO:19), and subcloned into the pET28a(+) vector (Novagen). Expression of the S-β-PHLS construct was induced by IPTG in *E. coli* BL21 (DE3) cells (Novagen), and the 6×His-tagged S-β-PHLS protein was purified under native conditions through a nickel-nitrilotriacetic acid agarose column (NTA, Qiagen) according to the manufacturer's instructions. Specific polyclonal antibodies were generated in rabbit against the full length mature β-phellandrene synthase recombinant protein as the antigen, following the instructions of ProSci Inc, USA.

Samples for SDS-PAGE analyses were prepared from *Synechocystis* cells resuspended in phosphate buffer pH 7.4 at a concentration of 0.12 mg/ml chlorophyll. The suspension was supplemented with 0.05% w/v lysozyme (Thermo Scientific) and incubated with shaking at 37° for 45 min. Cells were then pelleted at 4,000 g, washed twice with fresh phosphate buffer and disrupted with a French Pressure chamber (Aminco, USA) at 1500 psi in the presence of 1 mM PMSF. Soluble protein was separated from the total cell extract by centrifugation at 21,000 g and removed as the supernatant fraction. Samples for SDS-PAGE analysis were solubilized with 1 volume of 2× denaturing protein solubilization buffer (0.2 M Tris, pH 6.8, 4% SDS, 2 M urea, 1 mM EDTA and 20% glycerol). In addition, all samples in denaturing solutions were supplemented with a 5% (v/v) of β-mercaptoethanol and centrifuged at 17,900 g for 5 min prior to gel loading. For Western blot analyses, Any kD™ (BIO-RAD) precast SDS-PAGE gels were utilized to resolve proteins, which were then transferred to PVDF membrane (Immobilon-FL 0.45 μm, Millipore, USA) for immunodetection using the rabbit immune serum containing specific polyclonal antibodies against the S-β-PHLS protein. Cross-reactions were visualized by Supersignal West Pico Chemiluminiscent substrate detection system (Thermo Scientific, USA).

Chlorophyll Determination, Photosynthetic Productivity and Biomass Quantitation

Chlorophyll a concentrations in cultures were determined spectrophotometrically in 90% methanol extracts of the cells according to Meeks and Castenholz (Arch. Mikrobiol., 78:25-41 (1971)). Photosynthetic productivity of the cultures was tested polarographically with a Clark-type oxygen electrode (Rank Brothers, Cambridge, England). Cells were harvested at mid-exponential growth phase, and maintained at 25° C. in BG11 containing 25 mM HEPES-NaOH, pH 7.5, at a chlorophyll a concentration of 10 μg/mL. Oxygen evolution was measured at 25° C. in the electrode upon yellow actinic illumination, which was defined by a CS 3-69 long wavelength pass cutoff filter (Corning, Corning, N.Y.). Photosynthetic activity of a 5 mL aliquot of culture was measured at varying actinic light intensities in the presence of 15 mM $NaHCO_3$ pH 7.4, to generate the light saturation curve of photosynthesis. Culture biomass accumulation was measured gravimetrically as dry cell weight, where κ mL samples of culture were filtered through 0.22 μm Millipore filters and the immobilized cells dried at 90° C. for κ h prior to weighing the dry cell weight.

β-Phellandrene Production and Quantification Assays

*Synechocystis* cultures for β-phellandrene production assays were grown photoautotrophically in 1 L gaseous/aqueous two-phase photobioreactors, described in detail by Bentley and Melis (*Biotechnol Bioeng.*, 109:100-109 (2012)). Bioreactors were seeded with a 700 ml culture of *Synechocystis* cells at an OD730 nm of 0.05 in BG11 medium containing 25 mM sodium phosphate buffer, pH 7.5, and grown under continuous illumination at 75 μmol photons $m^{-2}$ $s^{-1}$, and continuous bubbling with air, until an OD730 nm of approximately 0.5 was reached. Inorganic carbon was delivered to the culture in the form of 500 mL aliquots of 100% $CO_2$ gas, which was slowly bubbled though the bottom of the liquid culture to fill the bioreactor headspace. Once atmospheric gases were replaced with 100% $CO_2$, the headspace of the reactor was sealed and the culture was incubated under continuous illumination of 150 μmol photons $m^{-2}$ $s^{-1}$ at 35° C. Slow continuous mechanical mixing was employed to keep cells in suspension and to promote balanced cell illumination and nutrient mixing into the liquid culture in support of photosynthesis and biomass accumulation. Uptake and assimilation of headspace $CO_2$ by cells was concomitantly exchanged for $O_2$ during photoautotrophic growth. The sealed bioreactor headspace allowed for the trapping, accumulation and concentration of photosynthetically produced β-phellandrene, as either a volatile product in the headspace, or in liquid form floating on the aqueous phase.

Gas from the headspace of sealed bioreactors was sampled and analyzed by gas chromatography-mass spectrometry (GC-MS) in an effort to detect volatilized, photosynthetically produced monoterpene hydrocarbons (β-phellandrene). Comparison of retention time and mass spectrum with a vaporized mixture of α-phellandrene and β-phellandrene standard (MP Biomedicals) allowed for positive identification of β-phellandrene in the headspace. Photosynthetically produced non-miscible β-phellandrene in liquid form was extracted from the liquid phase upon overlaying 20 mL heptane on top of the liquid culture in the bioreactor, and upon incubating for 30 min, or longer, at room temperature. The heptane layer was subsequently removed and analysed by GC-MS for the detection of β-phellandrene by comparison with the liquid α-phellandrene and β-phellandrene standard also dissolved in heptane. GC-MS analyses were performed with an Agilent 6890GC/5973 MSD equipped with a DB-XLB column (0.25 mm i.d.×0.25 µm×30 m, J &W Scientific). Oven temperature was initially maintained at 40° C. for 4 min, followed by a temperature increase of 5° C./min to 80° C., and a carrier gas (helium) flow rate of 1.2 ml per minute.

Accumulation of β-phellandrene in the liquid phase was quantified spectrophotometrically according to known absorbance spectra and extinction coefficients of β-phellandrene in organic solvents (Macbeth et al., *J. Chem. Soc.* 119-123 (1938); Booker et al., *J. Chem. Soc.* 1453-1463 (1940); Gross K P, Schnepp O., *J. Chem. Phys.* 68:2647-2657 (1978)). The majority of photosynthetically produced β-phellandrene accumulated as a liquid floating over the aqueous phase of the bioreactor. Therefore, the non-miscible, heptane-extracted β-phellandrene was used to generate the absorption spectra of β-phellandrene in heptane for quantification purposes.

Results

The native *L. angustifolia* cDNA sequence has a codon usage different from that preferred by photosynthetic microorganisms, e.g., cyanobacteria and microalgae. The unicellular cyanobacteria *Synechocystis* sp. were used as a model organism in the development of the present invention. A de novo codon-optimized β-PHLS gene was designed and synthesized. In the optimized version of the gene, termed S-β-PHLS, the codon usage was adapted to eliminate codons rarely used in *Synechocystis*, and to adjust the AT/GC ratio to that of the host. Rare codons were defined using a codon usage table derived from the sequenced genome of *Synechocystis*. The β-phellandrene synthase sequences used in this example were: the β-PHLS protein sequence for expression in *Synechocystis* and *E. coli* (S-β-PHLS), the native *L. angustifolia* β-PHLS cDNA sequence including the predicted chloroplast transit peptide (GenBank Accession No. HQ404305), and the *L. angustifolia* β-PHLS cDNA sequence minus the chloroplast transit peptide, with codon usage optimized for *Synechocystis* (S-β-PHLS). In the native *L. angustifolia* β-PHLS sequence a substantial number of codons are present that are used with a frequency of less than 15% by *Synechocystis*. In the codon-optimized gene, such low-frequency codons were not allowed.

Figure 6:
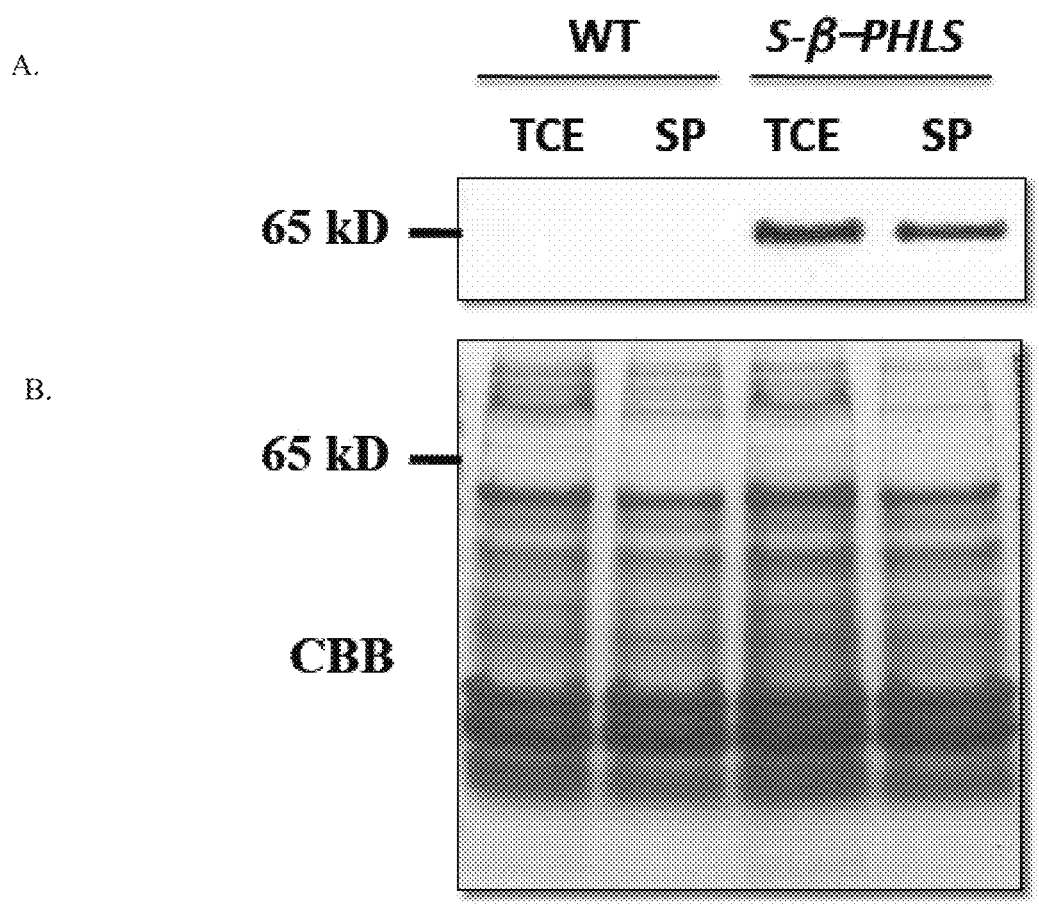
FIG. 6. Western blot analysis of the S-β-PHLS protein in transformant *Synechocystis* cells. (A) Western blot analysis of wild type (WT) and S-β-PHLS transformant cells probed with β-PHLS specific polyclonal antibodies. Lanes were loaded with a total cell extract (TCE) sample, or the soluble fraction of *Synechocystis* cells (SP) as obtained by collection of the supernatant following cell disruption and centrifugation to pellet insoluble material. (B) Coomassie-stained SDS-PAGE gel corresponding to the protein profile of the Western blot in panel A, shown as a control for protein loading.

SDS-PAGE analyses and immuno-detection of the β-phellandrene synthase enzyme, using specific polyclonal antibodies raised against the *E. coli*-expressed recombinant protein, confirmed the presence of the S-β-PHLS protein in *Synechocystis* (FIG. 6). The S-β-PHLS protein was localized in the soluble fraction of *Synechocystis* cell extracts, consistent with the notion of a soluble protein. FIG. 6 (top panel) shows the absence of cross-reaction between the anti-S-β-PHLS polyclonal antibodies and any protein of the *Synechocysis* wild type (WT) in the total cell extract (TCE) or supernatant (SP) fractions. However, a specific cross-reaction was observed between the anti-S-β-PHLS polyclonal antibodies and a protein band at about 65 kD in both of the total cell extract (TCE) and supernatant fractions (SP) of the S-β-PHLS transformant. These results clearly show that the recombinant S-β-PHLS protein was expressed in *Synechocystis* transformants, and that it accumulated as a soluble protein in the cell.

The above results demonstrated that *Synechocystis* can be used for heterologous transformation using aβ-PHLS gene, and that such transformants expressed and accumulated the S-β-PHLS protein in their cytosol. To determine whether the expressed S-β-PHLS protein is metabolically competent, wild type and S-β-PHLS transformants were cultivated under the conditions of the gaseous/aqueous two-phase bioreactor (Bentley F K and Melis A., *Biotechnol Bioeng.*, 109:100-109 (2012)), with 100% $CO_2$ gas occupying the headspace prior to sealing the reactor to allow autotrophic biomass accumulation. Samples were obtained from both the headspace of sealed cultures (to detect vaporized β-phellandrene) and from the surface of liquid cultures (to detect non-miscible liquid β-phellandrene floating on top of the aqueous phase) and analyzed by GC-MS.

Figure 7:
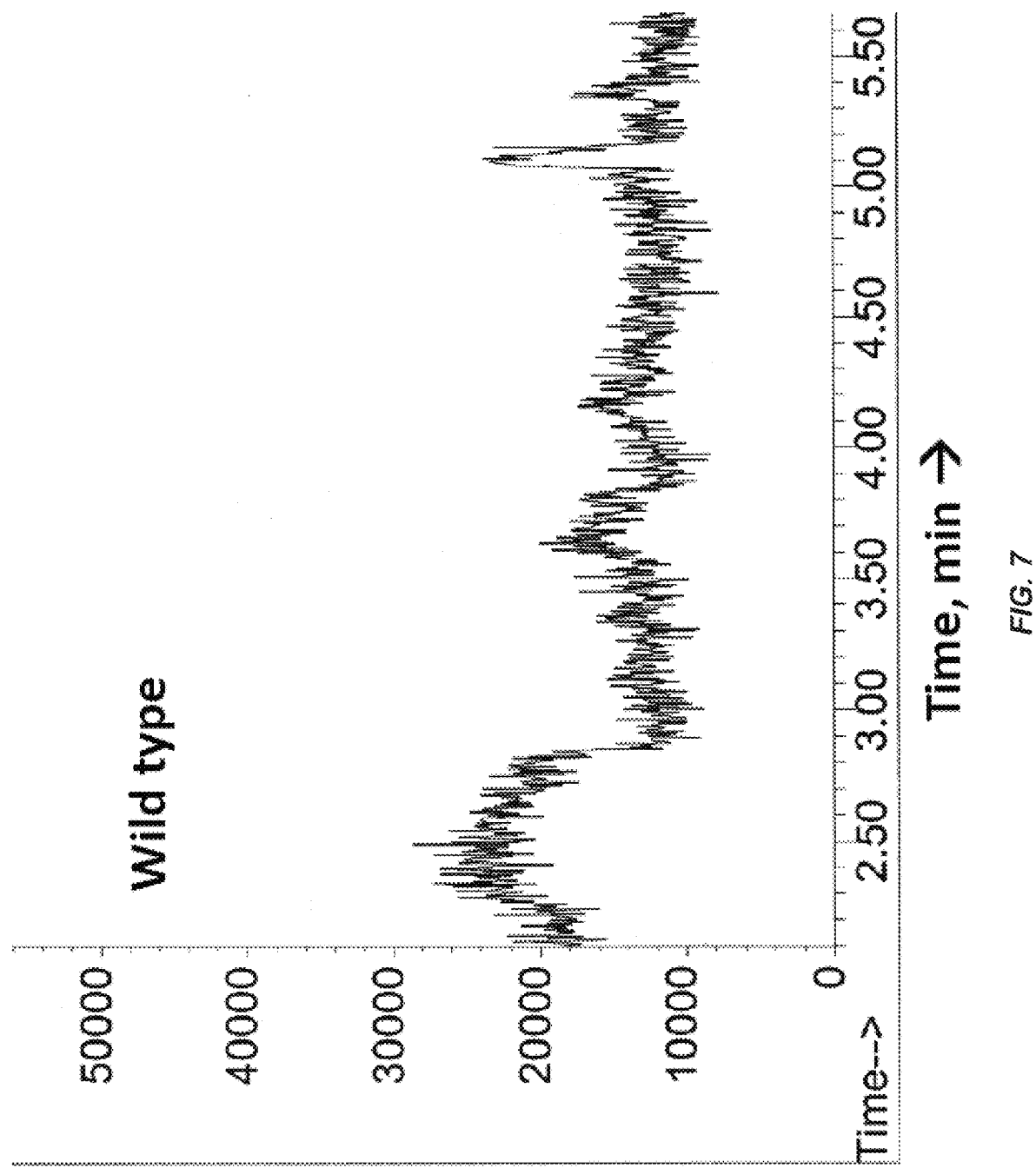
FIG. 7. GC-MS analyses of gases from the headspace of wild type culture. Accumulated headspace gases in sealed cultures were analyzed by GC-MS following 48 h of photoautotrophic growth in the presence of $CO_2$ in gaseous/aqueous two-phase bioreactors. GC profile of gasses from wild-type culture.
Figure 8:
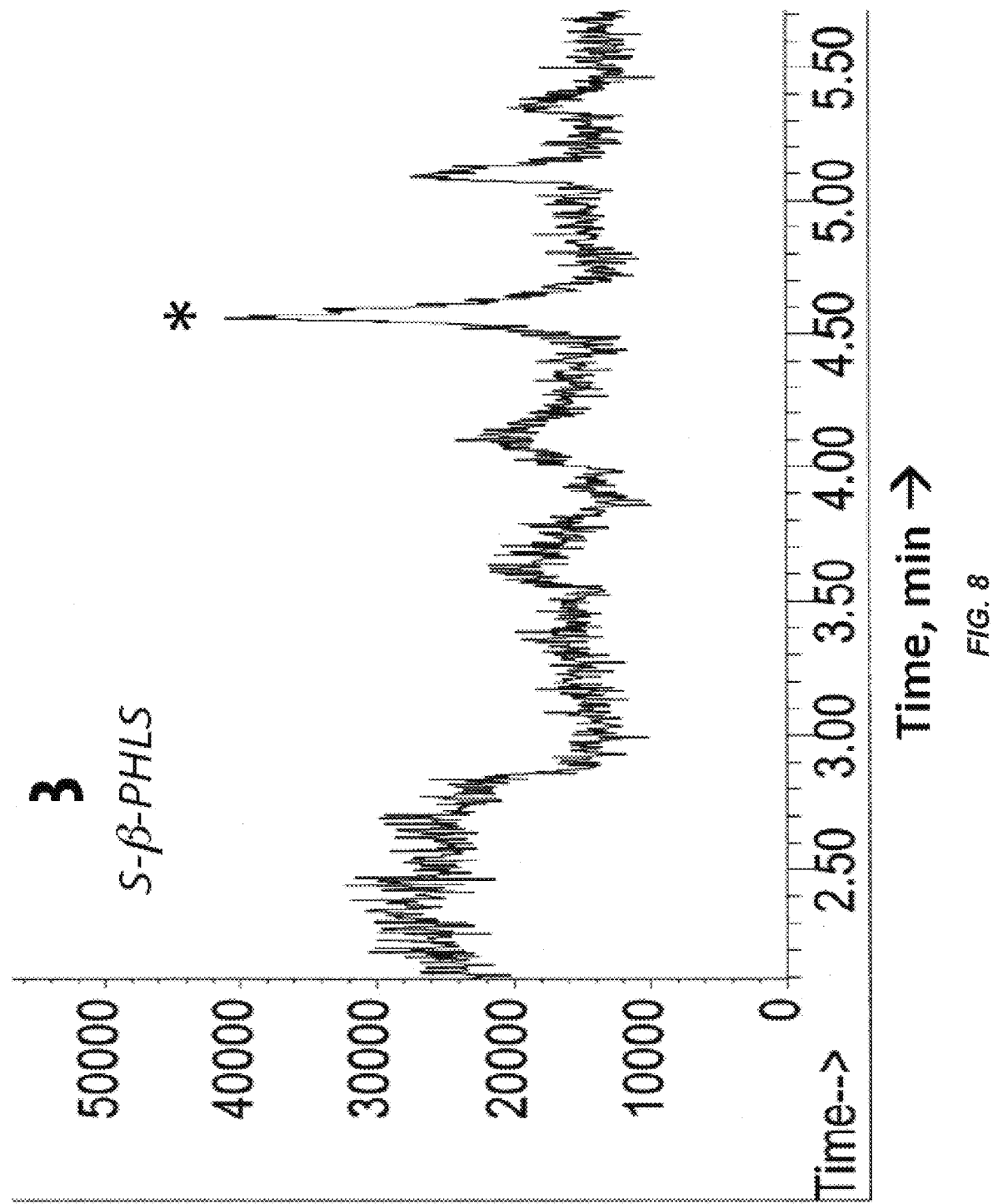
FIG. 8. GC-MS analyses of gases from the headspace of S-β-PHLS transformant culture. Accumulated headspace gases in sealed cultures were analyzed by GC-MS following 48 h of photoautotrophic growth in the presence of $CO_2$ in gaseous/aqueous two-phase bioreactors. GC profile of gasses from S-β-PHLS transformant culture. The β-phellandrene peak is labeled with asterisks and has a retention time of around 4.6 min.
Figure 9:
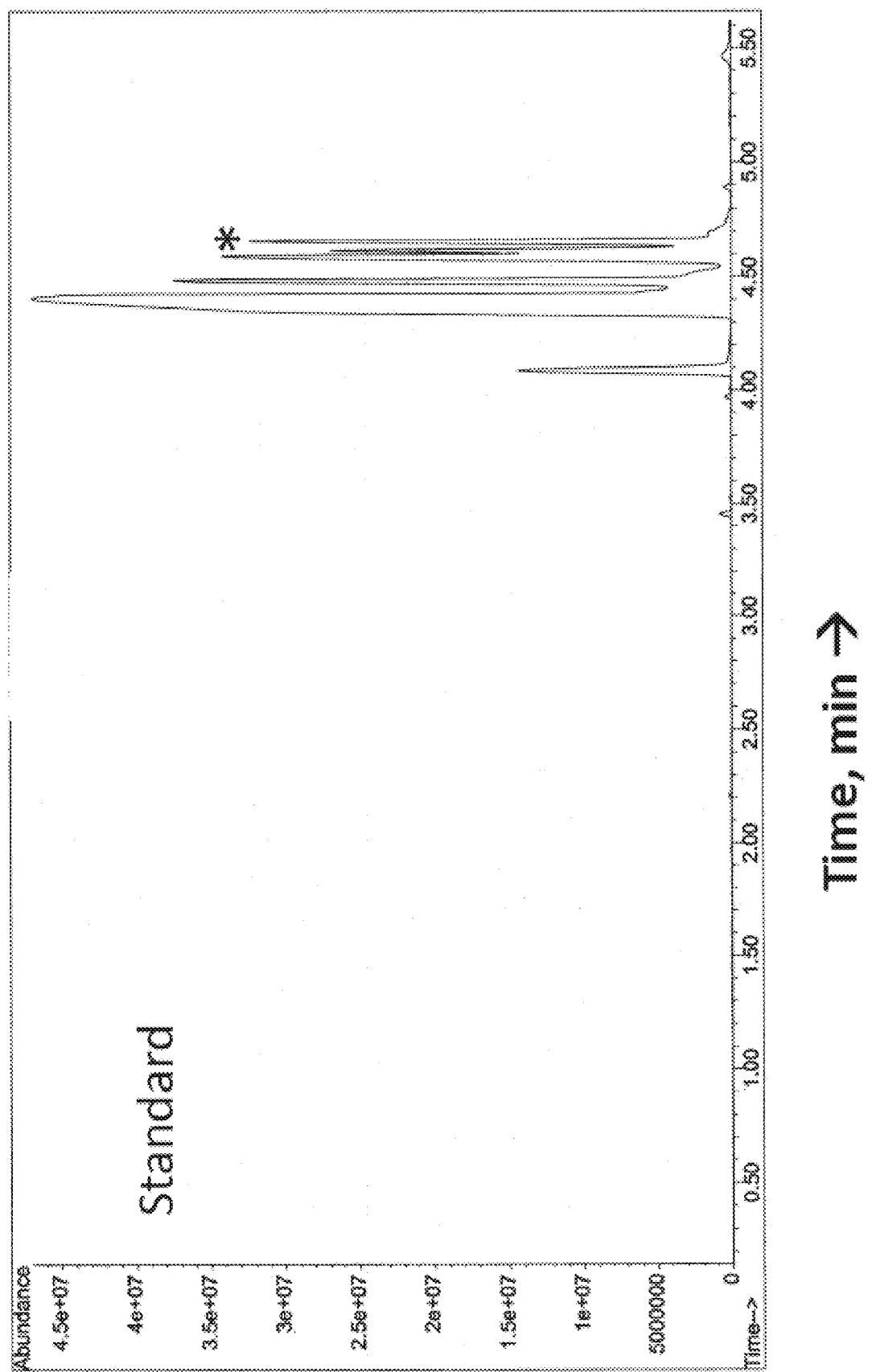
FIG. 9. GC profile of gasses from a vaporized α-phellandrene standard (containing β-phellandrene as a contaminant). The β-phellandrene peak is labeled with asterisks and has a retention time of around 4.6 min.
Figure 10:
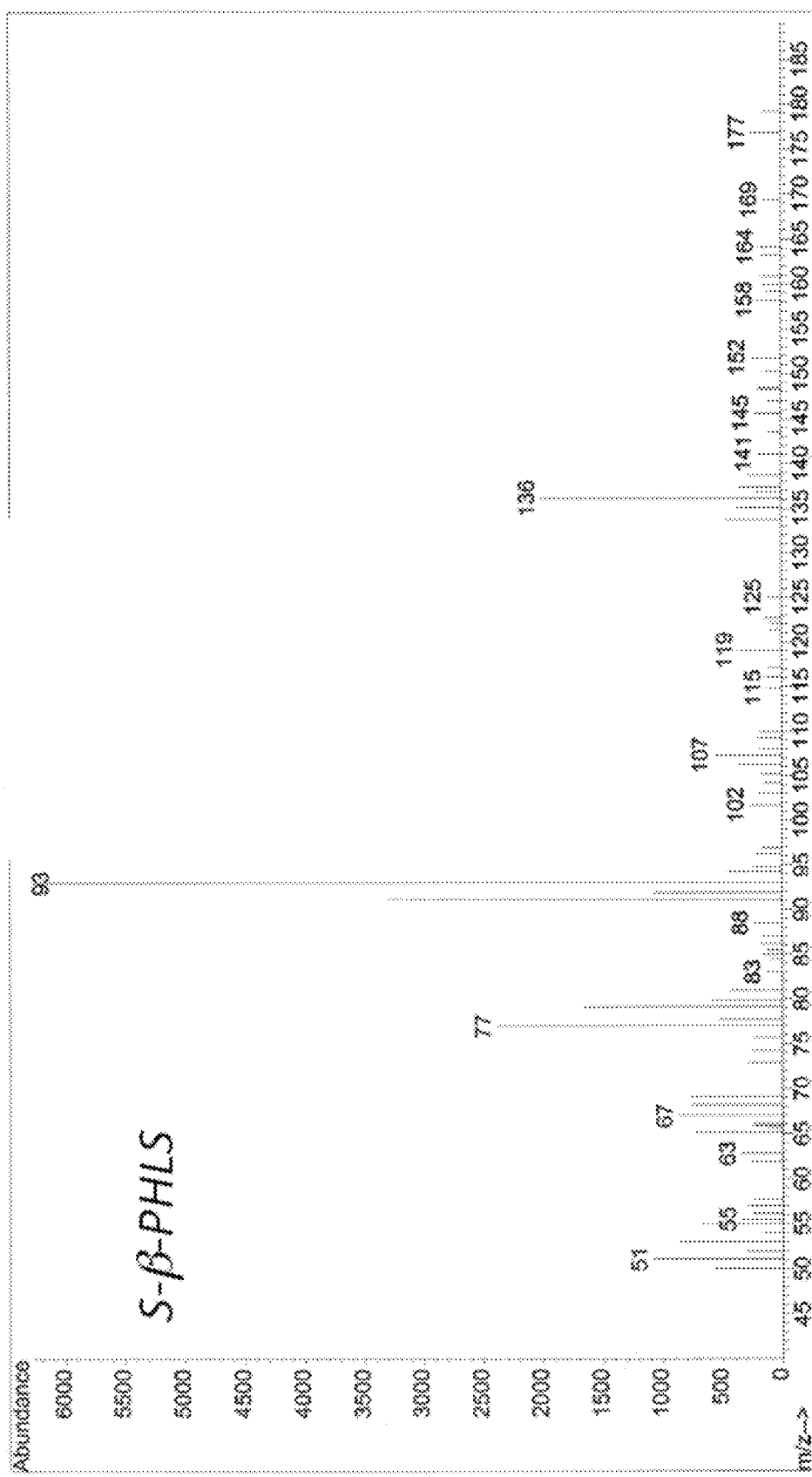
FIG. 10. GC-MS analyses of gases from the headspace of an S-β-PHLS culture. Accumulated headspace gases in sealed cultures were analyzed by GC-MS following 48 h of photoautotrophic growth in the presence of $CO_2$ in gaseous/aqueous two-phase bioreactors. MS analysis of the products eluted at 4.6 min in the S-β-PHLS transformant culture showing the signature [77, 91, 93 and 136] MS lines of β-phellandrene.
Figure 11:
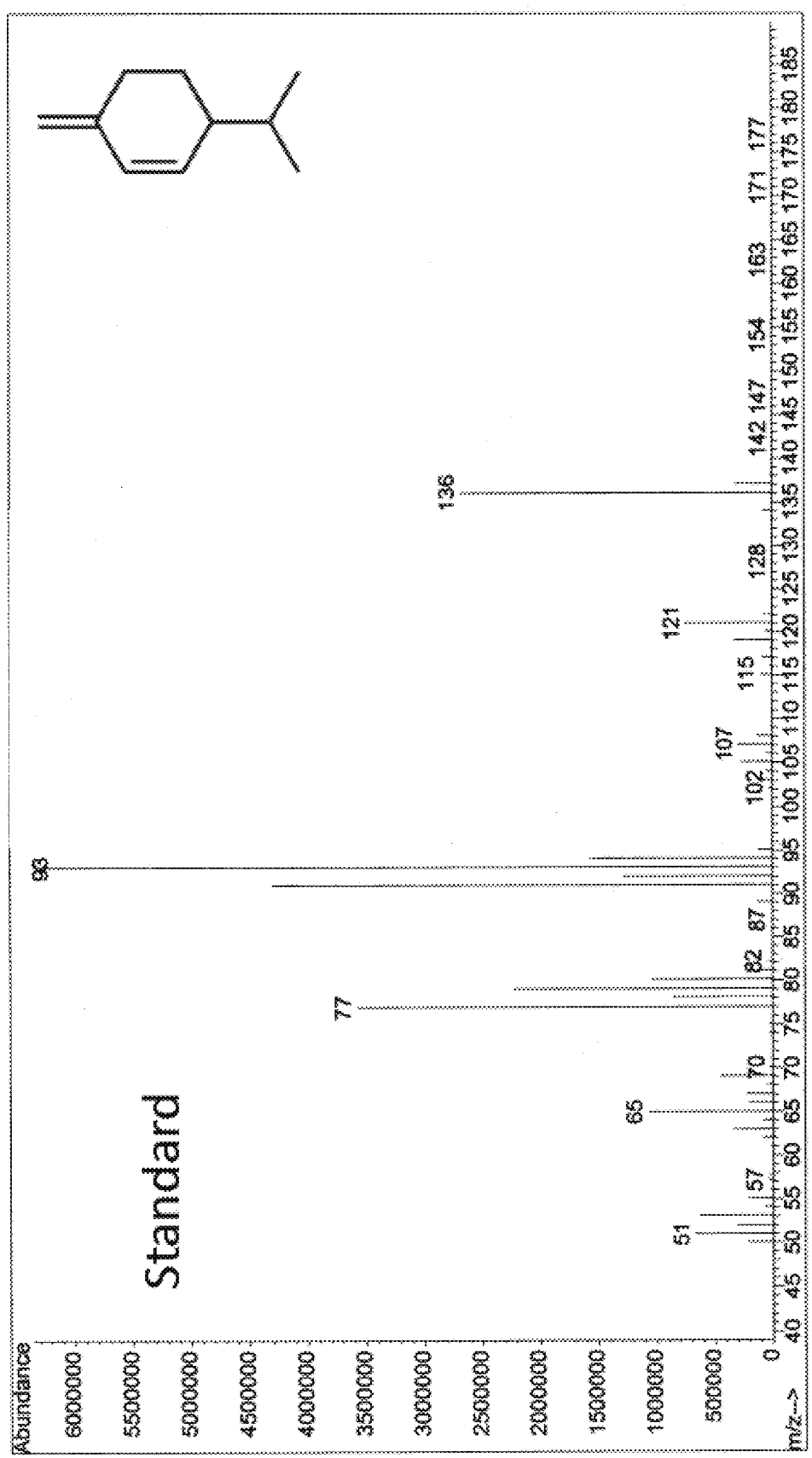
FIG. 11. MS analysis of the products eluted at 4.6 min with a contaminating β-phellandrene peak in the standard solution.

Analysis of the accumulated reactor headspace gases in the wild type after 48 h incubation showed no evidence of β-phellandrene hydrocarbons (FIG. 7). The headspace of the S-β-PHLS transformant, however, showed β-phellandrene accumulation, as evidenced by the GC peak with a 4.6 min retention time (FIG. 8, asterisk), which is comparable to the retention time of the β-phellandrene peak observed in the phellandrene standard (FIG. 9, asterisk). A supply of commercially available pure β-phellandrene standard was difficult to source, therefore we opted to use a commercially-available α-phellandrene standard. Upon GC-MS analysis of the standard, a major peak was identified as α-phellandrene, however, the MS-analysis indicated presence of a number of other monoterpene impurities, including β-myrcene, 2-carene, benzene, eucalyptol and β-phellandrene (FIG. 9). Accordingly, we employed the β-phellandrene peak in the standard as a reference for identification of β-phellandrene produced by the *Synechocystis* transformant cultures. The height of the β-phellandrene peak from the gas sample of the S-β-PHLS transformant clearly showed that β-phellandrene was the major volatile hydrocarbon generated by photosynthesis in the transformant (FIG. 8). This peak was positively identified as β-phellandrene by comparison of its mass spectrum with the β-phellandrene peak in the standard sample, showing distinct mass spectral lines [77, 91, 93 and 136] that signify β-phellandrene hydrocarbons (FIGS. 10 and 11). These results provided evidence that the S-β-PHLS transgene and its encoded β-phellandrene synthase enzyme were responsible for the catalysis of β-phellandrene production in the transformant *Synechocystis* strains.

Unlike molecular hydrogen ($H_2$) and isoprene hydrocarbons ($C_5H_8$), which are small and easily escape from the cells that produce them (Melis A., *Energy Environ. Sci.*, 5(2): 5531-5539; (2012)), monoterpene hydrocarbons, including β-phellandrene, are large enough to be trapped in the hydrophobic domain of the cell's lipid bilayers. Such outcome would most likely have very adverse consequences for cell growth and fitness. Accordingly, our efforts have focused to investigate whether the cells can freely emit β-phellandrene, and whether cell growth and properties of photosynthesis are adversely affected in the S-β-PHLS transformants.

Figure 12:
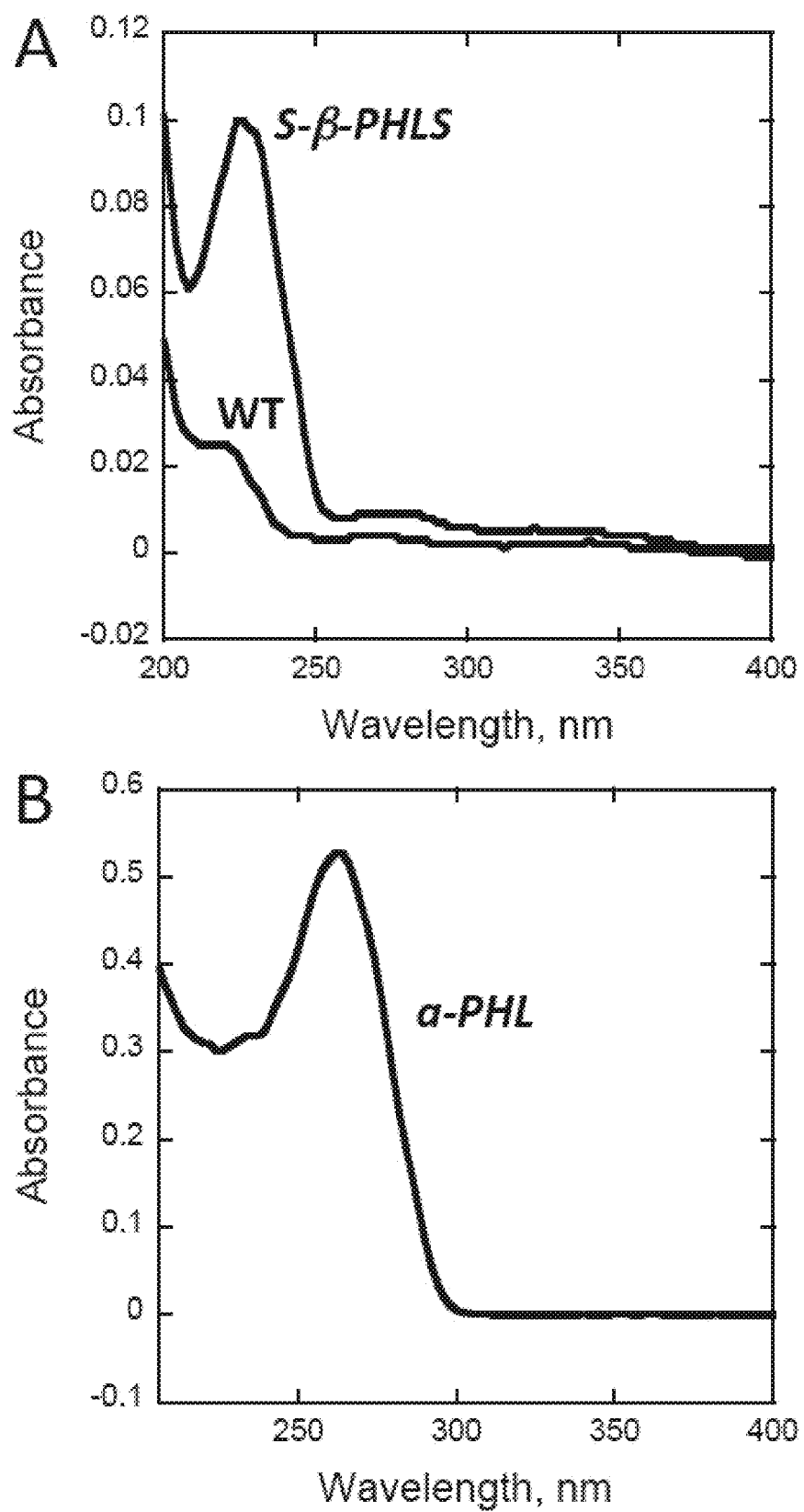
FIG. 12. Absorbance spectra of phellandrene hydrocarbons in heptane. (Panel A) Absorbance spectra of heptane-extracted samples from the surface of wild type (black) and S-β-PHLS transformant (S-β-PHLS) liquid cultures. The β-phellandrene absorbance peak is observed at 230 nm, exclusively in the heptane extracts from the S-β-PHLS cultures. (Panel B) Absorbance spectra of the α-phellandrene standard diluted in heptane. The α-phellandrene absorbance peak is observed at 260 nm.

Monoterpene hydrocarbons have a relatively high boiling point (170-175° C.) and are non-miscible in aqueous solution. If freely emitted by the transformant photosynthetic microorganisms, one would expect that monoterpene molecules, including β-phellandrene, would float on the aqueous phase of the reactor. Surprisingly, this was indeed observed in the case of β-phellandrene, produced by the transformed cyanobacteria. A small volume of heptane was layered on top of the liquid culture to trap non-miscible liquid hydrocarbons, such as β-phellandrene, floating on the surface of the culture, and spectrophotometic analyses were performed as the method for β-phellandrene quantification. FIG. 12A shows representative absorbance spectra of heptane-extracted samples from wild type (WT) and S-β-PHLS transformant cultures. The absorbance maximum of β-phellandrene occurs at 230 nm (Macbeth et al., *J. Chem. Soc.*, 119-123 (1938); Booker et al., *J. Chem. Soc.*, 1453-1463 (1940); Gross K P and Schnepp O., *J. Chem. Phys.*, 68:2647-2657 (1978)). A well-defined band peaking at 230 nm was observed in the heptane extracts of S-β-PHLS-transformants, while absent in wild-type samples. Importantly, α-phellandrene has an absorbance maximum of 260 nm (Macbeth et al., *J. Chem. Soc.*, 119-123 (1938); Booker et al., *J. Chem. Soc.*, 1453-1463 (1940); Gross K P and Schnepp O., *J. Chem. Phys.*, 68:2647-2657 (1978)), which allows β-phellandrene to be easily distinguished from α-phellandrene using the spectrophotometric method. FIG. 12B shows the absorbance spectrum of the liquid α-phellandrene standard (used for the GC-MS analyses, e.g. FIG. 9) diluted in heptane with its absorbance maximum of 260 nm. The absence of absorbance peaks at 260 nm in the S-β-PHLS transformants (FIG. 12A) indicated that little, if any, α-phellandrene accumulated as a non-miscible product of photosynthesis in transformant lines, and that β-phellandrene exclusively accumulated in more substantial quantities.

Quantification of β-phellandrene in the heptane-extracted samples from S-β-PHLS transformants was determined according to the Beer-Lambert Law, using the absorbance values measured at 230 nm and the known molar extinction coefficient of β-phellandrene. During 48 h of active photoautotrophic growth in the presence of $CO_2$ in a sealed gaseous/aqueous two-phase bioreactor, a 700 ml culture of S-β-PHLS transformant produced β-phellandrene in the form of a non-miscible product floating on the surface of the culture.

Figure 13:
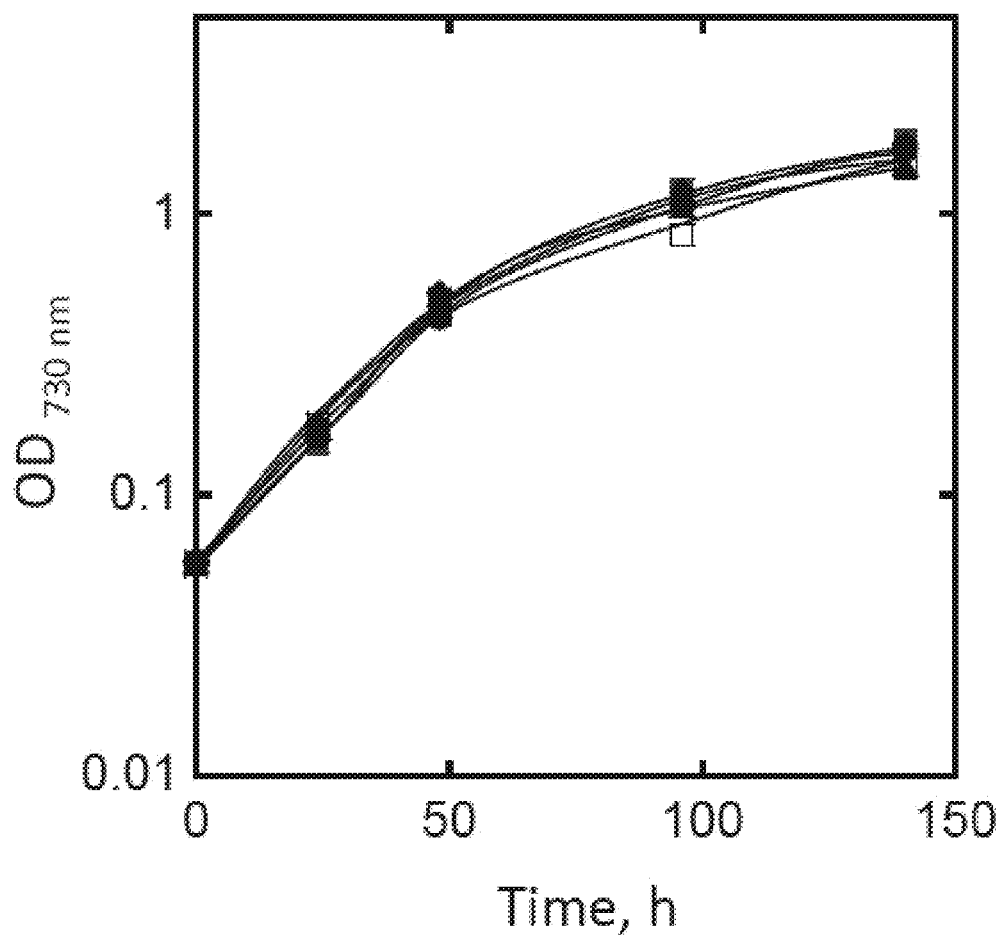
FIG. 13. Comparative photoautotrophic growth measurements of wild type and S-β-PHLS transformants in liquid culture. Photoautotrophic growth kinetics of wild type (open squares) and four different S-β-PHLS transformant lines (closed squares, circles, diamonds and triangles), as measured by optical density of the culture at 730 nm. Cultures were grown under conditions of continuous aeration and illumination at 20 μmol photons $m^{-2}$ $s^{-1}$.
Figure 14:
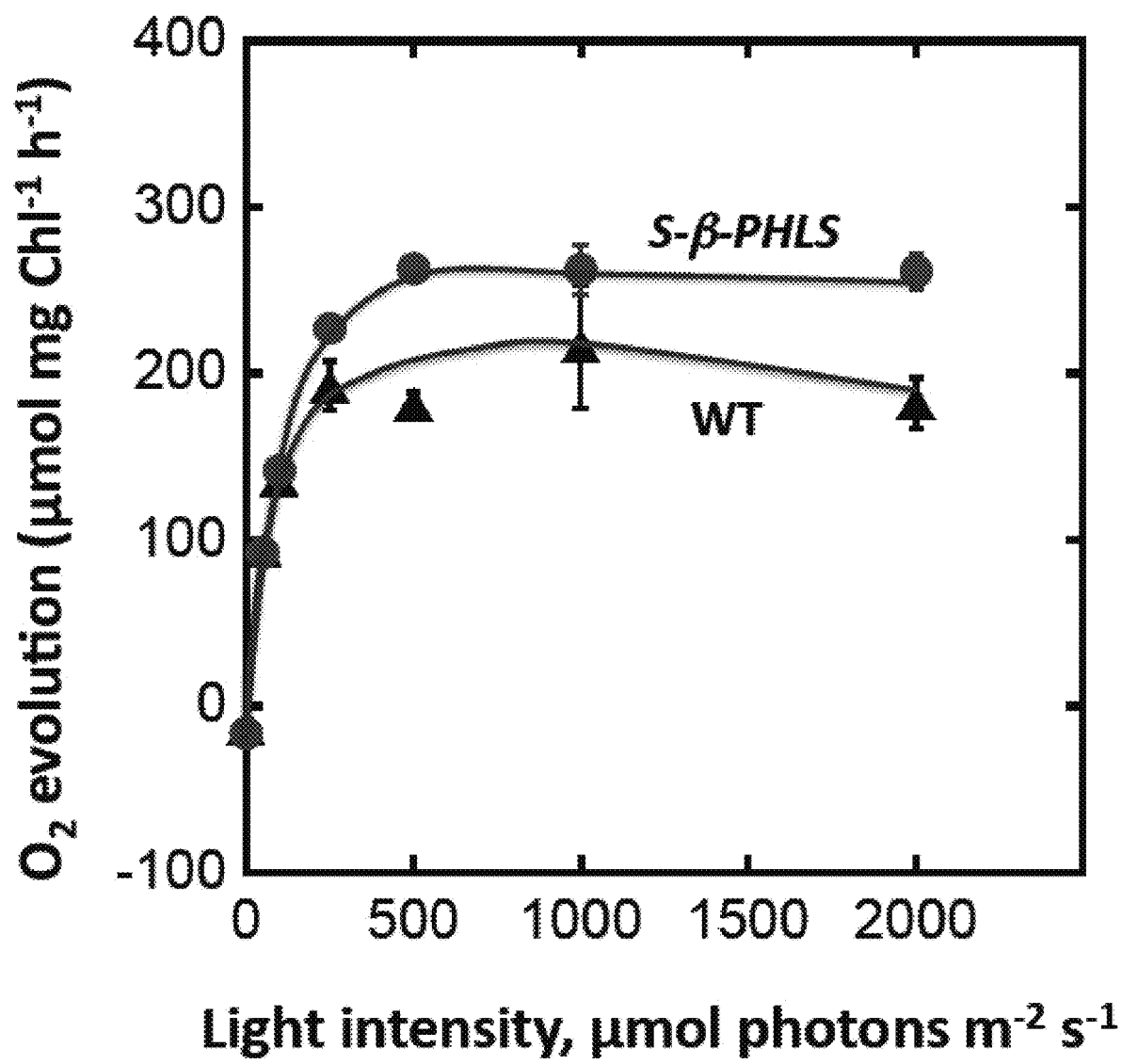
FIG. 14. Quantum yields of photosynthesis as measured by oxygen evolution in wild type and S-β-PHLS transformants in liquid culture. Light saturation curves of photosynthesis for wild type and S-β-PHLS transformant cells, as measured by the oxygen-evolution activity of an aliquot of the cultures incubated in the presence of 15 mM $NaHCO_3$, pH 7.4 under a range of actinic light intensities.

The photoautotrophic cell growth kinetics of the S-β-PHLS transformants were similar to those of the wild type, with a cell doubling time of 16 h under a light intensity of 20 µmol photons $m^{-2}$ $s^{-1}$ under continuous bubbling with air (FIG. 13). The light saturation curves of photosynthesis of wild type and the S-β-PHLS transformants were also similar to one another (FIG. 14), where oxygen evolution saturated at about 500 µmol photons $m^{-2}$ $s^{-1}$, with an average $P_{max}$ of 216 µmol $O_2$ (mg Chl)$^{-1}$ $h^{-1}$ in wild type and 263 µmol $O_2$ (mg Chl)$^{-1}$ $h^{-1}$ in the S-β-PHLS transformant (FIG. 14). Similarly, rates of oxygen consumption during dark respiration were about the same in the wild type and S-β-PHLS transformants and equal to about −14 µmol $O_2$ (mg Chl)$^{-1}$ $h^{-1}$. Importantly, at sub-saturating light intensities between 0 and 250 µmol photons $m^{-2}$ $s^{-1}$, rates of oxygen evolution and the initial slopes of photosynthesis as a function of light intensity were comparable in wild-type and S-β-PHLS-transformant cells (FIG. 14), suggesting similar quantum yields of photosynthesis for the two strains (Melis A., *Plant Science*, 177:272-280 (2009)). These results demonstrated that deletion of the endogenous PsbA2 coding region from the *Synechocystis* genome, with the attendant replacement/integration and expression of the S-β-PHLS transgene in the cell, as well as the subsequent generation and accumulation of β-phellandrene, had no adverse effects on the photoautotrophic growth parameters of the transformants.

Figure 15:
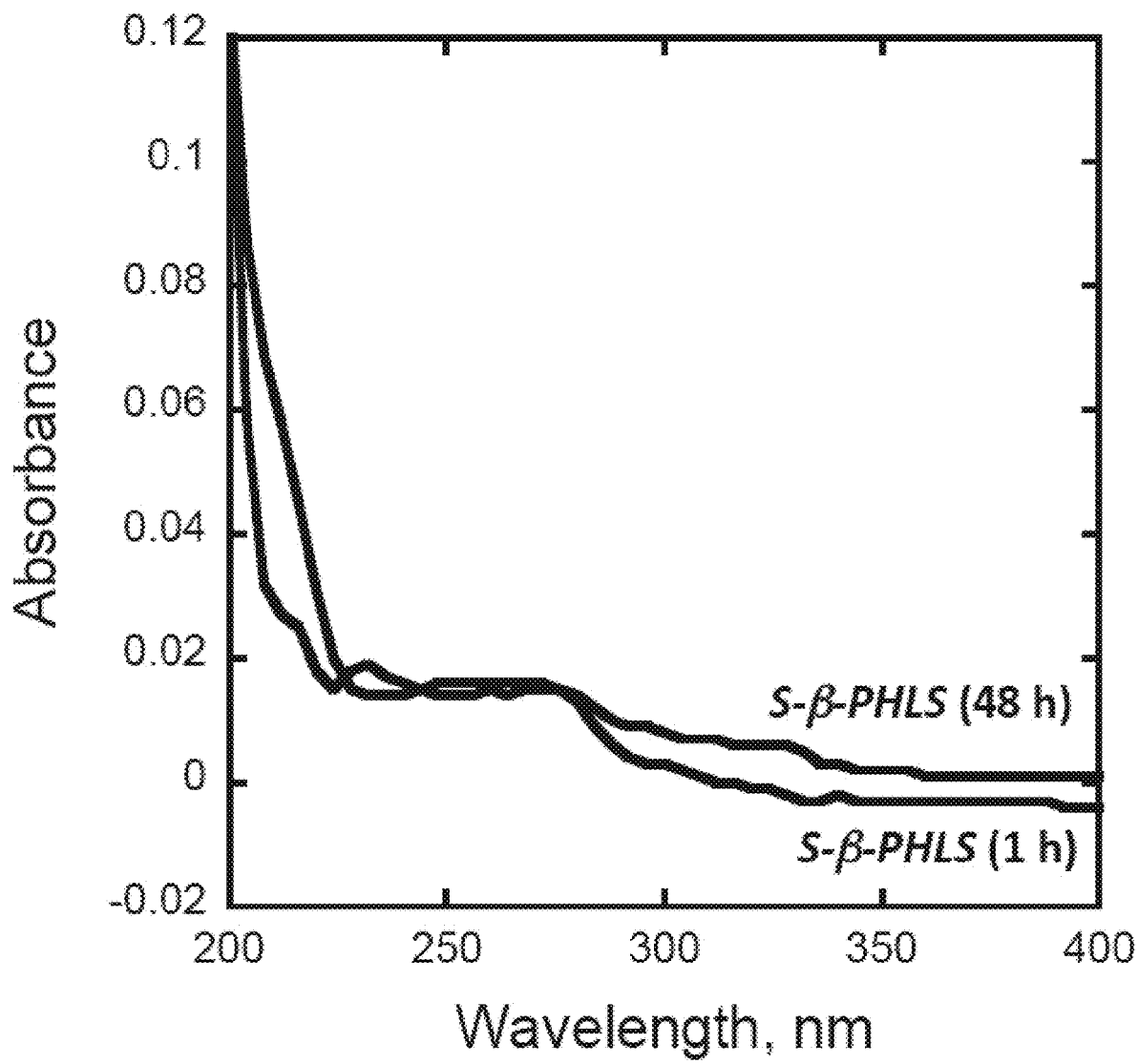
FIG. 15. Absence of β-phellandrene hydrocarbons in heptane extracts from the surface of *Escherichia coli* cultures induced by isopropyl β-D-1-thiogalactopyranoside (IPTG) and over-expressing the β-phellandrene protein. Absorbance spectra of heptane-extracted samples from the surface of *E. coli* liquid cultures, measured in the wavelength region between 200 and 400 nm. Extraction time of cultures, i.e., application of the heptane solvent on the surface of the liquid phase of IPTG-induced cultures, was either 1 h or 48 h. No distinctive β-phellandrene absorbance peak could be observed at 230 nm from these β-PHLS cultures, as compared to that of FIG. 12.

The β-phellandrene synthase protein has been successfully over-expressed in *E. coli* (Demissie et al., *Planta*, 233:685-696 (2011)). However, only in vitro enzymatic assays were performed with the β-phellandrene synthase recombinant protein. This suggests that there was little β-phellandrene in *E. coli* and/or limited or no efflux of β-phellandrene from *E. coli* and/or adverse effects of the β-phellandrene synthase protein or of its product on the *E. coli* host cells. Absence of β-phellandrene hydrocarbons in heptane extracts from the surface of IPTG-induced β-PHLS-transformed *Escherichia coli* cultures was also observed in the illustrative experiments described herein (FIG. 15). In this study, transformant *E. coli* cells were induced by isopropyl β-D-1-thiogalactopyranoside (IPTG), resulting in the over-expression of the β-phellandrene protein. Absorbance spectra of heptane-extracted samples from the surface of such *E. coli* liquid cultures failed to show the presence of the β-phellandrene molecule. No distinctive β-phellandrene absorbance peak could be observed at 230 nm from the β-PHLS *E. coli* cultures (compare with the results of FIG. 12A).

DISCUSSION

"Photosynthetic biofuels", as defined in the present invention, are produced in a system where the same organism serves both as photo-catalyst and producer of ready-made fuel or chemical. A number of guiding principles have been applied in the endeavor of photosynthetic biofuels, as they pertain to the selection of organisms and, independently, to the selection of potential biofuels. Criteria for the selection of organisms include, foremost, the solar-to-biofuel energy conversion efficiency, which must be as high as possible. This important criterion is better satisfied with photosynthetic microorganisms than with crop plants (Melis A., Plant Science, 177:272-280 (2009)). Criteria for the selection of potential biofuels include (i) the relative energy content and potential utility of the molecule. Pure hydrocarbons are preferred over sugars or alcohols because of the greater relative energy stored in hydrocarbon molecules (Schakel et al., *J. Food Comp. Anal.*, 10:102-114 (1997); Berg J, Tymoczko J L, Stryer L. (2002) *Biochemistry* (5th ed.). W. H. Freeman, San Francisco, Calif. p. 603.); and (ii) the question of product separation from the biomass, which enters prominently in the economics of the process and is a most important aspect in commercial application. This example demonstrates that β-phellandrene is suitable in this respect, as it is not miscible in water, spontaneously separating from the biomass and end-up floating on the aqueous phase of the reactor and culture that produced them. Such spontaneous product separation from the liquid culture alleviates the requirement of time-consuming, expensive, and technologically complex biomass dewatering (Danquah et al., *J Chem*

Tech. Biotech., 84:1078-1083 (2009); Saveyn et al., J. Res. Sci Tech., 6:51-56 (2009)) and product excision from the cells that otherwise would be needed for product isolation.

In the pursuit of renewable biofuels, photosynthesis, cyanobacteria or microalgae and β-phellandrene meet the above-enumerated criteria for "process", "organism" and "product", respectively. This example shows that β-phellandrene can be heterologously produced via photosynthesis in microorganisms, e.g., cyanobacteria, genetically engineered to express a plant β-phellandrene synthase. In this example, the *Lavandular angustifolia* β-PHLS gene was employed via heterologous expression in *Synechocystis*. The DNA sequence of the *Lavandular* β-PHLS gene was optimized for *Synechocystis* codon-usage. A diffusion-based method for spontaneous gas exchange in gaseous/aqueous two-phase photobioreactors was employed, using carbon dioxide as a feedstock for the photosynthetic generation of β-phellandrene. The headspace of the bioreactor was filled with 100% $CO_2$ and sealed, allowing the diffusion-based $CO_2$ uptake and assimilation by the cells via photosynthesis, and the concomitant replacement of the $CO_2$ in the headspace with β-phellandrene vapour and $O_2$. A considerable amount of photosynthetically generated β-phellandrene accumulated as a non-miscible product floating on the top of the liquid culture, which is explained as β-phellandrene has a boiling point of 171° C.

In the plasmid constructs employed for the expression of the β-phellandrene synthase in *Synechocystis*, we used the PsbA2 gene locus for insertion of the transgenes. Upon transformation of *Synechocystis* with these constructs, the β-PHLS gene replaced the coding sequence of the PsbA2 gene, and the PsbA2 promoter was used to drive expression of β-PHLS. The PsbA2 gene is one of three homologous genes in cyanobacteria, the other two being PsbA1 and PsbA3, that encode the 32 kD/D1 reaction center protein of photosystem-II. The promoter region and regulation of expression of the PsbA2 gene has been characterized (Eriksson et al., *Mol. Cell Biol. Res. Commun.*, 3:292-8 (2000); Mohamed et al., *Mol Gen Genet.*, 238:161-8 (1993); Mohamed A, Jansson C., *Plant Mol. Biol.* 13:693-700 (1989)). It has also been shown that a knock-out mutant of either PsbA2 or PsbA3 is able to grow photoautotrophically, provided that the other PsbA genes are still active, while PsbA1 on its own was not able to compensate for the loss of both PsbA2 and PsbA3 (Mohamed A, Jansson C., *Plant Mol. Biol.* 13:693-700 (1989)). Inactivation of PsbA2 resulted in a strong up-regulation of PsbA3 (Mohamed et al., *Mol Gen Genet.*, 238:161-8 (1993)). This example illustrates that replacement of PsbA2 by the codon-optimized β-PHLS gene does not significantly alter normal photoautotrophic growth of the transformants.

The monoterpene β-phellandrene is an energy rich 10-carbon hydrocarbon molecule, useful industrially as in cosmetics industry, cleaning products for household and industrial use, and medicinal use. Currently, β-phellandrene for use in commercial industry is extracted from plants, such as lavender, which contain β-phellandrene in their glandular trichome essential oils. However, this example shows that β-phellandrene can be produced by photosynthetic microorganisms, e.g., cyanobacteria and microalgae, through heterologous expression of the gene encoding for the β-phellandrene synthase (β-PHLS), in a reaction of the MEP pathway, driven by the process of cellular photosynthesis. Since the carbon atoms used to generate β-phellandrene in such a system originate from $CO_2$, this would make cyanobacterial and microalgal β-phellandrene production a carbon-neutral source of synthetic chemistry and biofuel feedstock. β-Phellandrene would also be suitable as a building block for the production of longer chain hydrocarbons, to be used as longer chain renewable and carbon-neutral biofuels, pharmaceuticals, and cosmetics.

All publications, accession numbers, and patent applications cited in this specification are herein incorporated by reference as if each individual publication or patent application were specifically and individually indicated to be incorporated by reference.

Illustrative Sequences

SEQ ID NO: 1 Amino acid sequence of the mature
S-β-PHLS protein
MCSLQVSDPIPTGRRSGGYPPALWDFDTIQSLNTEYKGERHMRREEDLIG
QVREMLVHEVEDPTPQLEFIDDLHKLGISCHFENEILQILKSIYLNQNYK
RDLYSTSLAFRLLRQYGFILPQEVEDCFKNEEGTDFKPSFGRDIKGLLQL
YEASFLSRKGEETLQLAREFATKILQKEVDEREFATKMEFPSHWTVQMPN
ARPFIDAYRRRPDMNPVVLELAILDTNIVQAQFQEELKETSRWWESTGIV
QELPFVRDRIVEGYFWTIGVTQRREHGYERIMTAKVIALVTCLDDIYDVY
GTIEELQLFTSTIQRWDLESMKQLPTYMQVSFLALHNEVTEVAYDTLKKK
GYNSTPYLRKTWVDLVESYIKEATWYYNGYKPSMQEYLNNAWISVGSMAI
LNHLFFRFTNERMHKYRDMNRVSSNIVRLADDMGTSLAEVERGDVPKAIQ
CYMNETNASEEEAREYVRRVIQEEWEKLNTELMRDDDDDDDFTLSKYYCE
VVANLTRMAQFIYQDGSDGFGMKDSKVNRLLKETLIERYE SEQ ID NO: 2 The native La-β-PHLS cDNA nucleotide
sequence
ATGTCTACCATTATTGCGATACAAGTGTTGCTTCCTATTCCAACTACTAA
AACATACCCTAGTCATGACTTGGAGAAGTCCTCTTCGCGGTGTCGCTCCT
CCTCCACTCCTCGCCCTAGACTGTGTTGCTCGTTGCAGGTGAGTGATCCG
ATCCCAACGGGCCGGCGATCCGGAGGCTACCCGCCCGCCCTATGGGATTT
CGACACTATTCAATCGCTCAACACCGAGTATAAGGGAGAGAGGCACATGA
GAAGGGAAGAAGACCTAATTGGGCAAGTTAGAGAGATGCTGGTGCATGAA
GTAGAGGATCCCACTCCACAGCTGGAGTTCATTGATGATTTGCATAAGCT
TGGCATATCTTGCCATTTTGAGAATGAAATCCTCCAAATCTTGAAATCCA
TATATCTTAATCAAAACTACAAAAGGGATTTGTACTCAACATCTCTAGCA
TTCAGACTCCTCAGACAATATGGCTTCATCCTTCCACAAGAAGTATTTGA
TTGTTTCAAGAATGAGGAGGGTACGGATTTCAAGCCAAGCTTCGGCCGTG
ATATCAAAGGCTTGTTACAATTGTATGAAGCTTCTTTCCTATCAAGAAAA
GGAGAAGAAACTTTACAACTAGCAAGAGGTTTGCAACAAAGATTCTGCA
AAAAGAAGTTGATGAGAGAGAGTTTGCAACCAAGATGGAGTTCCCTTCTC
ATTGGACGGTTCAAATGCCGAATGCAAGACCTTTCATCGATGCTTACCGT
AGGAGGCCGGATATGAATCCAGTTGTGCTCGAGCTAGCCATACTTGATAC
AAATATAGTTCAAGCACAATTTCAAGAAGAACTCAAAGAGACCTCAAGGT
GGTGGGAGAGTACAGGCATTGTCCAAGAGCTTCCATTTGTGAGGGATAGG
ATTGTGGAAGGCTACTTTTGGACGATTGGAGTGACTCAGAGACGCGAGCA
TGGATACGAAAGAATCATGACCGCAAAGGTTATTGCCTTAGTAACATGTT
TAGACGACATATACGATGTTTATGGCACGATAGAAGAGCTTCAACTTTTC
ACAAGCACAATCCAAAGATGGGATTTGGAATCAATGAAGCAACTCCCTAC
CTACATGCAAGTAAGCTTTCTTGCACTACACAACTTTGTAACCGAGGTGG
CTTACGATACTCTCAAGAAAAAGGGCTACAACTCCACACCATATTTAAGA
AAAACGTGGGTGGATCTTGTTGAATCATATATCAAAGAGGCAACTTGGTA
CTACAACGGTTATAAACCTAGTATGCAAGAATACCTTAACAATGCATGGA
TATCAGTCGGAAGTATGGCTATACTCAACCACCTCTTCTTCCGGTTCACA
AACGAGAGAATGCATAAATACCGCGATATGAACCGTGTCTCGTCCAACAT
TGTGAGGCTTGCTGATGATATGGGAACATCATTGGCTGAGGTGGAGAGAG
GGGACGTGCCGAAAGCAATTCAATGCTACATGAATGAGACGAATGCTTCT
GAAGAAGAAGCAAGAGAATATGTAAGAAGAGTCATACAGGAAGAATGGGA
AAAGTTGAACACAGAATTGATGCGGGATGATGATGATGATGATGATTTTA
CACTATCCAAATATTACTGTGAGGTGGTTGCTAATCTTACAAGAATGGCA
CAGTTTATATACCAAGATGGATCGGATGGCTTCGGCATGAAAGATTCCAA
GGTTAATAGACTGCTAAAAGAGACGTTGATCGAGCGCTACGAATAA SEQ ID NO: 3 Codon-optimized version of the
L. angustifolia (La-S-β-PHLS) cDNA nucleotide
sequence for expression in cyanobacteria, e.g.,
Synechocystis ("S" in gene designation).
TTAATTAACATATGTGTAGTTTGCAAGTTTCTGATCCTATTCCTACCGGA
CGCCGTTCCGGTGGTTATCCCCCGGCCTTATGGGATTTCGATACTATTCA
ATCCCTGAATACCGAATATAAGGGCGAACGTCACATGCGTCGGGAAGAAG
ACTTAATTGGTCAAGTTCGGGAAATGTTGGTGCACGAAGTAGAAGATCCC
ACTCCCCAGTTGGAATTCATTGACGATCTGCATAAATTGGGCATTTCCTG
CCATTTTGAAAACGAGATTCTGCAAATTCTCAAATCCATTTATCTCAACC
AAAACTATAAACGGGACCTCTATTCTACCAGTTTAGCCTTCCGTCTCTTG
CGTCAATACGGGTTTATCTTGCCGCAGGAAGTTTTTGACTGCTTTAAAAA
CGAAGAAGGTACGGATTTTAAACCCAGCTTCGGCCGGGATATTAAGGGTC
TGTTACAGTTGTACGAAGCCTCCTTTTTGTCCCGGAAGGGGGAAGAAACT
TTACAACTCGCCCGCGAATTTGCTACCAAAATCTTGCAAAAGGAAGTCGA

-continued

Illustrative Sequences

```
TGAACGGGAATTTGCTACTAAAATGGAATTTCCCAGTCACTGGACCGTAC
AAATGCCTAACGCTCGGCCTTTTATCGATGCCTATCGTCGGCGTCCCGAC
ATGAACCCCGTGGTTCTGGAACTCGCCATTCTCGATACCAATATCGTGCA
AGCTCAGTTTCAAGAAGAATTGAAGGAGACCTCCCGTTGGTGGGAAAGCA
CGGGGATTGTTCAAGAACTGCCGTTTGTTCGGGACCGGATTGTGGAAGGT
TATTTTTGGACCATTGGTGTTACTCAACGCCGTGAACACGGTTACGAACG
TATTATGACGGCCAAAGTCATCGCTTTGGTGACCTGTTTGGATGATATTT
ATGACGTATATGGCACTATTGAAGAATTGCAACTCTTCACCTCTACGATT
CAGCGTTGGGATTTGGAGTCTATGAAGCAGTTACCGACTTATATGCAGGT
AAGCTTCCTGGCCTTGCACAATTTTGTAACCGAAGTGGCCTATGATACGC
TGAAGAAAAGGGCTACAACTCTACCCCCTATTTGCGGAAGACTTGGGTG
GATTTGGTCGAAAGTTACATTAAGGAAGCCACTTGGTACTATAATGGTA
```

-continued

Illustrative Sequences

```
CAAACCCTCTATGCAGGAATACCTCAACAACGCCTGGATCTCTGTGGGCA
GCATGGCTATTTTGAATCATTTGTTTTTTCGCTTTACTAATGAACGCATG
CATAAGTACCGGGACATGAATCGTGTATCCTCTAATATTGTGCGGTTAGC
CGACGATATGGGAACCTCTTTGGCCGAAGTTGAACGCGGTGACGTGCCCA
AAGCTATCCAATGTTACATGAATGAAACGAACGCCTCTGAGGAGGAGCC
CGCGAATATGTGCGGCGCGTTATCCAGGAAGAATGGGAAAAACTGAACAC
TGAACTGATGCGCGACGACGACGATGACGATGATTTCACCTTAAGTAAAT
ACTACTGCGAAGTCGTTGCTAACCTGACCCGGATGGCTCAGTTCATTTAC
CAAGATGGTTCCGATGGGTTTGGGATGAAAGATTCCAAAGTAAATCGTTT
ACTGAAAGAAACGCTGATTGAGCGCTATGAGTGAAGATCTGCGGCCGC
```

---

What is claimed is:

1. An isolated nucleic acid encoding β-phellandrene synthase, wherein the nucleic acid has at least 80% identity to SEQ ID NO:3.

2. An expression construct comprising the isolated nucleic acid of claim 1 operably linked to a promoter.

3. The expression construct of claim 2, wherein the promoter is an endogenous cyanobacteria promoter.

4. The expression construct of claim 2, wherein the promoter is heterologous to a cyanobacterium.

5. A cyanobacteria host cell comprising the isolated nucleic acid of claim 1.

6. A cell culture comprising a plurality of cyanobacteria host cells that are genetically modified to express a β-phellandrene synthase encoded by a nucleic acid that has at least 80% identity to SEQ ID NO:3.

7. The cell culture of claim 6, wherein the β-phellandrene synthase has at least 90% amino acid sequence identity to SEQ ID NO:1.

8. The cell culture of claim 6, wherein the β-phellandrene synthase is encoded by a nucleic acid having at least 90% identity to SEQ ID NO:3.

9. The cell culture of claim 6, wherein the plurality of cyanobacteria host cells are of a genus selected from the group consisting of the genera *Synechocystis, Synechococcus, Arthrospira, Nostoc*, and *Anabaena*.

10. A cyanobacterial host cell comprising a nucleic acid encoding β-phellandrene synthase integrated into cyanobacterial DNA, wherein the nucleic acid has at least 80% identity to SEQ ID NO:3.

11. The cyanobacterial host cell of claim 10, wherein the nucleic acid encoding β-phellandrene synthase is operably linked to an endogenous PsbA2 promoter.

* * * * *